US009624521B2

(12) United States Patent
Hohmann et al.

(10) Patent No.: US 9,624,521 B2
(45) Date of Patent: Apr. 18, 2017

(54) PRODUCTION OF NON-YEAST STEROLS BY YEAST

(75) Inventors: Hans-Peter Hohmann, Loerrach (DE); Martin Lehmann, Grenzach-Wyhlen (DE); Muriel Merkamm, Les Ulis (FR); Denis Pompon, Gif sur Yvette (FR)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 13/510,636

(22) PCT Filed: Nov. 24, 2010

(86) PCT No.: PCT/EP2010/068127
§ 371 (c)(1),
(2), (4) Date: May 18, 2012

(87) PCT Pub. No.: WO2011/067144
PCT Pub. Date: Jun. 9, 2011

(65) Prior Publication Data
US 2012/0231495 A1    Sep. 13, 2012

(30) Foreign Application Priority Data
Dec. 3, 2009  (EP) .................................... 09014988

(51) Int. Cl.
| C12N 9/02 | (2006.01) |
| C12N 9/10 | (2006.01) |
| C12N 1/19 | (2006.01) |
| C12P 33/06 | (2006.01) |
| C12P 33/00 | (2006.01) |

(52) U.S. Cl.
CPC .............. *C12P 33/00* (2013.01); *C12N 9/001* (2013.01); *C12N 9/0067* (2013.01); *C12N 9/0071* (2013.01); *C12N 9/0083* (2013.01); *C12N 9/1007* (2013.01); *C12P 33/06* (2013.01)

(58) Field of Classification Search
None
See application file for complete search history.

(56) References Cited

U.S. PATENT DOCUMENTS

| 4,119,647 | A * | 10/1978 | Liebman et al. .............. 552/546 |
| 5,668,000 | A | 9/1997 | Akiyoshi et al. |
| 6,562,609 | B1 | 5/2003 | Russell et al. |
| 7,608,421 | B2 * | 10/2009 | Lang et al. ...................... 435/52 |
| 2006/0240508 | A1 | 10/2006 | Lang et al. |
| 2010/0297712 | A1 | 11/2010 | Fujii et al. |

FOREIGN PATENT DOCUMENTS

| WO | WO 00/23596 | 4/2000 |
| WO | WO 2007/138894 | 12/2007 |
| WO | WO 2007/138894 A1 | 12/2007 |

OTHER PUBLICATIONS

Araya et al., Biochimica et Biophysica Acta 1632:40-47, 2003.*
Lund et al., cDNA cloning of mouse and human cholesterol 25-hydroxylases, polytopic membrane proteins that synthesize a potent oxysterol regulator of lipid metabolism, J. Biol. Chem., 1998, 273, 34316-27.*
Russell, Oxysterol biosynthetic enzymes, Biochim. Biophys. Acta, 2000, 1529, 126-35.*
Grimalt et al., Assessment of fecal sterols and ketones as indicators of urban sewage inputs to coastal waters, Environ. Sci. Technol., 1990, 24, 357-363.*
Sakaki et al., Organella-targeted expression of rat liver cytochrome P450C27 in yeast, J. Biol. Chem., 1992, 267, 16497-502.*
Björkhem et al., "On the 25-hydroxylation of vitamin D3 in vitro studied with a mass fragmentographic technique," J. Biol. Chem., 1979, 254, 9518-24.*
UniProt, Accession No. P17178, 2009, www.uniprot.org.*
Sakaki et al., Practical application of mammalian cytochrome P450, J. Biosci. and Bioeng., 2000, 90, 583-590.*
Araya et al., Metabolism of 25-hydroxyvitamin D3 by microsomal and mitochondrial vitamin D3 25-hydroxylases (CYP2D25 and CYP27A1): a novel reaction by CYP27A1, Biochim. Biophysica Acta, 2003, 1632, 40-47.*
Postlind et al., 27-oxygenation of C27-sterols and 25-hydroxylation of vitamin D3 in kidney: cloning, structure and expression of pig kidney CYP27A, Biochem. J., 2000, 347, 349-56.*
Gustafsson et al., Codon bias and heterologous protein expression, Trends Biotechnol., 2004, 22, 346-53.*
International Search Report for PCT/EP2010/068127, mailed May 18, 2011.
Written Opinion for PCT/EP2010/068127, mailed May 18, 2011.
Office Action in related Japanese Patent Application No. 2012-541408; Dispatch Date: Sep. 30, 2014; 8 pages; in Japanese with English Translation.
Björkhem et al., "On the 25-Hydroxylation of Vitamin D3 in Vitro Studied with a Mass Fragmentographic Technique"; The Journal of Biological Chemistry; vol. 254; No. 19; (1979); pp. 9518-9524.

* cited by examiner

*Primary Examiner* — Robert Mondesi
*Assistant Examiner* — Todd M Epstein
(74) *Attorney, Agent, or Firm* — Nixon & Vanderhye P.C.

(57) ABSTRACT

This invention relates to the production of 7-dehydrocholesterol, 25-hydroxy-7-dehydrocholesterol, and 25-hydroxy ergosterol in yeast such as *Saccharomyces cerevisiae*. It also relates to various enzymes catalyzing the reduction of the double bond at position 24 of lanosterol, dimethyl zymosterol, methyl zymosterol, zymosterol, cholesta-7, 24-dienol, or cholesta-5,7,24-trienol; or the hydroxylation at position 25 of ergosterol, 7-dehydrocholesterol, cholesta-8-enol, and cholesta-7-enol. It also relates to various nucleic acids encoding cholesterol C25-hydroxylases and sterol Δ24-reductases and their use to produce and hydroxylate 7-dehydrocholesterol or ergosterol. It also relates to the yeast strains so produced, and methods of making these sterols that include the steps of cultivaton a transformed yeast cell, and harvesting the resulting sterol(s).

7 Claims, 19 Drawing Sheets

V51TDH-S24R1 (8619bp)

V51TDH-S24R2 (8619bp)

pFLAde-S24R1 (8814bp)

V51-C25H1 (7845bp)

V51-C25H3  (7845bp)

*ERT/pFLAde-S24R1/V51-C25H1 (peak 8.5 min)*

25OH-7DHC-Ac standard

W303/V51-C25H1 (peak 8.7 min)

W303/V51-C25H1 (peak 10.0 min)

W303/V51-C25H1 (peak 8.7 min)

W303/V51-C25H1 (peak 10.0 min)

SEQUENCE LISTING

<160> NUMBER OF SEQ ID NOS: 32

<210> SEQ ID NO 1
<211> LENGTH: 1569
<212> TYPE: DNA
<213> ORGANISM: Artificial Sequence
<220> FEATURE:
<223> OTHER INFORMATION: codon-optimized rat sterol delta24-reductase gene (S24R1)

<400> SEQUENCE: 1

| | |
|---|---|
| ggatccaaaa tggaaccagc tgtttcttta gctgtttgtg ctttattatt tttattatgg | 60 |
| gtaagagtca aaggtcttga atttgtctta attcatcaaa ggtgggtgtt tgtctgttta | 120 |
| tttttattac cattatcttt aatctttgat atctattatt atgttagagc ttgggttgtt | 180 |
| tttaaattat cttctgctcc aagactacat gaacaaagag ttcaagatat ccaaaaacaa | 240 |
| gttagagaat ggaaagaaca aggttctaaa acttttatgt gtaccggtcg gcctgggtgg | 300 |
| ctcactgtgt cattaagggt tggtaaatat aaaaaaactc ataaaatat catgatcaat | 360 |
| ttaatggata tcttagaagt tgatactaaa aaacaaatcg tcagggttga acctcttgtc | 420 |
| tctatggggc aagtcactgc attattaaat tctattggtt ggacgcttcc tgtcctccca | 480 |
| gagttagacg atcttactgt tggtggttta atcatgggta ctggtatcga atcttcatct | 540 |
| cataaatatg gtcttttttca acatatttgt accgcttatg aactaatcct ggctgatggc | 600 |
| tcatttgtgc gttgtacccc ttcggaaaac tccgatctat tttatgcagt cccatggagt | 660 |
| tgtggtactt taggtttttt agttgctgct gaaatcagaa tcatcccagc aaaaaagtat | 720 |
| gtcaagctac gatttgaacc tgttagaggt ctggaagcaa tctgtgaaaa gtttacacat | 780 |
| gaatctcaaa gattagaaaa tcattttgtt gaagggcttc tctatagtct ggatgaggcg | 840 |
| gtgattatga cggggggtgat gacgacgac gttgagccat ctaaattaaa ttctatcggt | 900 |
| tcttattata aaccatggtt ttttaaacat gttgaaaatt atttaaaaac taatagggaa | 960 |
| ggattagaat acattccatt aagacattat tatcatagac atactaggtc tatcttttgg | 1020 |
| gaattacaag atatcatccc atttggtaat aatccaatct ttagatattt atttggttgg | 1080 |
| atggttccac caaaaatctc tttattaaaa ttaactcaag gtgaaacttt acgaaagcta | 1140 |
| tatgagcaac accacgtcgt tcaagatatg ttagttccaa tgaaatgttt atctcaagca | 1200 |
| ttacataacct tccaaaatga tatccatgtt tatccaatct ggttatgtcc atttatctta | 1260 |
| ccatctcaac ctggtctggt ccaccctaaa ggtgacgaag ctgaacttta tgttgatatc | 1320 |
| ggtgcctatg gtgagccaag agttaaacat tttgaagcta gatcatgtat gagacaatta | 1380 |
| gaaaaatttg ttagatcagt tcatggtttt caaatgctat atgcagattg ttacatgaac | 1440 |
| agagaagaat tttgggaaat gttcgatggt tctttatatc ataaattaag aaaacaatta | 1500 |
| ggttgtcaag atgcttttcc agaagtttat gataaaatct gtaaagctgc tagacactaa | 1560 |
| tgagaattc | 1569 |

<210> SEQ ID NO 2
<211> LENGTH: 516
<212> TYPE: PRT
<213> ORGANISM: Rattus norvegicus

<400> SEQUENCE: 2

Met Glu Pro Ala Val Ser Leu Ala Val Cys Ala Leu Leu Phe Leu Leu
1               5                   10                  15

Trp Val Arg Val Lys Gly Leu Glu Phe Val Leu Ile His Gln Arg Trp
            20                  25                  30

Val Phe Val Cys Leu Phe Leu Leu Pro Leu Ser Leu Ile Phe Asp Ile
        35                  40                  45

Tyr Tyr Tyr Val Arg Ala Trp Val Val Phe Lys Leu Ser Ser Ala Pro
    50                  55                  60

Arg Leu His Glu Gln Arg Val Gln Asp Ile Gln Lys Gln Val Arg Glu

-continued

```
                65                  70                  75                  80
Trp Lys Glu Gln Gly Ser Lys Thr Phe Met Cys Thr Gly Arg Pro Gly
                    85                  90                  95
Trp Leu Thr Val Ser Leu Arg Val Gly Lys Tyr Lys Thr His Lys
                100                 105                 110
Asn Ile Met Ile Asn Leu Met Asp Ile Leu Glu Val Asp Thr Lys Lys
                115                 120                 125
Gln Ile Val Arg Val Glu Pro Leu Val Ser Met Gly Gln Val Thr Ala
            130                 135                 140
Leu Leu Asn Ser Ile Gly Trp Thr Leu Pro Val Leu Pro Glu Leu Asp
145                 150                 155                 160
Asp Leu Thr Val Gly Gly Leu Ile Met Gly Thr Gly Ile Glu Ser Ser
                165                 170                 175
Ser His Lys Tyr Gly Leu Phe Gln His Ile Cys Thr Ala Tyr Glu Leu
                180                 185                 190
Ile Leu Ala Asp Gly Ser Phe Val Arg Cys Thr Pro Ser Glu Asn Ser
                195                 200                 205
Asp Leu Phe Tyr Ala Val Pro Trp Ser Cys Gly Thr Leu Gly Phe Leu
            210                 215                 220
Val Ala Ala Glu Ile Arg Ile Ile Pro Ala Lys Lys Tyr Val Lys Leu
225                 230                 235                 240
Arg Phe Glu Pro Val Arg Gly Leu Glu Ala Ile Cys Glu Lys Phe Thr
                245                 250                 255
His Glu Ser Gln Arg Leu Glu Asn His Phe Val Glu Gly Leu Leu Tyr
                260                 265                 270
Ser Leu Asp Glu Ala Val Ile Met Thr Gly Val Met Thr Asp Asp Val
            275                 280                 285
Glu Pro Ser Lys Leu Asn Ser Ile Gly Ser Tyr Tyr Lys Pro Trp Phe
            290                 295                 300
Phe Lys His Val Glu Asn Tyr Leu Lys Thr Asn Arg Glu Gly Leu Glu
305                 310                 315                 320
Tyr Ile Pro Leu Arg His Tyr Tyr His Arg His Thr Arg Ser Ile Phe
                325                 330                 335
Trp Glu Leu Gln Asp Ile Ile Pro Phe Gly Asn Asn Pro Ile Phe Arg
                340                 345                 350
Tyr Leu Phe Gly Trp Met Val Pro Pro Lys Ile Ser Leu Leu Lys Leu
                355                 360                 365
Thr Gln Gly Glu Thr Leu Arg Lys Leu Tyr Glu Gln His His Val Val
            370                 375                 380
Gln Asp Met Leu Val Pro Met Lys Cys Leu Ser Gln Ala Leu His Thr
385                 390                 395                 400
Phe Gln Asn Asp Ile His Val Tyr Pro Ile Trp Leu Cys Pro Phe Ile
                405                 410                 415
Leu Pro Ser Gln Pro Gly Leu Val His Pro Lys Gly Asp Glu Ala Glu
                420                 425                 430
Leu Tyr Val Asp Ile Gly Ala Tyr Gly Glu Pro Arg Val Lys His Phe
                435                 440                 445
Glu Ala Arg Ser Cys Met Arg Gln Leu Glu Lys Phe Val Arg Ser Val
            450                 455                 460
His Gly Phe Gln Met Leu Tyr Ala Asp Cys Tyr Met Asn Arg Glu Glu
465                 470                 475                 480
Phe Trp Glu Met Phe Asp Gly Ser Leu Tyr His Lys Leu Arg Lys Gln
                485                 490                 495
```

Leu Gly Cys Gln Asp Ala Phe Pro Glu Val Tyr Asp Lys Ile Cys Lys
        500                 505                 510

Ala Ala Arg His
        515

```
<210> SEQ ID NO 3
<211> LENGTH: 1569
<212> TYPE: DNA
<213> ORGANISM: Artificial Sequence
<220> FEATURE:
<223> OTHER INFORMATION: codon-optimized Danio rerio delta24-reductase
      gene (S24R2)

<400> SEQUENCE: 3
ggatccaaaa tggaccctt  gctttacctt ggaggcctag cggtcctctt ccttatttgg      60
attaaggtaa aaggtttaga atatgttatt atccatcaaa gatggatctt tgtttgttta     120 ttttttattac cattatctgt cgtcttcgat gtttattatc atttaagagc ttggatcatc    180
tttaaaatgt gttctgctcc aaaacaacat gatcaaagag ttaggatat tcaaaggcaa     240 gtccgtgaat ggcggaagga tggggggtaag aaatacatgt gcaccggtag gccaggttgg    300
ctgactgttt ctttaagagt cggtaaatat aaaaaaactc ataaaatat catgatcaat    360 atgatggata tcttagaagt tgataccaaa agaaaagttg tgagagtaga accattagct    420
aatatgggtc aagttactgc tttattaaat tctatcggtt ggacattacc tgtcttacca    480
gaacttgatg acttaactgt tggtggttta gtcatgggca ctggtattga atcttcttct    540
catatctatg gtttatttca acatatctgt gttgcatttg aattagtttt agctgatggt    600
tctttagtta ggtgtacaga aaaggaaaac tctgatttat tttatgctgt cccatggagc    660
tgtggtacct taggttttct agtcgcggct gaaattcgta ttattcctgc tcaaaaatgg    720
gtcaaattac attatgaacc tgtcagggga ttagacgcta tttgcaaaaa atttgctgaa    780
gagtctgcta ataagaaaaa tcaatttgtt gaaggattac aatattctag agatgaagct    840
gttattatga cgggtgtaat gacggatcat gcagaacccg ataaaactaa ttgtattggg    900
tattattata aaccttggtt ctttagacat gttgaatctt ttttaaaaca aaatagagtt    960
gctgttgaat atatcccatt aagacattat tatcatagac atactagatc aatcttttgg   1020
gaactgcaag acatcattcc atttggcaat aatccacttt ttaggtacgt tttt ggatgg   1080 atggtgccac caaaaatctc tttattaaaa ttaactcaag gtgaaactat cagaaaatta   1140
tatgaacaac atcatgttgt tcaagatatg ttagttccaa tgaaagatat caaagctgct   1200
atccaaagat tcatgaaga  tattcatgtc tatccattat ggctttgtcc attttttatta   1260 ccaaatcaac ctggaatggt gcatccgaaa ggggatgagg acgagttata tgtggatatt   1320
ggggcctacg gcgaacccaa agtaaaacat ttcgaagcaa cttcttctac tagacaatta   1380
gaaaaatttg tccgtgatgt ccatggttttt caaatgctct acgcagatgt ctatatggag   1440
agaaaagaat tgggaaat gttcgacggt actttatatc ataaattaag agaagaactg   1500
ggctgtaagg atgcctttcc cgaagtgttt gacaaaatct gtaaaagtgc acgtcattaa   1560
tgagaattc                                                            1569

<210> SEQ ID NO 4
<211> LENGTH: 516
<212> TYPE: PRT
<213> ORGANISM: Danio rerio

<400> SEQUENCE: 4
```

```
Met Asp Pro Leu Leu Tyr Leu Gly Gly Leu Ala Val Leu Phe Leu Ile
1               5                   10                  15

Trp Ile Lys Val Lys Gly Leu Glu Tyr Val Ile Ile His Gln Arg Trp
            20                  25                  30

Ile Phe Val Cys Leu Phe Leu Pro Leu Ser Val Val Phe Asp Val
        35                  40                  45

Tyr Tyr His Leu Arg Ala Trp Ile Ile Phe Lys Met Cys Ser Ala Pro
    50                  55                  60

Lys Gln His Asp Gln Arg Val Arg Asp Ile Gln Arg Gln Val Arg Glu
65                  70                  75                  80

Trp Arg Lys Asp Gly Lys Lys Tyr Met Cys Thr Gly Arg Pro Gly
                85                  90                  95

Trp Leu Thr Val Ser Leu Arg Val Gly Lys Tyr Lys Lys Thr His Lys
            100                 105                 110

Asn Ile Met Ile Asn Met Met Asp Ile Leu Glu Val Asp Thr Lys Arg
            115                 120                 125

Lys Val Val Arg Val Glu Pro Leu Ala Asn Met Gly Gln Val Thr Ala
130                 135                 140

Leu Leu Asn Ser Ile Gly Trp Thr Leu Pro Val Leu Pro Glu Leu Asp
145                 150                 155                 160

Asp Leu Thr Val Gly Gly Leu Val Met Gly Thr Gly Ile Glu Ser Ser
                165                 170                 175

Ser His Ile Tyr Gly Leu Phe Gln His Ile Cys Val Ala Phe Glu Leu
            180                 185                 190

Val Leu Ala Asp Gly Ser Leu Val Arg Cys Thr Glu Lys Glu Asn Ser
            195                 200                 205

Asp Leu Phe Tyr Ala Val Pro Trp Ser Cys Gly Thr Leu Gly Phe Leu
    210                 215                 220

Val Ala Ala Glu Ile Arg Ile Ile Pro Ala Gln Lys Trp Val Lys Leu
225                 230                 235                 240

His Tyr Glu Pro Val Arg Gly Leu Asp Ala Ile Cys Lys Lys Phe Ala
                245                 250                 255

Glu Glu Ser Ala Asn Lys Glu Asn Gln Phe Val Glu Gly Leu Gln Tyr
            260                 265                 270

Ser Arg Asp Glu Ala Val Ile Met Thr Gly Val Met Thr Asp His Ala
    275                 280                 285

Glu Pro Asp Lys Thr Asn Cys Ile Gly Tyr Tyr Tyr Lys Pro Trp Phe
    290                 295                 300

Phe Arg His Val Glu Ser Phe Leu Lys Gln Asn Arg Val Ala Val Glu
305                 310                 315                 320

Tyr Ile Pro Leu Arg His Tyr His Arg His Thr Arg Ser Ile Phe
                325                 330                 335

Trp Glu Leu Gln Asp Ile Ile Pro Phe Gly Asn Asn Pro Leu Phe Arg
            340                 345                 350

Tyr Val Phe Gly Trp Met Val Pro Pro Lys Ile Ser Leu Leu Lys Leu
            355                 360                 365

Thr Gln Gly Glu Thr Ile Arg Lys Leu Tyr Glu Gln His His Val Val
    370                 375                 380

Gln Asp Met Leu Val Pro Met Lys Asp Ile Lys Ala Ala Ile Gln Arg
385                 390                 395                 400

Phe His Glu Asp Ile His Val Tyr Pro Leu Trp Leu Cys Pro Phe Leu
                405                 410                 415
```

```
Leu Pro Asn Gln Pro Gly Met Val His Pro Lys Gly Asp Glu Asp Glu
            420                 425                 430

Leu Tyr Val Asp Ile Gly Ala Tyr Gly Glu Pro Lys Val Lys His Phe
            435                 440                 445

Glu Ala Thr Ser Ser Thr Arg Gln Leu Glu Lys Phe Val Arg Asp Val
        450                 455                 460

His Gly Phe Gln Met Leu Tyr Ala Asp Val Tyr Met Glu Arg Lys Glu
465                 470                 475                 480

Phe Trp Glu Met Phe Asp Gly Thr Leu Tyr His Lys Leu Arg Glu Glu
                485                 490                 495

Leu Gly Cys Lys Asp Ala Phe Pro Glu Val Phe Asp Lys Ile Cys Lys
            500                 505                 510

Ser Ala Arg His
        515

<210> SEQ ID NO 5
<211> LENGTH: 831
<212> TYPE: DNA
<213> ORGANISM: Artificial Sequence
<220> FEATURE:
<223> OTHER INFORMATION: codon-optimized pig cholesterol C25-hydroxylase
      gene (C25H1)

<400> SEQUENCE: 5
ggatccaaaa tgagcggcca caacaactcc gagcttttcg tcctttgcag ctccagccag    60
ctgttcctgc agcccctttg ggaccacctg aagacctggg agacccttat cctgtcgccc   120
ttcttcccag tcttcttctc catcaccacc tacttgggct ctgcctgcc cttcgtggta   180 ctggatgtct tatgcccatg ggtgcccgca ctgaggcgtt acaagatcca cccagacttc   240
tcgccatcgg tgtggcagct gctgccctgc ctggggctga cactttacca gcatgtggtg   300
ttcgtgttcc caatgactct gttgcactgg gcagcaagcc cagttcttct gcccccagaa   360
gcccccgagc tgcttcagct ggtgcgtcac atcgtgctgt gcctgctgct tttcgacacc   420 gaattttca tctggcatgt gctgcatcac aaagtgcctt ggctgtacag gaccttccac   480
aagatgcacc accagaactc gtcctcgttc gcactggcca cagtacat gagtgtcggg    540 gagctacttt ctttgggtgt ctttgacatg gtgaacatca tgctgcttag gtgccaccca   600
cttaccgtcc tgatcttcca cgtgatcaac atctggctgt cggtggagga ccactccggc   660
tatgacttcc cctggtccgc tcacagacta gtaccttcg ggtggtatgg gggcgtgaca    720
caccacgacc tacatcactc ccagtttaac tgcaacttcg ccccttactt cacacactgg   780
gacaaaatac tgggaacact gaggtctgct catgccaagt aatgagaatt c            831

<210> SEQ ID NO 6
<211> LENGTH: 270
<212> TYPE: PRT
<213> ORGANISM: pig

<400> SEQUENCE: 6

Met Ser Gly His Asn Asn Ser Glu Leu Phe Val Leu Cys Ser Ser Ser
1               5                   10                  15

Gln Leu Phe Leu Gln Pro Leu Trp Asp His Leu Lys Thr Trp Glu Thr
            20                  25                  30

Leu Ile Leu Ser Pro Phe Phe Pro Val Phe Ser Ile Thr Thr Tyr
        35                  40                  45

Leu Gly Phe Cys Leu Pro Phe Val Val Leu Asp Val Leu Cys Pro Trp
    50                  55                  60
```

```
Val Pro Ala Leu Arg Arg Tyr Lys Ile His Pro Asp Phe Ser Pro Ser
 65                  70                  75                  80

Val Trp Gln Leu Leu Pro Cys Leu Gly Leu Thr Leu Tyr Gln His Val
                 85                  90                  95

Val Phe Val Phe Pro Met Thr Leu Leu His Trp Ala Ala Ser Pro Val
            100                 105                 110

Leu Leu Pro Pro Glu Ala Pro Glu Leu Leu Gln Leu Val Arg His Ile
        115                 120                 125

Val Leu Cys Leu Leu Leu Phe Asp Thr Glu Phe Phe Ile Trp His Val
    130                 135                 140

Leu His His Lys Val Pro Trp Leu Tyr Arg Thr Phe His Lys Met His
145                 150                 155                 160

His Gln Asn Ser Ser Ser Phe Ala Leu Ala Thr Gln Tyr Met Ser Val
                165                 170                 175

Gly Glu Leu Leu Ser Leu Gly Val Phe Asp Met Val Asn Ile Met Leu
            180                 185                 190

Leu Arg Cys His Pro Leu Thr Val Leu Ile Phe His Val Ile Asn Ile
        195                 200                 205

Trp Leu Ser Val Glu Asp His Ser Gly Tyr Asp Phe Pro Trp Ser Ala
    210                 215                 220

His Arg Leu Val Pro Phe Gly Trp Tyr Gly Val Thr His His Asp
225                 230                 235                 240

Leu His His Ser Gln Phe Asn Cys Asn Phe Ala Pro Tyr Phe Thr His
                245                 250                 255

Trp Asp Lys Ile Leu Gly Thr Leu Arg Ser Ala His Ala Lys
            260                 265                 270

<210> SEQ ID NO 7
<211> LENGTH: 270
<212> TYPE: PRT
<213> ORGANISM: pig

<400> SEQUENCE: 7

Met Ser Gly His Asn Asn Ser Glu Leu Leu Val Leu Cys Ser Ser Gly
  1               5                  10                  15

Gln Leu Phe Leu Gln Pro Leu Trp Asp His Leu Lys Thr Trp Glu Thr
                 20                  25                  30

Leu Ile Gln Ser Pro Phe Phe Pro Val Phe Phe Ser Ile Thr Thr Tyr
             35                  40                  45

Leu Gly Phe Cys Leu Pro Phe Val Val Leu Asp Val Leu Cys Pro Trp
         50                  55                  60

Val Pro Ala Leu Arg Arg Tyr Lys Ile His Pro Asp Phe Ser Pro Ser
 65                  70                  75                  80

Val Trp Gln Leu Leu Pro Cys Leu Gly Leu Thr Leu Tyr Gln His Val
                 85                  90                  95

Val Phe Val Phe Pro Met Thr Leu Leu His Trp Ala Ala Ser Pro Val
            100                 105                 110

Leu Leu Pro Pro Glu Ala Pro Glu Leu Leu Gln Leu Val Arg His Ile
        115                 120                 125

Val Leu Cys Leu Leu Leu Phe Asp Thr Glu Phe Phe Ile Trp His Val
    130                 135                 140

Leu His His Lys Val Pro Trp Leu Tyr Arg Thr Phe His Lys Met His
145                 150                 155                 160

His Gln Asn Ser Ser Ser Phe Ala Leu Ala Thr Gln Tyr Met Ser Val
```

```
                    165                 170                 175

Gly Glu Leu Leu Ser Leu Gly Val Phe Asp Met Val Asn Ile Met Leu
            180                 185                 190

Leu Arg Cys His Pro Leu Thr Val Leu Ile Phe His Val Ile Asn Ile
        195                 200                 205

Trp Leu Ser Val Glu Asp His Ser Gly Tyr Asp Phe Pro Trp Ser Thr
    210                 215                 220

His Arg Leu Val Pro Phe Gly Trp Tyr Gly Gly Val Thr His His Asp
225                 230                 235                 240

Leu His His Ser Gln Phe Asn Cys Asn Phe Ala Pro Tyr Phe Thr His
                245                 250                 255

Trp Asp Lys Ile Leu Gly Thr Leu Arg Ser Ala His Ala Lys
            260                 265                 270

<210> SEQ ID NO 8
<211> LENGTH: 831
<212> TYPE: DNA
<213> ORGANISM: Artificial Sequence
<220> FEATURE:
<223> OTHER INFORMATION: codon-optimized dog sterol C25-hydroxylase gene
      (C25H3)

<400> SEQUENCE: 8
ggatccaaaa tgtcttcaca taattcttct ggtcctttag ccttaggacc acctggtcaa      60
ctattattac aacctttatg ggaccaagtt agggcaaggg cagcattagc gcaatcgcct     120 cccttt gcag tccttttttc tatcactgct tatttaggtt gttgtttacc atttgtttta     180
ttagatttat tatgtccaag agttagagca ttaaggagat ataaagtcca tcccgattgt     240
ggaccatctg caaggcaatt attaggttgt ttaggtagga ctgtctgtca acatgtagct     300
ttattattac cagcttcttt attacattgt gccagggtc ccgctccatg gccgagagaa      360
gcaccagaat tattacaatt agctagacat gttttaggtt gtttattatt atttgatgct     420 gaagttttg cttggcacgt tttacatcat agagttccat ggctttatag aacttttcat      480
aaattacatc atcaacatgc tgcttcattt gctttagcta ctcaatatat gggtgcttgg     540
gagttattat ctttaggttt ttttcatgtt ttaaatgttg ttttattaca atgtcatcca     600
ttatctgttt tagcttttca tttattaaat atctggctat ctgttgaaga tcattcaggt     660
tatgatttcc catggtcgac ccatcgatta gtcccctttg gttggtacgg tggagttgct     720
catcatgatt tacatcattc acaatttaat tgtaattttg caccatattt tactcattgg     780
gacagaattt tgggtacctt aaggtctgca ccagccaaat aatgagaatt c              831

<210> SEQ ID NO 9
<211> LENGTH: 270
<212> TYPE: PRT
<213> ORGANISM: Canis familiaris

<400> SEQUENCE: 9

Met Ser Ser His Asn Ser Ser Gly Pro Leu Ala Leu Gly Pro Pro Gly
1               5                   10                  15

Gln Leu Leu Leu Gln Pro Leu Trp Asp Gln Val Arg Ala Arg Ala Ala
            20                  25                  30

Leu Ala Gln Ser Pro Pro Phe Ala Val Leu Phe Ser Ile Thr Ala Tyr
        35                  40                  45

Leu Gly Cys Cys Leu Pro Phe Val Leu Leu Asp Leu Leu Cys Pro Arg
    50                  55                  60
```

Val Arg Ala Leu Arg Arg Tyr Lys Val His Pro Asp Cys Gly Pro Ser
65                  70                  75                  80

Ala Arg Gln Leu Leu Gly Cys Leu Gly Arg Thr Val Cys Gln His Val
            85                  90                  95

Ala Leu Leu Leu Pro Ala Ser Leu Leu His Cys Ala Arg Gly Pro Ala
        100                 105                 110

Pro Trp Pro Arg Glu Ala Pro Glu Leu Leu Gln Leu Ala Arg His Val
    115                 120                 125

Leu Gly Cys Leu Leu Phe Asp Ala Glu Val Phe Ala Trp His Val
130                 135                 140

Leu His His Arg Val Pro Trp Leu Tyr Arg Thr Phe His Lys Leu His
145                 150                 155                 160

His Gln His Ala Ala Ser Phe Ala Leu Ala Thr Gln Tyr Met Gly Ala
                165                 170                 175

Trp Glu Leu Leu Ser Leu Gly Phe Phe His Val Leu Asn Val Val Leu
            180                 185                 190

Leu Gln Cys His Pro Leu Ser Val Leu Ala Phe His Leu Leu Asn Ile
        195                 200                 205

Trp Leu Ser Val Glu Asp His Ser Gly Tyr Asp Phe Pro Trp Ser Thr
210                 215                 220

His Arg Leu Val Pro Phe Gly Trp Tyr Gly Gly Val Ala His His Asp
225                 230                 235                 240

Leu His His Ser Gln Phe Asn Cys Asn Phe Ala Pro Tyr Phe Thr His
                245                 250                 255

Trp Asp Arg Ile Leu Gly Thr Leu Arg Ser Ala Pro Ala Lys
            260                 265                 270

<210> SEQ ID NO 10
<211> LENGTH: 27
<212> TYPE: DNA
<213> ORGANISM: Artificial Sequence
<220> FEATURE:
<223> OTHER INFORMATION: synthetic primer

<400> SEQUENCE: 10
caccggtgcc atttcaaaga atacgta                                        27

<210> SEQ ID NO 11
<211> LENGTH: 28
<212> TYPE: DNA
<213> ORGANISM: Artificial Sequence
<220> FEATURE:
<223> OTHER INFORMATION: synthetic primer

<400> SEQUENCE: 11
tggatcctta tgtgtgttta ttcgaaac                                       28

<210> SEQ ID NO 12
<211> LENGTH: 34
<212> TYPE: DNA
<213> ORGANISM: Artificial Sequence
<220> FEATURE:
<223> OTHER INFORMATION: synthetic primer

<400> SEQUENCE: 12
cggatccact agtaacgccg tatcgtgatt aacg                                34

<210> SEQ ID NO 13
<211> LENGTH: 33
<212> TYPE: DNA

<210> SEQ ID NO 13
<211> LENGTH: 33
<212> TYPE: DNA
<213> ORGANISM: Artificial Sequence
<220> FEATURE:
<223> OTHER INFORMATION: synthetic primer

<400> SEQUENCE: 13
aggatcctcc tgacgtagct atcctcggtt ctg         33

<210> SEQ ID NO 14
<211> LENGTH: 29
<212> TYPE: DNA
<213> ORGANISM: Artificial Sequence
<220> FEATURE:
<223> OTHER INFORMATION: synthetic primer

<400> SEQUENCE: 14
aggcgcgcca ccggtgccat ttcaaagaa         29

<210> SEQ ID NO 15
<211> LENGTH: 29
<212> TYPE: DNA
<213> ORGANISM: Artificial Sequence
<220> FEATURE:
<223> OTHER INFORMATION: synthetic primer

<400> SEQUENCE: 15
aggcgcgccc aagctttaac gaacgcaga         29

<210> SEQ ID NO 16
<211> LENGTH: 68
<212> TYPE: DNA
<213> ORGANISM: Artificial Sequence
<220> FEATURE:
<223> OTHER INFORMATION: synthetic primer

<400> SEQUENCE: 16
cataagatga gtgaaacaga attgagaaaa agacaggccc aatcaaattc gggtcgaaaa         60
aagaaaag         68

<210> SEQ ID NO 17
<211> LENGTH: 61
<212> TYPE: DNA
<213> ORGANISM: Artificial Sequence
<220> FEATURE:
<223> OTHER INFORMATION: synthetic primer

<400> SEQUENCE: 17
ctagcgacga aaagcatcat tggagtgaat aacttggact taccattctt agcattttga         60
c         61

<210> SEQ ID NO 18
<211> LENGTH: 272
<212> TYPE: PRT
<213> ORGANISM: Pan troglodytes

<400> SEQUENCE: 18

Met Ser Cys His Asn Cys Ser Asp Pro Gln Val Leu Cys Ser Ser Gly
1               5                   10                  15

Gln Leu Phe Leu Gln Pro Leu Trp Asp His Leu Arg Ser Trp Glu Ala
            20                  25                  30

Leu Leu Gln Ser Pro Phe Phe Pro Val Ile Phe Ser Ile Thr Thr Tyr
        35                  40                  45

Val Gly Phe Cys Leu Pro Phe Val Val Leu Asp Ile Leu Cys Ser Trp
    50                  55                  60

Val Pro Ala Leu Arg Arg Tyr Lys Ile His Pro Asp Phe Ser Pro Ser
65                  70                  75                  80

Ala Arg Gln Leu Leu Pro Cys Leu Gly Gln Thr Leu Tyr Gln His Val
            85                  90                  95

Met Phe Val Phe Pro Val Thr Leu Leu His Trp Ala Arg Ser Pro Ala
            100                 105                 110

Leu Leu Pro His Glu Ala Pro Glu Leu Leu Leu Leu His His Ile
        115                 120                 125

Leu Phe Cys Leu Leu Leu Phe Asp Met Glu Phe Phe Val Trp His Leu
    130                 135                 140

Leu His His Lys Val Pro Trp Leu Tyr Arg Thr Phe His Lys Val His
145                 150                 155                 160

His Gln Asn Ser Ser Ser Phe Ala Leu Ala Thr Gln Tyr Met Ser Val
                165                 170                 175

Trp Glu Leu Phe Ser Leu Gly Phe Phe Asp Met Met Asn Val Thr Leu
            180                 185                 190

Leu Gly Cys His Pro Leu Thr Thr Leu Thr Phe His Val Val Asn Ile
        195                 200                 205

Trp Leu Ser Val Glu Asp His Ser Gly Tyr Asn Phe Pro Trp Ser Thr
    210                 215                 220

His Arg Leu Val Pro Phe Gly Trp Tyr Gly Val Val His His Asp
225                 230                 235                 240

Leu His His Ser His Phe Asn Cys Asn Phe Ala Pro Tyr Phe Thr His
                245                 250                 255

Trp Asp Lys Ile Leu Gly Thr Leu Arg Thr Ala Ser Val Pro Ala Arg
            260                 265                 270

<210> SEQ ID NO 19
<211> LENGTH: 822
<212> TYPE: DNA
<213> ORGANISM: Artificial Sequence
<220> FEATURE:
<223> OTHER INFORMATION: codon optimized chimpanzee cholesterol
      25-hydroxylase gene

<400> SEQUENCE: 19
atgtcatgtc ataactgttc tgatcctcaa gttttgtgtt caagtggtca actgttcctg    60
caacctcttt gggatcactt gagaagttgg gaggcactat tgcagtctcc attcttccct   120
gtgatcttct ctattactac ctatgttgga ttctgtttgc catttgtggt gctggacatt   180
ctatgctcat gggttcctgc cttgagaagg tataagadat atcctgactt tccccttct   240 gctagacaac ttttaccatg cttagggcaa acattgtacc aacacgtgat gttcgttttc   300
ccagtgacat tgttgcattg gctagatccc cagctttac ttccacacga agccccagaa   360
ctgttacttc tactacacca cattctgttc tgcttgctgc tatttgatat ggagttttc   420 gtatggcact tgcttcatca caaagtccca tggttataca gaacctttca taaagtacat   480
caccaaaact cctcttcctt tgcactggcc actcagtaca tgtctgtttg ggaattgttt   540
agtttagggt ttttcgatat gatgaatgtc acgttgctag ctgtcaccc attaacgaca   600 ttaacatttc atgttgtcaa tatctggttg tcagttgagg atcatagtgg ctacaacttc   660
ccatggtcta cgcacagatt agtaccattc ggttggtatg gtggtgttgt acatcatgac   720
ttgcatcact ctcatttcaa ttgtaacttt gctccttact tcacacattg ggataagatc   780
ctaggaactc tgagaacagc ctcagtacct gcaaggtaat ga                       822

<210> SEQ ID NO 20
<211> LENGTH: 822
<212> TYPE: DNA
<213> ORGANISM: Artificial Sequence
<220> FEATURE:
<223> OTHER INFORMATION: codon optimized chimpanzee cholesterol
      25-hydroxylase gene

<400> SEQUENCE: 20

| | |
|---|---:|
| atgtcttgtc acaactgttc tgatccacaa gttttgtgtt cttctggtca attgttcttg | 60 |
| caaccattgt gggatcactt gagatcatgg gaagccttgt tgcaatctcc attcttccca | 120 |
| gttattttct ctattactac ttacgttggt ttctgtttgc cattcgttgt tttggatatt | 180 |
| ttgtgttctt gggttccagc tttgagaaga tacaagattc acccagattt ctctccatct | 240 |
| gctagacaat tgttgccatg tttgggtcaa actttgtacc aacacgttat gttcgttttc | 300 |
| ccagttactt tgttgcactg gctagatccc cagctttgt tgccacacga agctccagaa | 360 |
| ttgttgttgt tgttgcacca catttgttc tgtttgttgt tgttcgatat ggagttcttc | 420 |
| gtttggcact tgttgcacca caaggttcca tggttgtaca gaactttcca caaggttcac | 480 |
| caccaaaact cttcttcttt cgctttggct actcaataca tgtctgtttg ggaattgttc | 540 |
| tctttgggtt tcttcgatat gatgaacgtt actttgttgg ttgtcaccc attgactact | 600 |
| ttgactttcc acgttgttaa catttggttg tctgttgaag atcactctgg ttacaacttc | 660 |
| ccatggtcta ctcacagatt ggttccattc ggttggtacg tggtgttgt tcaccacgat | 720 |
| ttgcaccact ctcacttcaa ctgtaacttc gctccatact tcactcactg ggataagatt | 780 |
| ttgggtactt tgagaactgc ttctgttcca gctagataat ga | 822 |

<210> SEQ ID NO 21
<211> LENGTH: 298
<212> TYPE: PRT
<213> ORGANISM: Rattus norvegicus

<400> SEQUENCE: 21

Met Ala Cys His Asn Val Ser Glu Leu Gln Asp Leu Gly Cys Ser Asn
1               5                   10                  15

Gln Leu Leu Leu Gln Pro Leu Trp Asp Ser Ile Arg Thr Gly Glu Ala
                20                  25                  30

Ser Ala Arg Ser Pro Phe Phe Pro Val Ile Phe Ser Ile Phe Thr Tyr
            35                  40                  45

Leu Gly Phe Cys Leu Pro Phe Val Val Leu Asp Val Leu Cys Pro Trp
        50                  55                  60

Val Pro Ile Leu Arg Arg Tyr Lys Ile His Pro Asp Phe Ser Pro Ser
65                  70                  75                  80

Val Arg Gln Leu Leu Pro Cys Leu Gly Leu Thr Leu Tyr Gln His Leu
                85                  90                  95

Val Phe Val Phe Pro Val Thr Leu Met His Trp Ala Arg Ser Pro Ala
            100                 105                 110

Leu Leu Pro Arg Glu Ala Pro Glu Leu Ser Gln Leu Leu Ser His Val
        115                 120                 125

Leu Ile Cys Leu Leu Leu Phe Asp Thr Glu Ile Phe Ala Trp His Leu
    130                 135                 140

Leu His His Lys Val Pro Trp Leu Tyr Arg Thr Phe His Lys Val His
145                 150                 155                 160

His Gln Asn Ser Ser Ser Phe Ala Leu Ala Thr Gln Tyr Met Ser Val
                165                 170                 175

Trp Glu Leu Leu Ser Leu Thr Phe Phe Asp Val Leu Asn Val Ala Met
            180                 185                 190

Leu Gln Cys His Pro Leu Thr Ile Leu Val Phe His Val Asn Ile
        195                 200                 205

Trp Leu Ser Val Glu Asp His Ser Gly Tyr Asp Phe Pro Trp Ser Thr
    210                 215                 220

His Arg Leu Val Pro Phe Gly Trp Tyr Gly Gly Val Ala His His Asp
225                 230                 235                 240

Leu His His Ser Gln Phe Asn Cys Asn Phe Ala Pro Tyr Phe Thr His
            245                 250                 255

Trp Asp Lys Met Leu Gly Thr Leu Arg Cys Ala Pro Ser Lys Arg
        260                 265                 270

Leu Cys Ala Gly Ser Glu Ser Cys Leu Asp Ser Gly Glu Gln Cys Thr
            275                 280                 285

Val His Leu Asn Gln Lys Lys Lys Gln Thr
    290                 295

<210> SEQ ID NO 22
<211> LENGTH: 903
<212> TYPE: DNA
<213> ORGANISM: Artificial Sequence
<220> FEATURE:
<223> OTHER INFORMATION: codon optimized rat cholesterol 25-hydroxylase
      gene

<400> SEQUENCE: 22
atggcttgtc ataatgtttc agaattgcag gatttgggtt gtagtaacca attactacta      60
caaccacttt gggactctat cagaactggc gaagcatctg ctcgttctcc attcttccct     120
gtcattttct ccattttcac ttacttaggc ttttgtctgc catttgtagt cttggatgta     180 cttgtccat gggttcctat acttagaaga tacaagatcc atcctgactt ctcaccatcc      240
gtcaggcagt tgctaccttg cttgggtcta acattgtatc agcacctagt gttcgttttt     300
ccagtcacat tgatgcactg ggctagatca ccagccctgc tacctagaga agcaccagag     360
ttatctcaat tactgtccca tgtactgata tgcttgttgt tgtttgacac tgaaatcttt     420
gcttggcatc ttttacacca caaagttcct tggttataca gaaccttcca taaggtgcat     480
caccaaaact catcttcatt tgctttagcc actcaataca tgagtgtgtg ggagctgtta     540
tcattaacct ttttcgatgt ccttaatgtt gccatgcttc aatgtcaccc tttgacaatt     600
ctggtttttc atgttgtcaa catctggttg tctgtagaag atcactctgg atatgatttc     660
ccatggtcta ctcataggtt agttcctttc ggttggtacg ggggtgtagc acatcatgat     720
ctgcatcata gtcaattcaa ctgcaatttc gcaccatact tcacacattg ggataagatg     780
ctagggactc taagatgtgc cccacactcc aagagacttt gtgctggatc agaatcttgc     840
ctagatagtg gtgaacaatg tacagtgcac ttgaaccaga aaagaaaca aacatgataa      900 tga                                                                   903

<210> SEQ ID NO 23
<211> LENGTH: 900
<212> TYPE: DNA
<213> ORGANISM: Artificial Sequence
<220> FEATURE:
<223> OTHER INFORMATION: codon optimized rat cholesterol 25-hydroxylase
      gene

<400> SEQUENCE: 23

```
atggcttgtc acaacgtttc tgaattgcaa gatttgggtt gttctaacca attgttgttg      60
caaccattgt gggattctat tagaactggt gaagcatctg ctagatcacc attcttccca     120
gttattttct ctattttcac ttacttgggt ttctgtttgc cattcgttgt tttggatgtt     180
ttgtgtccat gggttccaat tttgagaaga tacaagattc acccagattt ctctccatct     240
gttagacaat tgttgccatg tttgggtttg actttgtacc aacacttggt tttcgttttc     300
ccagttactt tgatgcactg ggctagatca ccagctttgt tgccaagaga agctccagaa     360
ttgtctcaat tgttgtctca cgttttgatt tgtttgttgt tgttcgatac tgaaattttc     420
gcttggcact tgttgcacca caaggttcca tggttgtaca gaactttcca caaggttcac     480
caccaaaact cttcttcttt cgctttggct actcaataca tgtctgtttg ggaattgttg     540
tctttgactt tcttcgatgt tttgaacgtt gctatgttgc aatgtcaccc attgactatt     600
ttggttttcc acgttgttaa catttggttg tctgttgaag atcactctgg ttacgatttc     660
ccatggtcta ctcacagatt ggttccattc ggttggtacg tggtgttgc tcaccacgat     720 ttgcaccact ctcaattcaa ctgtaacttc gctccatact tcactcactg gataagatg     780 ttgggtactt tgagatgtgc tccacactct aagagattgt gtgctggttc tgaatcttgt     840
ttggattctg gtgaacaatg tactgttcac ttgaaccaaa agaagaagca aacttaatga     900
```

<210> SEQ ID NO 24
<211> LENGTH: 270
<212> TYPE: PRT
<213> ORGANISM: Equus caballus

<400> SEQUENCE: 24

```
Met Ser Gly His Asn Ser Ser Glu Leu His Val Leu Cys Ser Ser Gly
1               5                   10                  15

Gln Leu Phe Leu Gln Pro Leu Trp Asp Ser Leu Arg Thr Arg Glu Ala
            20                  25                  30

Leu Thr His Ser Pro Phe Phe Pro Val Ile Phe Ser Ile Ala Thr Tyr
        35                  40                  45

Val Gly Phe Cys Leu Pro Phe Val Val Leu Asp Leu Leu Cys Pro Trp
    50                  55                  60

Val Pro Ala Leu Arg Arg Tyr Lys Ile His Pro Asp Phe Leu Pro Ser
65                  70                  75                  80

Ala Arg Gln Val Leu Pro Cys Leu Gly Gln Thr Leu Tyr Gln His Leu
                85                  90                  95

Val Phe Val Phe Pro Ala Thr Leu Leu Leu Trp Ala Arg Gly Pro Val
            100                 105                 110

Phe Leu Pro Leu Glu Ala Pro Glu Leu Leu Gln Leu Ala Phe His Val
        115                 120                 125

Val Phe Cys Leu Leu Leu Phe Asp Thr Glu Phe Leu Trp His Val
    130                 135                 140

Leu His His Lys Val Pro Trp Leu Tyr Arg Thr Phe His Lys Met His
145                 150                 155                 160

His Gln Asn Ser Ser Ser Phe Ala Leu Ala Thr Gln Tyr Met Ser Ile
                165                 170                 175

Trp Glu Leu Phe Ser Leu Val Phe Phe Asp Ile Met Asn Val Thr Leu
            180                 185                 190

Leu Glu Cys His Pro Leu Thr Ile Leu Val Phe His Val Val Asn Ile
        195                 200                 205

Trp Leu Ser Val Glu Asp His Ser Gly Tyr Asp Phe Pro Trp Ser Thr
    210                 215                 220
```

His Arg Leu Val Pro Phe Gly Trp Tyr Gly Gly Val Ala His His Asp
225                 230                 235                 240

Leu His His Ser Gln Phe Asn Cys Asn Phe Ala Pro Tyr Phe Thr His
            245                 250                 255

Trp Asp Lys Ile Leu Gly Thr Leu Arg Ser Ala His Ala Lys
        260                 265                 270

<210> SEQ ID NO 25
<211> LENGTH: 816
<212> TYPE: DNA
<213> ORGANISM: Artificial Sequence
<220> FEATURE:
<223> OTHER INFORMATION: codon optimized horse cholesterol
      25-hydroxylase gene

<400> SEQUENCE: 25

```
atgtccggcc ataactcatc agaacttcat gttttgtgtt cctctggcca attgttccta      60
caacctttgt gggattcact gagaactaga gaggctctta cacactcccc attcttccca     120
gtaatcttct caatcgcaac ttacgttgga ttttgtttgc catttgttgt ccttgacttg     180
ttatgccctt gggtgccagc ccttagaaga tacaagatac atcctgattt ctgccaagt      240
gccagacagg tcttgccatg cttaggtcaa acccttacc  aacatctagt gttcgtattc     300
cctgcaacac tattgctatg gctagaggg  ccagtatttc tgcctttaga agccccctgaa    360
ctattacaat tagcattcca tgtcgtcttt tgtctgttgt tattcgatac cgagttttc      420
ctgtggcatg ttttacatca taaagtacca tggttatacc gtacatttca caaaatgcac     480
catcaaaaca gttcctcttt cgcccttgct actcagtata tgtctatctg ggaactgttt     540
agtctagtct ttttcgacat tatgaacgtt acattgttgg aatgtcaccc attgacaata     600
cttgtttttc atgttgtgaa tatctggctt tctgttgaag atcactctgg ttacgatttc     660
ccttggtcaa cacataggtt agttccattc ggatggtatg gtggagtggc tcaccatgat     720
ttgcatcact cacaattcaa ttgcaatttc gcaccatact tcactcactg ggataagatt     780
ttgggtacac taaggtctgc acacgctaag taatga                               816
```

<210> SEQ ID NO 26
<211> LENGTH: 816
<212> TYPE: DNA
<213> ORGANISM: Artificial Sequence
<220> FEATURE:
<223> OTHER INFORMATION: codon optimized horse cholesterol
      25-hydroxylase gene

<400> SEQUENCE: 26

```
atgtctggtc acaactcttc tgaattgcac gttttgtgtt cttctggtca attgttcttg      60
caaccattgt gggattcttt gagaactaga gaggctttga ctcactctcc attcttccca     120
gttattttct ctattgctac ttacgttggt ttctgtttgc cattcgttgt tttggatttg     180
ttgtgtccat gggttccagc tttgagaaga tacaagattc acccagattt cttgccatct     240
gctagacaag tttttgccatg tttgggtcaa acttttgtacc aacacttggt tttcgttttc     300
ccagctactt tgttgttgtg ggctagaggt ccagttttct tgccattgga agctccagaa     360
ttgttgcaat ggctttccca cgttgttttc tgttttgtgt gttcgatac tgaattttc      420
ttgtggcacg ttttgcacca caaggttcca tggttgtaca gaactttcca caagatgcac     480
caccaaaact cttcttcttt cgctttggct actcaataca tgtctatttg ggaattgttc     540
tcttttggttt tcttcgatat tatgaacgtt actttgttgg aatgtcaccc attgactatt     600
```
ttggttttcc acgttgttaa catttggttg tctgttgaag atcactctgg ttacgatttc 660
ccatggtcta ctcacagatt ggttccattc ggttggtacg gtggtgttgc tcaccacgat 720
ttgcaccact ctcaattcaa ctgtaacttc gctccatact tcactcactg ggataagatt 780
ttgggtactt tgagatcagc tcacgctaag taatga 816

<210> SEQ ID NO 27
<211> LENGTH: 816
<212> TYPE: DNA
<213> ORGANISM: Artificial Sequence
<220> FEATURE:
<223> OTHER INFORMATION: codon optimized pig cholesterol 25-hydroxylase gene

<400> SEQUENCE: 27
atgtctggtc ataacaattc tgagctatta gttctatgtt ctagtggaca gttgttcctt 60
cagccattat gggatcattt gaaaacctgg gaaactttga ttcaatcacc attcttccca 120
gtctttttct caataacaac ttatctgggt ttctgtttac ctttcgtagt gctagatgtt 180
ctatgtcctt gggtgccagc acttagaaga tacaagatcc accctgactt ctcaccatcc 240
gtttggcaac tacttccatg tttaggatta accctttacc aacatgttgt ttttgttttt 300
ccaatgacac tattacactg ggctgcttca cctgtcttac tacctcctga agctcctgag 360
ttactgcaat tagtgagaca tatagttttg tgcttgcttc tgttcgatac tgagtttttc 420
atttggcatg tcttgcatca caaagtacca tggttgtata ggacatttca taagatgcac 480
catcagaaca gttcctcttt cgccctggcc actcaataca tgtcagtcgg cgaactgttg 540
tctttgggtg tatttgatat ggttaacatc atgctactac gttgtcatcc acttacagtg 600
ttgatctttc atgtcattaa catctggctt tcagtagaag atcatagtgg atacgacttt 660
ccatggtcta ctcacagact ggttccattc ggttggtacg gaggtgtaac acaccacgat 720
ttgcatcact ctcaattcaa ttgcaatttc gctccatact tcacacattg ggataagata 780
ttgggcacat taagatccgc acacgcaaag taatga 816

<210> SEQ ID NO 28
<211> LENGTH: 816
<212> TYPE: DNA
<213> ORGANISM: Artificial Sequence
<220> FEATURE:
<223> OTHER INFORMATION: codon optimized pig cholesterol 25-hydroxylase gene

<400> SEQUENCE: 28
atgtctggtc acaacaactc tgaattgttc gttttgtgtt cttcttctca attgttcttg 60
caaccattgt gggatcactt gaagacttgg gaaactttga ttttgtctcc attcttccca 120
gttttcttct ctattactac ttacttgggt ttctgtttgc cattcgttgt tttggatgtt 180
ttgtgtccat gggttccagc tttgagaaga tacaagattc acccagattt ctctccatct 240
gtttggcaat tgttgccatg tttgggtttg actttgtacc aacacgttgt tttcgttttc 300
ccaatgactt tgttgcactg ggctgcttct ccagttttgt tgccaccaga agctccagaa 360
ttgttgcaat tggttagaca cattgttttg tgtttgttgt tgttcgatac tgagttcttc 420
atttggcacg ttttgcacca caaggttcca tggttgtaca gaactttcca caagatgcac 480
caccaaaact cttcttcttt cgctttggct actcaataca tgtctgttgg tgaattgttg 540
tctttgggtg ttttcgatat ggttaacatt atgttgttga gatgtcaccc attgactgtt 600


```
ttgattttcc acgttattaa catttggttg tctgttgaag atcactctgg ttacgatttc      660
ccatggtctg ctcacagatt ggttccattc ggttggtacg gtggtgttac tcaccacgat      720
ttgcaccact ctcaattcaa ctgtaacttc gctccatact tcactcactg ggataagatt      780
ttgggtactt tgagatcagc tcacgctaag taatga                                816
```

<210> SEQ ID NO 29
<211> LENGTH: 270
<212> TYPE: PRT
<213> ORGANISM: Artificial Sequence
<220> FEATURE:
<223> OTHER INFORMATION: Consensus amino acid sequence of cholesterol
      25-hydroxylase

<400> SEQUENCE: 29

```
Met Ser Cys His Asn Ser Ser Glu Leu Gln Val Leu Cys Ser Ser Gly
1               5                   10                  15

Gln Leu Phe Leu Gln Pro Leu Trp Asp His Leu Arg Thr Trp Glu Ala
            20                  25                  30

Leu Ile Gln Ser Pro Phe Phe Pro Val Ile Phe Ser Ile Thr Thr Tyr
        35                  40                  45

Val Gly Phe Cys Leu Pro Phe Val Val Leu Asp Val Leu Cys Pro Trp
    50                  55                  60

Val Pro Ala Leu Arg Arg Tyr Lys Ile His Pro Asp Phe Ser Pro Ser
65                  70                  75                  80

Ala Arg Gln Leu Leu Pro Cys Leu Gly Gln Thr Leu Tyr Gln His Val
                85                  90                  95

Val Phe Val Phe Pro Val Thr Leu Leu His Trp Ala Arg Ser Pro Ala
            100                 105                 110

Leu Leu Pro Arg Glu Ala Pro Glu Leu Leu Gln Leu Leu Ser His Val
        115                 120                 125

Leu Phe Cys Leu Leu Leu Phe Asp Thr Glu Phe Phe Val Trp His Leu
    130                 135                 140

Leu His His Lys Val Pro Trp Leu Tyr Arg Thr Phe His Lys Val His
145                 150                 155                 160

His Gln Asn Ser Ser Ser Phe Ala Leu Ala Thr Gln Tyr Met Ser Val
                165                 170                 175

Trp Glu Leu Leu Ser Leu Gly Phe Phe Asp Met Leu Asn Val Thr Leu
            180                 185                 190

Leu Gln Cys His Pro Leu Thr Val Leu Thr Phe His Val Val Asn Ile
        195                 200                 205

Trp Leu Ser Val Glu Asp His Ser Gly Tyr Asp Phe Pro Trp Ser Thr
    210                 215                 220

His Arg Leu Val Pro Phe Gly Trp Tyr Gly Val Ala His His Asp
225                 230                 235                 240

Leu His His Ser Gln Phe Asn Cys Asn Phe Ala Pro Tyr Phe Thr His
                245                 250                 255

Trp Asp Lys Ile Leu Gly Thr Leu Arg Ser Ala His Ala Lys
            260                 265                 270
```

<210> SEQ ID NO 30
<211> LENGTH: 813
<212> TYPE: DNA
<213> ORGANISM: Artificial Sequence
<220> FEATURE:
<223> OTHER INFORMATION: nucleotide sequence encoding the consensus
      amino acid sequence of cholesterol 25-hydroxylase of SEQ ID NO:29

<400> SEQUENCE: 30

```
atgtcttgcc acaattcctc tgagcttcaa gtattgtgtt catcaggtca gttgttttg     60
caaccattat gggatcactt aaggacgtgg gaagccctga ttcaaagtcc tttcttccct    120
gtgatattct ccataactac ttacgtgggc ttttgtttac catttgttgt tttggatgtt    180
ctatgcccat gggttccagc tctgagaaga tacaagattc atccagattt ctccccttca    240
gccagacaat tgttaccatg tttggggcaa acactatatc agcatgtggt ctttgttttc    300
cctgtgactc tattacattg gccagaagt cctgctttgc tgcctagaga agcccctgaa    360
ctgttgcagt tattgtctca cgtcttattc tgtttgctgc ttttcgatac agagtttttc    420
gtttggcatc tacttcatca taaagttcca tggctgtata gaacgttcca caaagtccac    480
caccagaact ctagttcatt cgcattggcc acccaataca tgtccgtatg gaactgcta    540
tctttaggct ttttcgatat gcttaatgtc actcttttgc aatgtcatcc tttgacagtg    600
ctaacattcc atgtagtgaa catctggtta tctgtagaag atcacagtgg atatgatttt    660
ccttggtcta ctcacaggtt ggttccattt ggatggtatg tggtgtagc tcatcacgac    720
ctgcatcatt cacaattcaa ttgcaacttt gctccatact ttacacattg gacaaaatc    780
ttgggaacat taaggtctgc tcatgcaaag tga                                813
```

<210> SEQ ID NO 31
<211> LENGTH: 816
<212> TYPE: DNA
<213> ORGANISM: Artificial Sequence
<220> FEATURE:
<223> OTHER INFORMATION: nucleotide sequence encoding the consensus
      amino acid sequence of cholesterol 25-hydroxylase of SEQ ID NO:29

<400> SEQUENCE: 31

```
atgtcttgtc acaactcttc tgaattgcaa gttttgtgtt cttctggtca attgttcttg     60
caaccattgt gggatcactt gagaacttgg gaagcattga ttcaatctcc attcttccca    120
gttattttct ctattactac ttacgttggt ttctgtttgc cattcgttgt tttggatgtt    180
ttgtgtccat gggttccagc tttgagaaga tacaagattc acccagattt ctctccatct    240
gctagacaat tgttgccatg tttgggtcaa actttgtacc aacacgttgt tttcgttttc    300
ccagttactt tgttgcactg gctagatca ccagctttgt tgccaagaga agctccagaa    360
ttgttgcaat tgttgtctca cgttttgttc tgtttgttgt tgttcgatac tgaattttc     420
gtttggcact tgttgcacca caaggttcca tggttgtaca gaactttcca caaggttcac    480
caccaaaact cttcttcttt cgctttggct actcaataca tgtctgtttg gaattgttg    540
tctttgggtt tcttcgatat gttgaacgtt actttgttgc aatgtcaccc attgactgtt    600
ttgactttcc acgttgttaa catttggttg tctgttgaag atcactctgg ttacgatttc    660
ccatggtcta ctcacagatt ggttccattc ggttggtacg tggtgttgc tcaccacgat    720
ttgcaccact ctcaattcaa ctgtaacttc gctccatact cactcactg ggataagatt    780
ttgggtactt tgagatcagc tcacgctaag taatga                              816
```

<210> SEQ ID NO 32
<211> LENGTH: 3219
<212> TYPE: DNA
<213> ORGANISM: Artificial Sequence
<220> FEATURE:
<223> OTHER INFORMATION: DNA sequence of ERG6 integration construct

<400> SEQUENCE: 32

```
gtcgacgttt tactttcgat ttaagtttta cataatttaa aaaaacaaga ataaaataat    60
aatatagtag gcagcataag atgagtgaaa cagaattgag aaaaagacag gcccaattca   120
ctagggagtt acatggtgat gatattggta aaaagacagg tttgagtgca ttgatgtcga   180
agaacaactc tgcccaaaag gaagccgttc agaagtactt gagaaattgg gatggtagaa   240
ccgataaaga tgccgaagaa cgtcgtcttg aggattataa tgaagccaca cattcctact   300
ataacgtcgt tacagatttc tatgaatatg gttgaggttc ctctttccat ttcagcagat   360
tttataaagg tgagagtttc gctgcctcga tagcaagaca tgaacattat ttagcttaca   420
aggctggtat tcaaagaggc gatttagttc tcgacgttgg ttgtggtgtt gggggcccag   480
caagagagat tgcaagattt accggtgcca tttcaaagaa tacgtaaata attaatagta   540
gtgattttcc taactttatt tagtcaaaaa attagccttt taattctgct gtaacccgta   600
catgcccaaa ataggggcg gttacacag aatatataac atcgtaggtg tctgggtgaa    660
cagtttattc ctggcatcca ctaaatataa tggagcccgc ttttaagct ggcatccaga    720 aaaaaaaga tcccagcac caaaatattg ttttcttcac caaccatcag ttcataggtc     780
cattctctta gcgcaactac agagaacagg ggcacaaaca ggcaaaaaac gggcacaacc   840
tcaatggagt gatgcaacct gcctggagta atgatgaca caaggcaatt gacccacgca    900
tgtatctatc tcattttctt acaccttcta ttaccttctg ctctctctga tttggaaaaa   960
gctgaaaaaa aaggttgaaa ccagttccct gaaattattc ccctacttga ctaataagta  1020
tataaagacg gtaggtattg attgtaattc tgtaaatcta tttcttaaac ttcttaaatt  1080
ctacttttat agttagtctt tttttagtt ttaaaacacc aagaacttag tttcgaataa   1140
acacacataa ggatccatta ttatttgaat tcgcggggga tctcccatgt ctctactggt  1200
ggtggtgctt ctttggaatt attggaaggt aaggaattgc caggtgttgc tttcttatcc  1260
gaaaagaaat aaattgaatt gaattgaaat cgtagatcaa ttttttttctt ttctctttcc  1320 ccatccttta cgctaaaata atagtttatt ttattttttg aatatttttt atttatatac   1380
gtatatatag actattattt atcttttaat gattattaag attttttatta aaaaaaaatt  1440 cgctcctctt ttaatgcctt tatgcagttt ttttttccca ttcgatattt ctatgttcgg  1500
gttcagcgta ttttaagttt aataactcga aaattctgcg ttcgaaagct tttcaattca  1560 tcttttttt ttttgttctt tttttgatt ccggtttctt tgaaattttt ttgattcggt   1620
aatctccgag cagaaggaag aacgaaggaa ggagcacaga cttagattgg tatatatacg  1680
catatgtggt gttgaagaaa catgaaattg cccagtattc ttaacccaac tgcacagaac  1740
aaaaacctgc aggaaacgaa gataaatcat gtcgaaagct acatataagg aacgtgctgc  1800
tactcatcct agtcctgttg ctgccaagct atttaatatc atgcacgaaa agcaaacaaa  1860
cttgtgtgct tcattggatg ttcgtaccac caaggaatta ctggagttag ttgaagcatt  1920
aggtcccaaa atttgtttac taaaaacaca tgtggacatc ttgactgatt tttccatgga  1980
gggcacagtt aagccgctaa aggcattatc cgccaagtac aatttttttac tcttcgaaga  2040 cagaaaattt gctgacattg gtaatacagt caaattgcag tactctgcgg gtgtatacag  2100
aatagcagaa tgggcagaca ttacgaatgc acacggtgtg gtgggcccag gtattgttag  2160
cggtttgaag caggcggcgg aagaagtaac aaaggaacct agaggccttt tgatgttagc  2220
agaattgtca tgcaagggct ccctagctac tggagaatat actaagggta ctgttgacat  2280
tgcgaagagc gacaaagatt ttgttatcgg ctttattgct caaagagaca tgggtggaag  2340
agatgaaggt tacgattggt tgattatgac acccggtgtg ggtttagatg acaagggaga  2400
```

```
cgcattgggt caacagtata gaaccgtgga tgatgtggtc tctacaggat ctgacattat    2460
tattgttgga agaggactat ttgcaaaggg aagggatgct aaggtagagg gtgaacgtta    2520
cagaaaagca ggctgggaag catatttgag aagatgcggc cagcaaaact aaaaaactgt    2580
attataagta aatgcatgta tactaaactc acaaattaga gcttcaattt aattatatca    2640
gttattaccc gggaatctcg gtcgtaatga tttctataat gacgaaaaaa aaaaaattgg    2700
aaagaaaaag cttattcact agatcaataa gattcaaata aagcgcacga tatataccta    2760
ttttcctata tatgcagata aaaagatagc acgttcattg ctagcaggcc ttacaaacag    2820
actgtccgat gcctttacta ccccacaatt tatcccactt gtgattttca agttcggctt    2880 ttttttttt catcatgtcg tggcaaacga ccagtatttt ctatcagaat aagaaaaaac     2940
tataattcac tgcatacaaa cgtattgact gctccctac agcggaagat agtaagaata    3000
caacatcgta actgtttcca tatttatgtg ccgatatggt aaaagtgaaa tctaagaata    3060
gtgttataaa gctattgtct acagcggcaa gtggatactc tcgttacatc tcgattaaga    3120
aaggtgcacc tttggttact caggtcagat acgatcctgt ggtgaaacgg catgtgcttt    3180
tcaaagaagc aaagaaaagg aaagtggcag aaagtcgac                          3219
```

US 9,624,521 B2

PRODUCTION OF NON-YEAST STEROLS BY YEAST

This application is the U.S. national phase of International Application No. PCT/EP2010/068127 filed 24 Nov. 2010 which designated the U.S. and claims priority to EP Patent Application No. 09014988.1 filed 3 Dec. 2009, the entire contents of each of which are hereby incorporated by reference.

FIELD OF THE INVENTION

This invention relates to the production of sterols, including 7-dehydrocholesterol, 25-hydroxy-7-dehydrocholesterol, and 25-hydroxy ergosterol in yeast such as *Saccharomyces cerevisiae*. It also related to various enzymes catalyzing the reduction of the double bond at position 24 of zymosterol, cholesta-7,24-dienol and cholesta-5,7,24-trienol; or the hydroxylation at position 25 of ergosterol, 7-dehydrocholesterol, cholesta-8-enol, and cholesta-7-enol. It also relates to various nucleic acids encoding cholesterol C25-hydroxylases and sterol Δ24-reductases and their use to produce and hydroxylate 7-dehydrocholesterol or ergosterol. It also relates to the yeast strains so produced, and methods of making these sterols comprising the steps of cultivation a transformed yeast cell, and harvesting the resulting sterol(s).

BACKGROUND OF THE INVENTION

The sterol pathway in yeasts involves many steps. A diagram of the yeast sterol pathway is presented as FIG. 14, and reference is made to it discussing prior art, below.

U.S. Pat. No. 5,460,949 (Amoco) teaches a method and composition for increasing the accumulation of squalene and trienol in yeast. This method includes truncation and overexpression of HMG1 (the single most important gene regulating the pathway) in a strain in which the genes ERG5 and ERG6 are inactivated. ERG5 and ERG6 encode the two enzymes activities that distinguish ergosterol, which is the major sterol of yeast and fungi, from cholesterol biosynthesis. These strains preferably accumulate cholesta-5,7,24-trienol, which is usually an intermediate of cholesterol biosynthesis.

WO03/064650 (Lang et al) (US2006/0240508) discloses a method for the production of 7-dehydrocholesterol and/or the biosynthetic intermediate or subsequent products in yeast. Here, the genes for the C-8 sterol isomerase, the C-5 sterol desaturase, and the sterol Δ24-reductase from mouse and human were expressed in a yeast strain in which ERG5 and ERG6 were inactivated and the HMG1 gene was truncated and overexpressed. These yeasts were able to synthesize 7-dehydrocholesterol.

WO03/064652 (Lang et al) (US2006/0088903) discloses a method for the production of zymosterol and/or the biosynthetic intermediate and/or subsequent products thereof in transgenic yeast by increasing lanosterol-C14-demethylase activity (ERG11).

WO 2005/121315 (Aventis) teaches cholesterol-producing yeast strains and uses thereof. A sterol Δ7 reductase gene from *Arabidopsis thaliana* and a human sterol Δ24-reductase gene were introduced into various yeast host strains in which ERG6 and, in some cases, ERG5 were inactivated. The new strains were able to produce cholesterol in admixture with other intermediates.

U.S. Pat. No. 6,562,609 (Russell et al) teaches an isolated human and mouse cholesterol C25-hydroxylase and genes.

The prior art is silent as to production of 25-hydroxyprovitamin D3 or 25-hydroxyprovitamin D2 using transgenic yeast.

DETAILED DESCRIPTION OF THE INVENTION

It has been found in accordance with this invention, that the enzyme cholesterol C25-hydroxylase (whose substrate is normally cholesterol) can act upon 7-dehydrocholesterol and ergosterol to produce 25-hydroxy-7-dehydrocholesterol and 25-hydroxyergosterol, respectively.

Thus, one aspect of this invention is the use of a vertebrate cholesterol C25-hydroxylase to hydroxylate 7-dehydrocholesterol or ergosterol in order to produce 25-hydroxy-7-dehydrocholesterol (also referred to as 25-hydroxyprovitamin D3) or 25-hydroxyergosterol (also referred to as 25-hydroxyprovitamin D2), respectively.

Cholesterol C25-hydroxylase is not an enzyme which naturally exists in yeast; in fact yeast normally do not have the ability to hydroxylate the side chain of 7-dehydrocholesterol, which can be present in yeast. However, in accordance with this invention, genetically modified yeast can be made to convert cholesta-5,7,24-trienol to 25-hydroxy-7-dehydrocholesterol (25-hydroxyprovitamin D3) by the process of:

providing the yeast with a nucleic acid encoding a cholesterol C25-hydroxylase and cultivating the yeast under conditions so that the yeast hydroxylates 7-dehydrocholesterol, whereby 25-hydroxy-7-dehydrocholesterol (25-hydroxyprovitamin D3) is produced.

In the above process, it is preferred that the yeast has had the genes ERG5 and ERG6 inactivated, and that it has also has been provided with a nucleic acid encoding a vertebrate sterol Δ24-reductase enzyme which has been optimized for expression in yeast.

It has been also found, in accordance with this invention that genetically modified yeast can be made to convert ergosterol to 25-hydroxyergosterol (also called 25-hydroxyprovitamin D2) by the process of:

providing the yeast with a nucleic acid encoding a cholesterol C25-hydroxylase and cultivating the yeast under conditions so that the yeast hydroxylates ergosterol, whereby 25-hydroxyergosterol (25-hydroxyprovitamin D2) is produced.

BRIEF DESCRIPTION OF THE FIGURES

In the following FIGURES, these abbreviations are used
TDH3p is the promoter region of TDH3 (glyceraldehyde-3-phosphate dehydrogenase isozyme 3 from *S. cerevisiae*);
Ori-pBR is the ColE1 replication origin from pBR322 for *E. coli*;
bla is the β-lactamase gene conferring resistance to ampicillin in *E. coli*;
2μ is the large fragment of the 2μ multi-copy vector carrying the replication origin for *S. cerevisiae*;
PGK1t is the terminator region of PGK1 (3-phosphoglycerate kinase from *S. cerevisiae*);
URA3 is the *S. cerevisiae* URA3 auxotrophy marker for uracil;
Bam HI, Eco RI, Hin dIII, Bgl II, Age I refer to the restriction sites of the corresponding restriction enzymes;
Localization of the sites on the vector are indicated in brackets starting from position 1 of the unique Bam HI site.

All HPLC profiles, recorded at UV 282 nm, were performed as described in Example 9 with sterol extracts made as described in Example 8. Abbreviations:
C5,7,22,24=cholesta 5,7,22,24-tetraenol;
C5,7,24=cholesta 5,7,24-trienol;
C5,7,22=cholesta 5,7,22-trienol;
C5,7=cholesta 5,7-dienol or 7-dehydrocholesterol;
25OH-C5,7-Ac=25-hydroxy 7-dehydrocholesterol acetate;
25OH-E5,7,22-Ac, 25-hydroxy ergosterol acetate;
E5,7,22,24, ergosta 5,7,22,24-tetraenol;
E5,7,22, ergosta 5,7,22-trienol (ergosterol).

Figure 6:
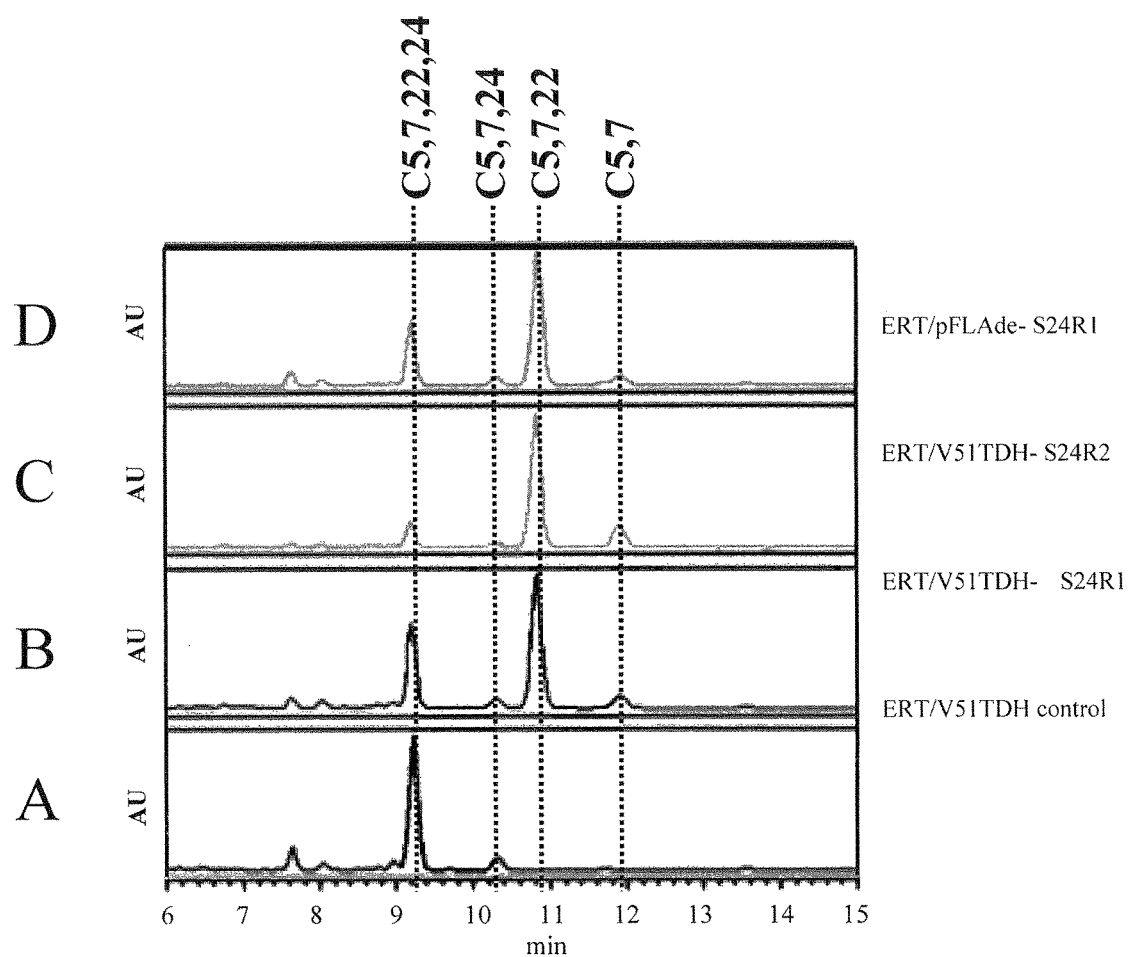

FIG. 6: HPLC elution profiles of sterol extracts from strains expressing a putative sterol C-24 sterol reductase. The following strains were used:
A: ERT/V51TDH control;
B: ERT/V51TDH-S24R1;
C: ERT/V51TDH-S24R2;
D: ERT/pFLAde-S24R1.

Figure 7:
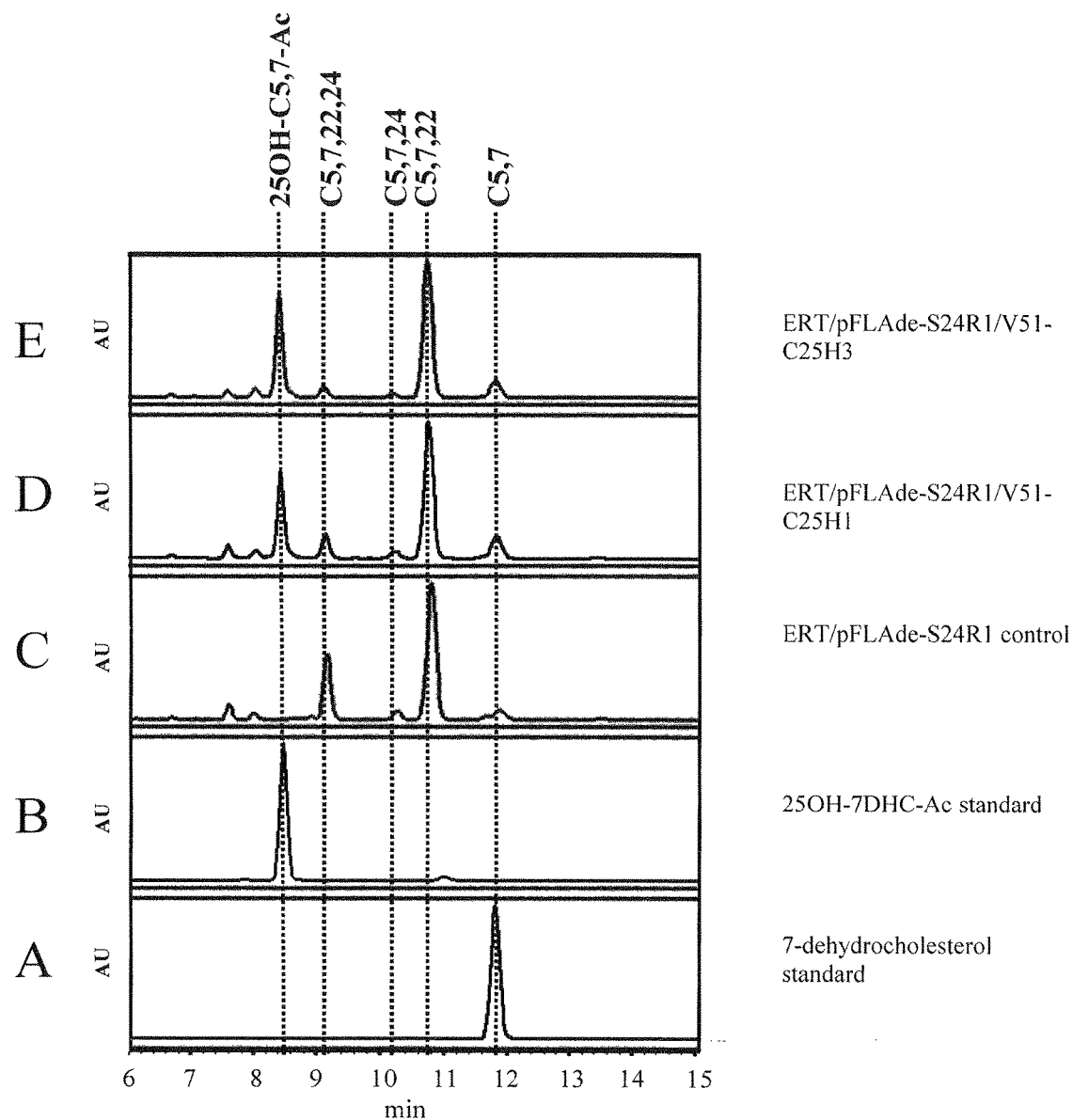

FIG. 7: HPLC elution profiles of sterol extracts from erg6 mutants expressing putative cholesterol C25-hydroxylases. The following strains were used:
C: ERT/pFLAde-S24R1N51;
D: ERT/pFLAde-S24R1N51-C25H1;
E: ERT/pFLAde-S24R1/V51-C25H3.

Standards were: A, cholesta 5,7-dienol (7-dehydrocholesterol, purchased from Sigma-Aldrich, St. Louis, Mo. 63103, USA); B, 25-hydroxy 7-dehydrocholesterol acetate (prepared as described in Example 9).

Figure 8:
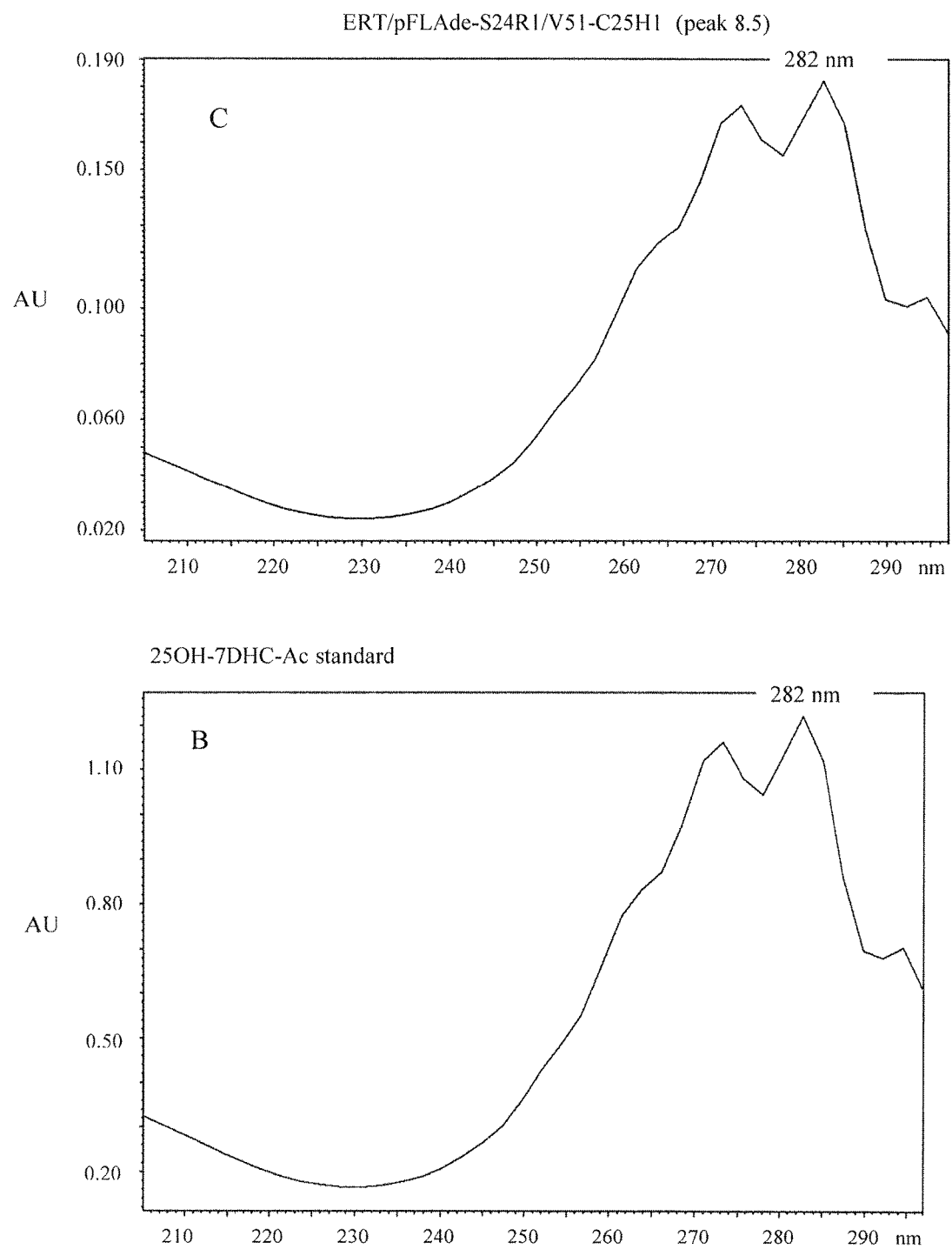
Figure 8:
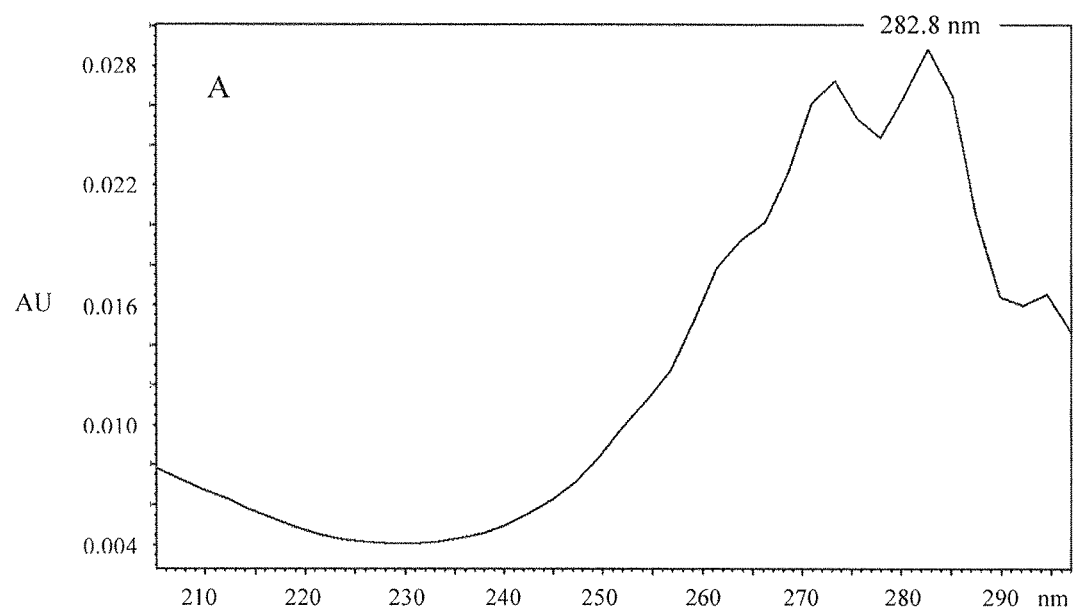

FIG. 8: UV spectra of single peaks from erg6 mutant strains expressing putative cholesterol C25-hydroxylases. UV spectra were determined on-line between 205 and 300 nm with the PDA detector during HPLC as described in Example 9 for the following peaks:
A: 7-dehydrocholesterol standard peak at 11.8 min (FIG. 7, profile A);
B: 25-hydroxy 7-dehydrocholesterol acetate standard peak at 8.5 min (FIG. 7, profile B);
C: ERT/pFLAde-S24R1N51-C25H1 peak at 8.5 min (FIG. 7, profile D).

Figure 9:
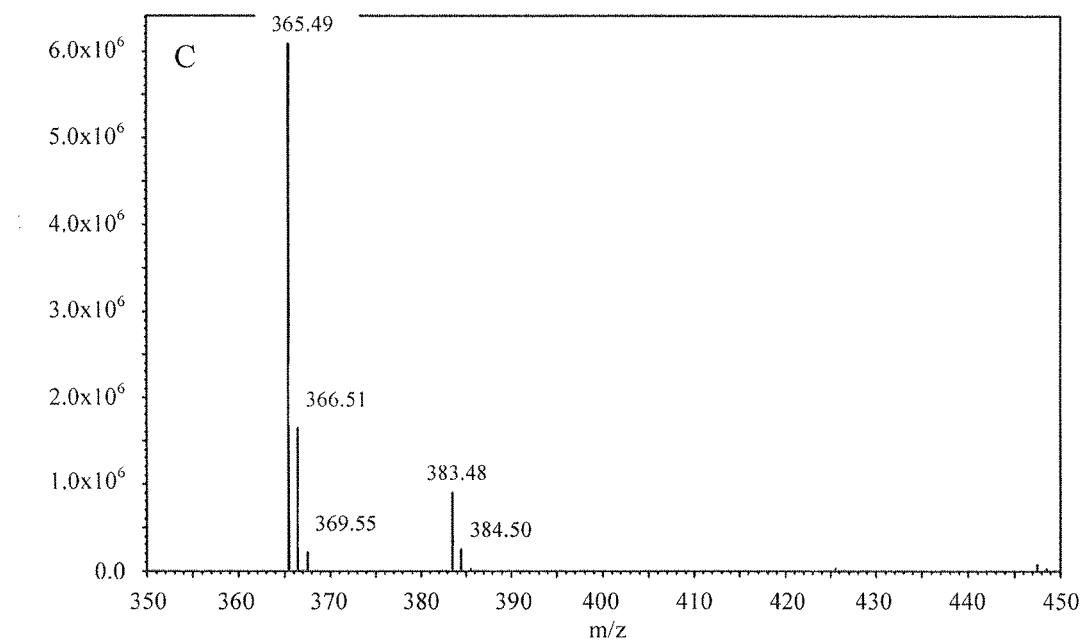
Figure 9:
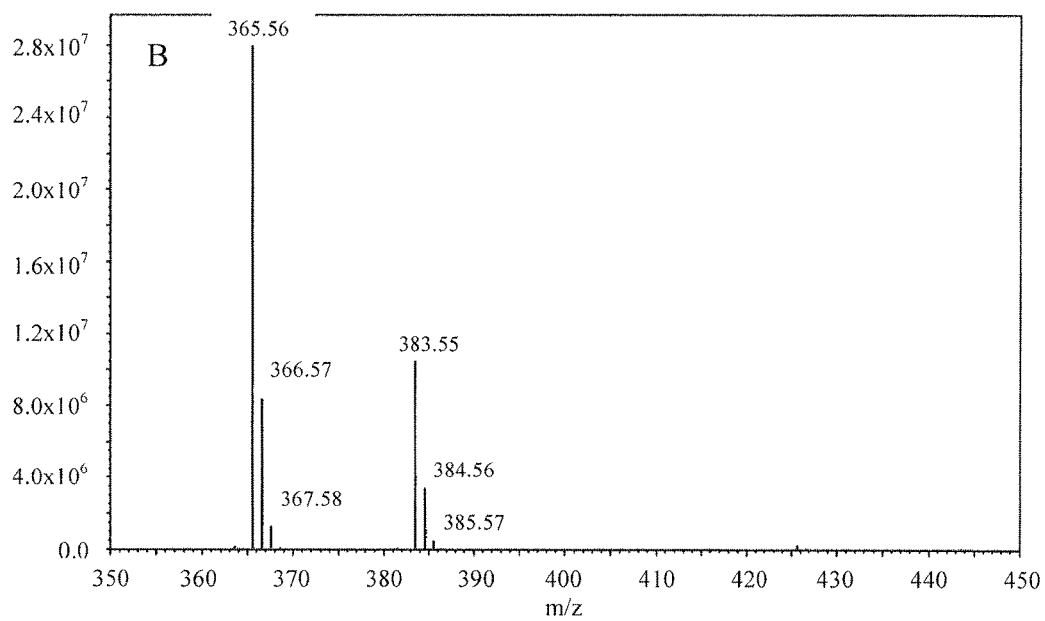
Figure 9:
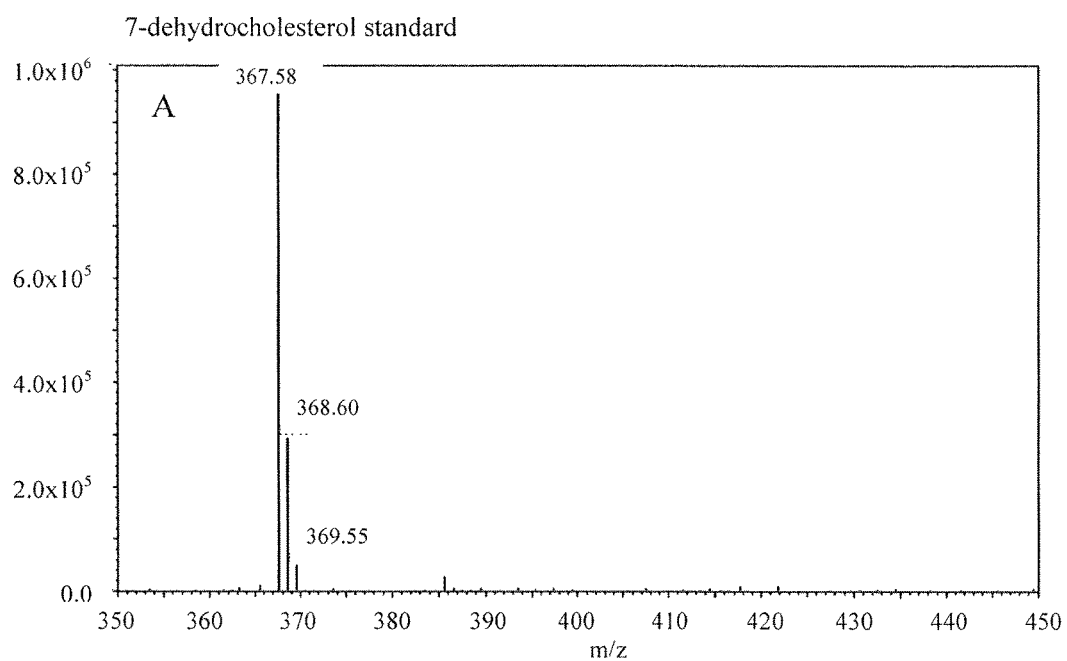

FIG. 9: Mass spectrometry profiles of single peaks from erg6 mutant strains expressing putative cholesterol C25-hydroxylases. The mass fragmentation profiles from m/z=350 to 450 were determined on-line with the Micro-Mass ZQ detector during HPLC as described in Example 9 on the following peaks:
A: 7-dehydrocholesterol standard peak at 11.8 min (FIG. 7, profile A);
B: 25-hydroxy 7-dehydrocholesterol acetate standard peak at 8.5 min (FIG. 7, profile B);
C: ERT/pFLAde-S24R1N51-C25H1 peak at 8.5 min (FIG. 7, profile D).

Figure 10:
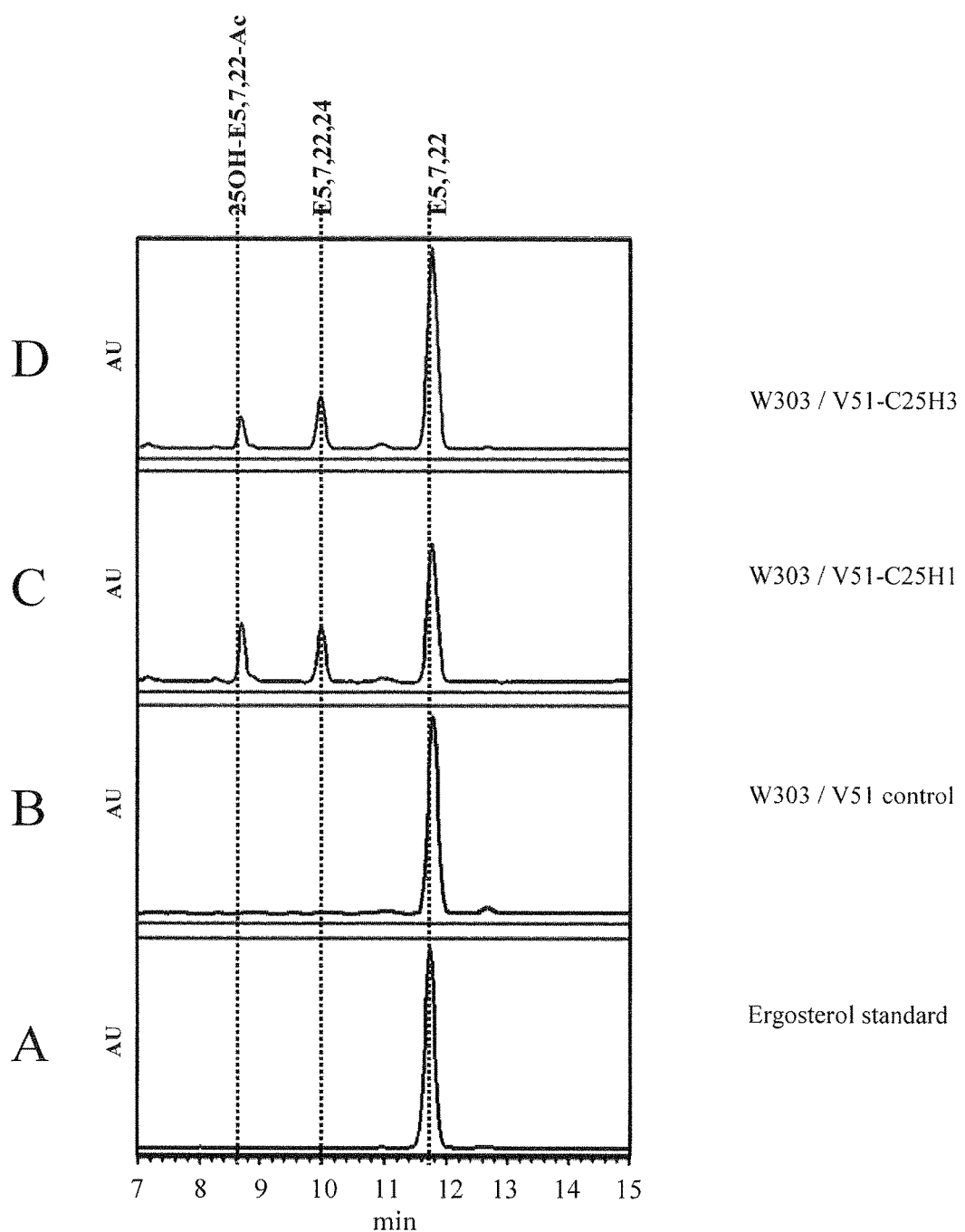

FIG. 10: HPLC elution profiles of sterol extracts from ERG6 wild type strains expressing putative cholesterol C25-hydroxylases. The following strains were used
B: W303 N51;
C: W303/V51-C25H1;
D: W303/V51-C25H3.

Standards were: A, ergosterol (ergosta 5,7,22-trienol) purchased from Sigma-Aldrich, St. Louis, Mo. 63103, USA.

Figure 11:
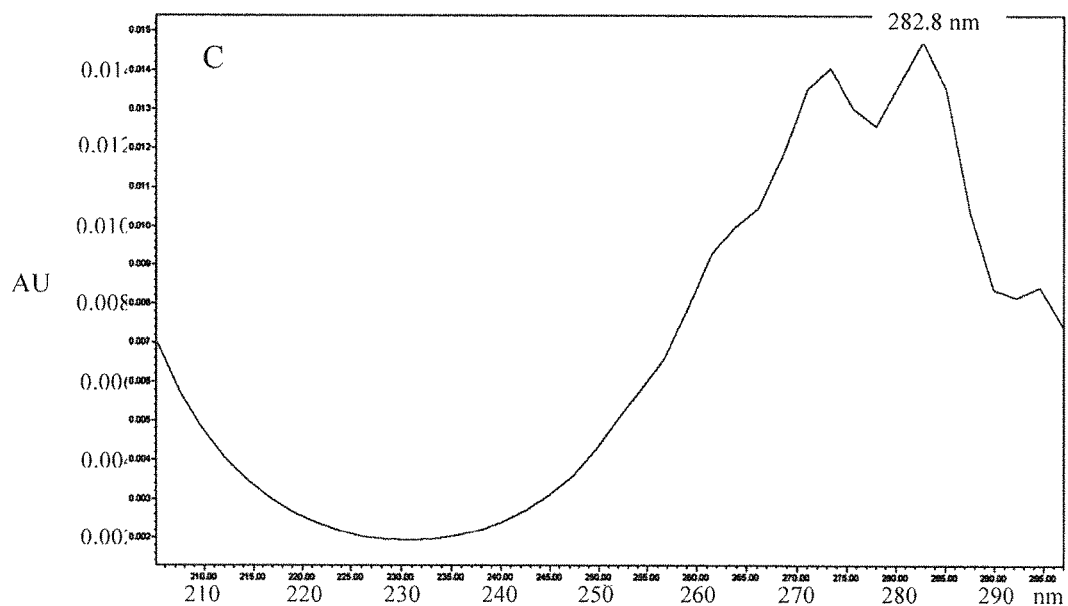
Figure 11:
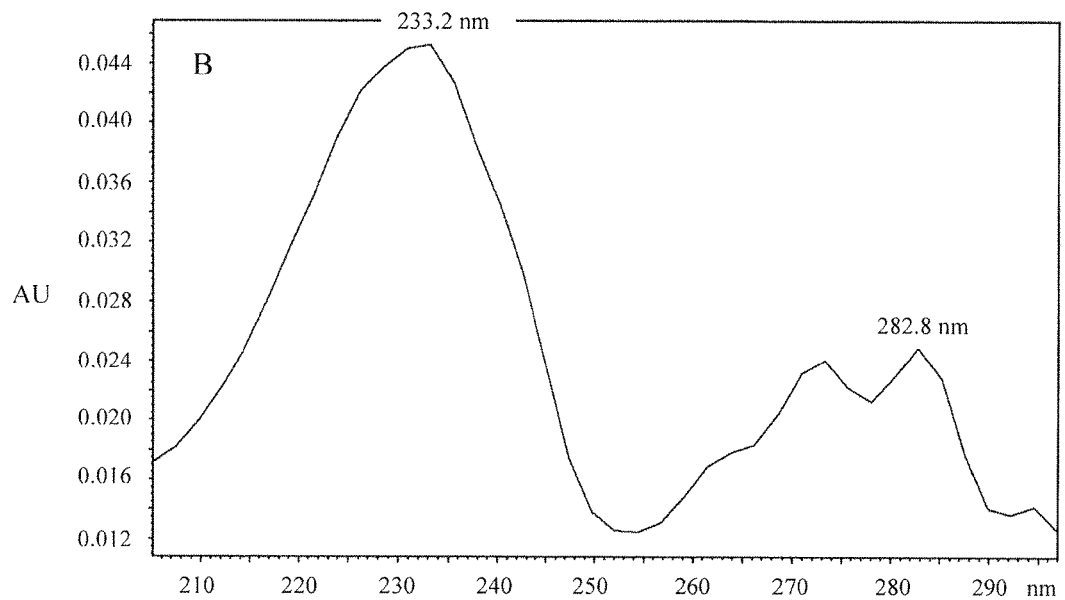
Figure 11:
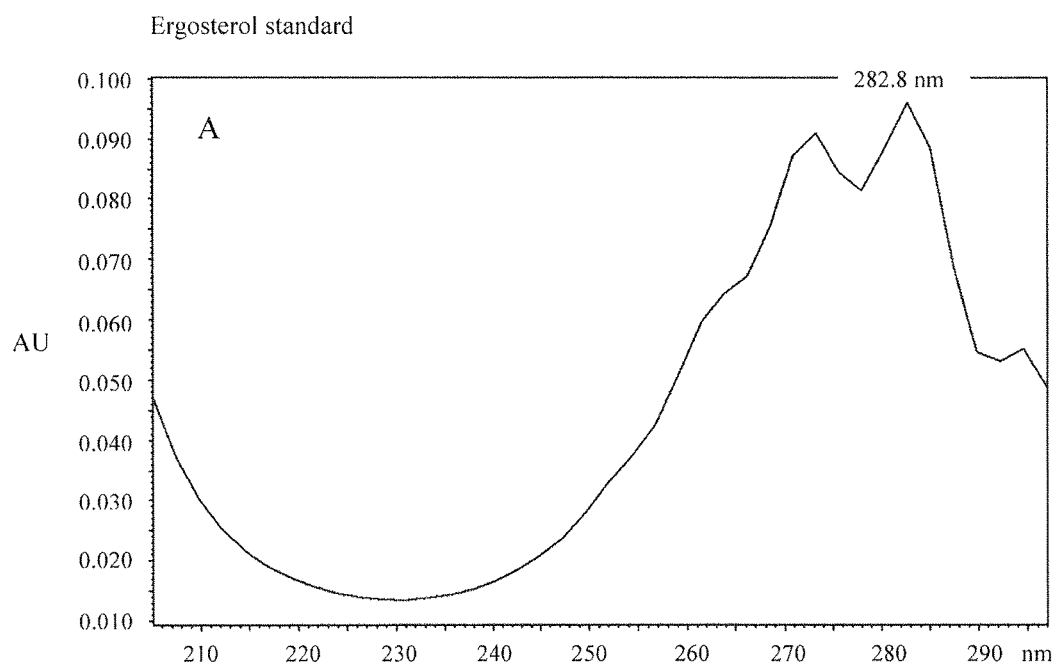

FIG. 11: UV spectra of single peaks from ERG6 wild type strains expressing putative cholesterol C25-hydroxylases. UV spectra were determined on-line between 205 and 300 nm with the PDA detector during HPLC as described in Example 9 for the following peaks:
A: ergosterol standard peak at 11.9 min (FIG. 10, profile A);
B: W303/V51-C25H1 peak at 10.0 min (FIG. 10, profile C);
C: W303/V51-C25H1 peak at 8.7 min (FIG. 10, profile C).

Figure 12:
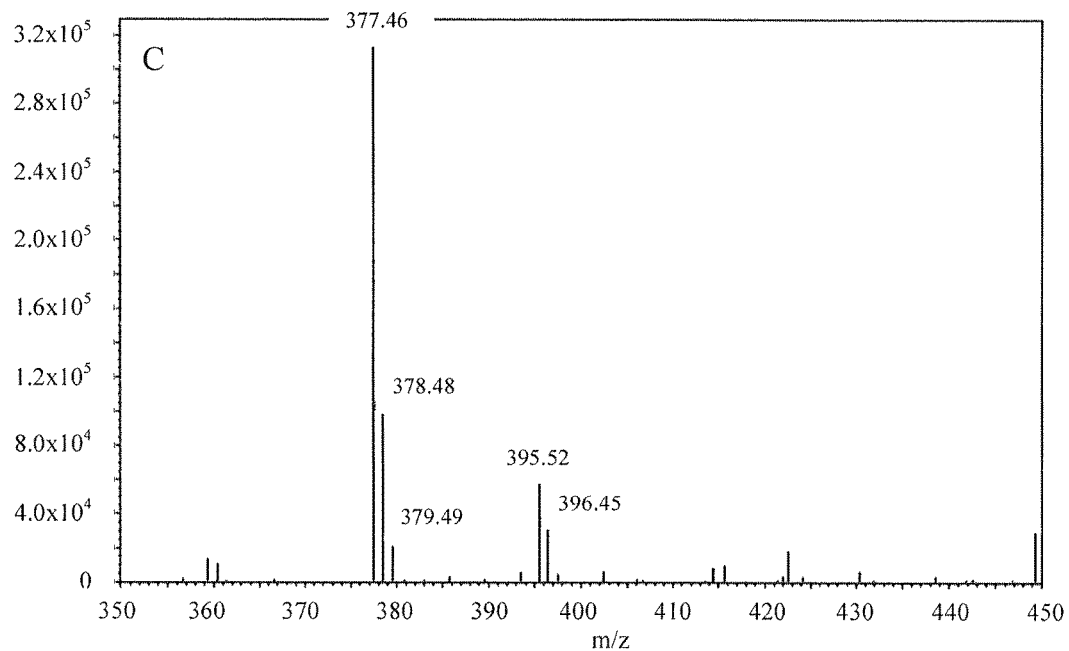
Figure 12:
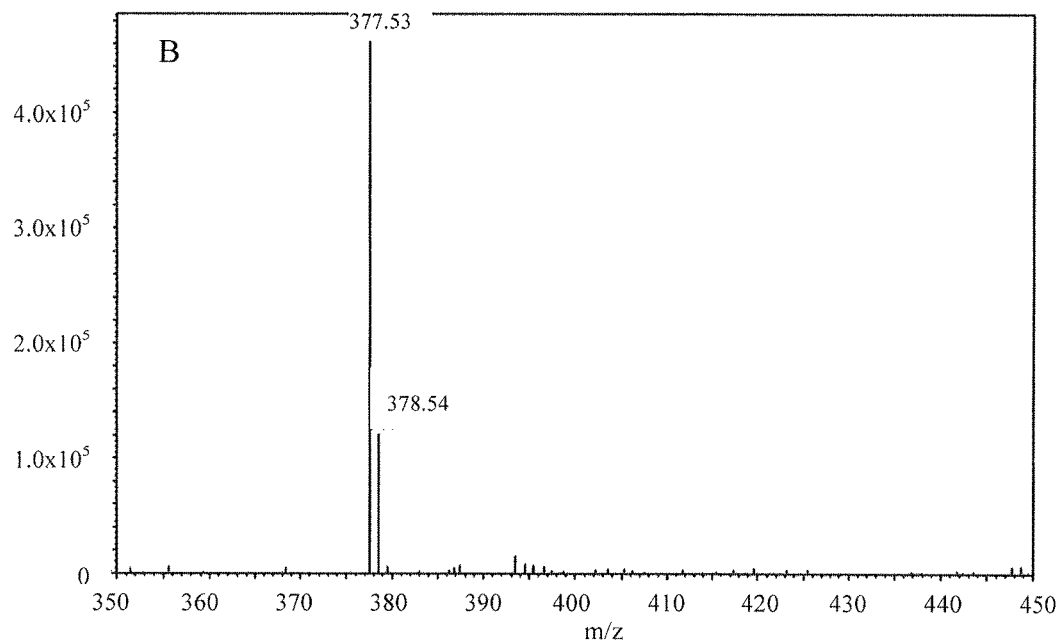
Figure 12:
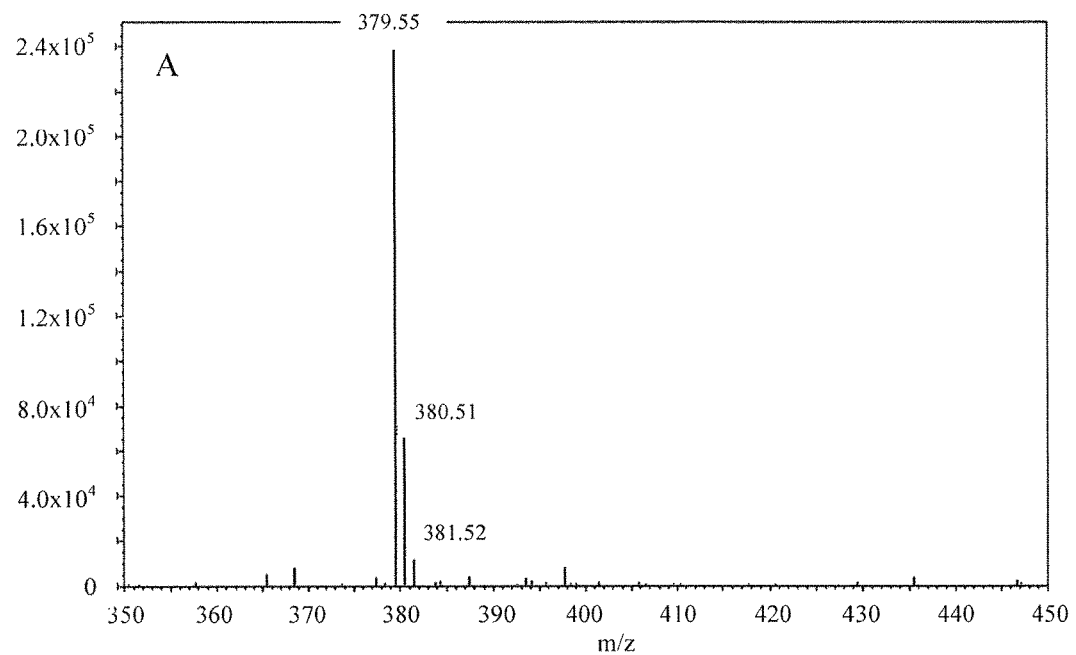

FIG. 12: Mass spectrometry profiles of single peaks from ERG6 wild-type strains expressing putative cholesterol C25-hydroxylases. The mass fragmentation profiles from m/z=350 to 450 were determined on-line with the Micro-Mass ZQ detector during HPLC as described in Example 9 on the following peaks:
A: ergosterol standard peak at 11.9 min (FIG. 10, profile A);
B: W303/V51-C25H1 peak at 10.0 min (FIG. 10, profile C);
C: W303/V51-C25H1 peak at 8.7 min (FIG. 10, profile C).

Figure 13:
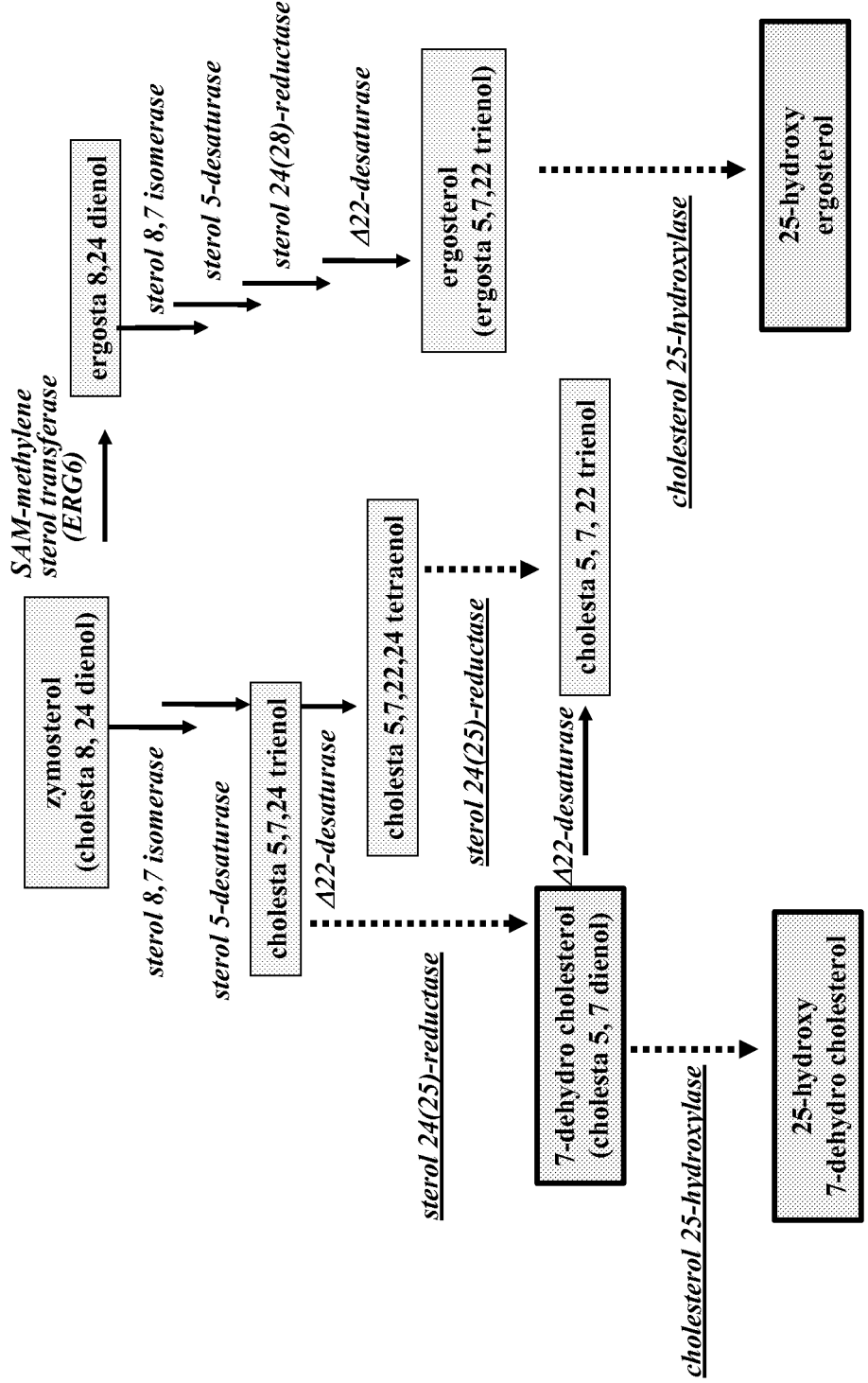

FIG. 13: The late part of the sterol biosynthetic pathway of wild-type yeast (ergosta-type sterols) compared to yeast in which ERG6 is inactivated (cholesta-type sterols). Enzymes are highlighted in italic. Filled arrows stand for enzyme reaction found in wild-type yeast. Dotted arrows correspond to steps catalysed by heterologous activities (putative sterol Δ24-reductase, putative cholesterol C25-hydroxylases), the corresponding enzymes are underlined.

Figure 14:
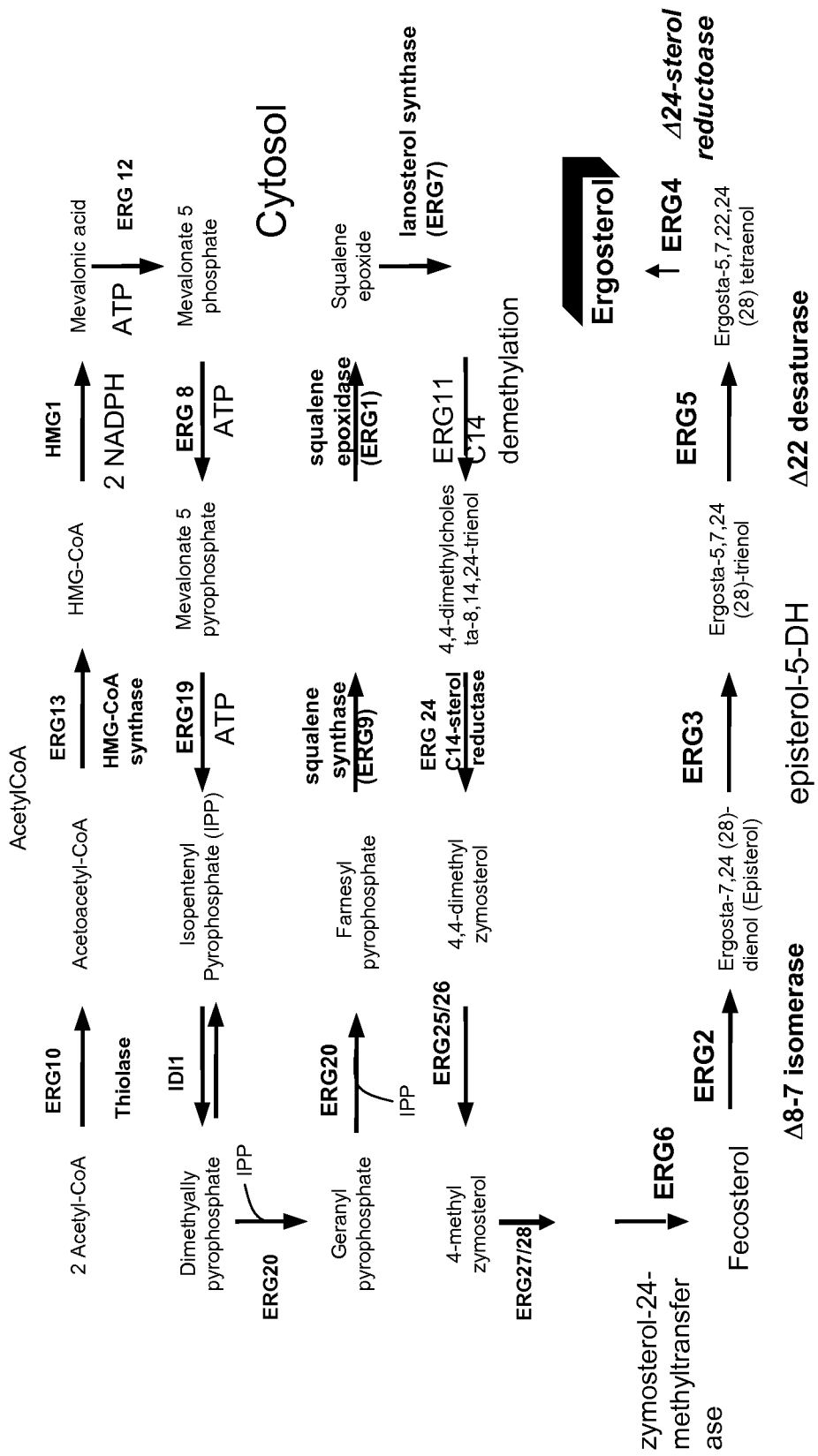

FIG. 14: is a diagram of the yeast sterol pathway.

Figure 15:
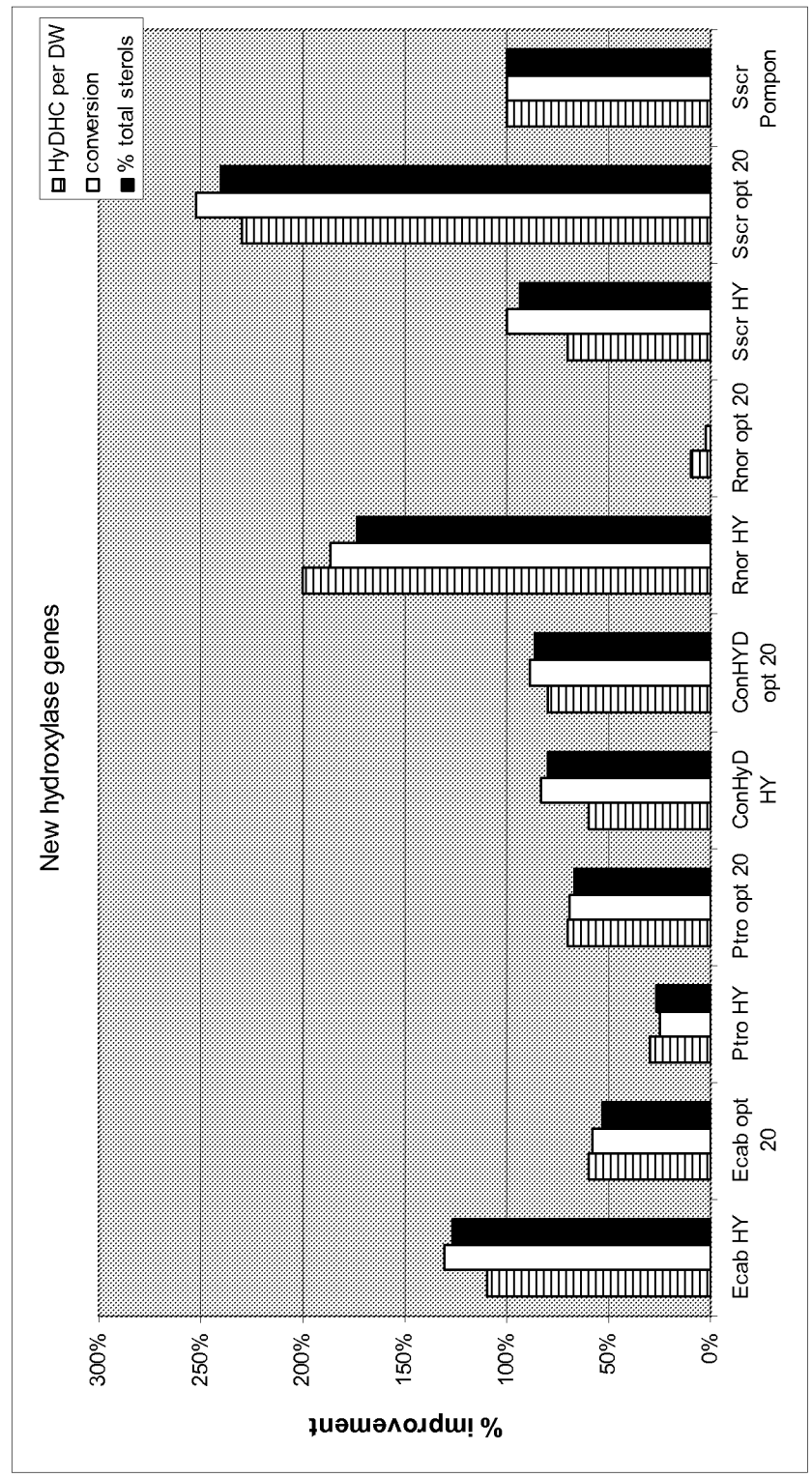

FIG. 15: is a comparison of the conversion of 7-dehydrocholesterol into 25-hydroxy-7-dehydrocholesterol (HyDHC) by ten different 25-hydroxylase genes. *S. cerevisiae* strains Ecab HY (integration construct possessing the gene of SEQ. ID. NO:26), Ecab opt 2.0 (integration construct possessing the gene of SEQ. ID. NO:25), Ptro opt 2.0 (integration construct possessing the gene of SEQ. ID. NO:19), Ptro HY (integration construct possessing the gene of SEQ. ID. NO:20), ConHyD HY (integration construct possessing the gene of SEQ. ID. NO:31), ConHyD opt 2.0 (integration construct possessing the gene of SEQ. ID. NO:30), Rnor HY (integration construct possessing the gene of SEQ. ID. NO:23), Rnor opt 2.0 (integration construct possessing the gene of SEQ. ID. NO:22), Sscr HY (integration construct possessing the gene of SEQ. ID. NO:28), Sscr opt 2.0 (integration construct possessing the gene of SEQ. ID. NO:27), and Scr Pompon, which contains the 25-hydroxylase from pig optimized as described in Example 2, were cultivated as described in Example 20. The sterols were isolated from the cell pellets and the HyDHC content, HyDHC proportion of total sterols, and the conversion of 7-DHC into HyDHC was compared to the values as obtained by integration of the 25-hydroxylase C25H1. All new hydroxylase genes were expressed and the gene product of which were able to hydroxylase 7-DHC into HyDHC.

DEFINITIONS

Throughout the specification and claims, the following definitions apply:

"Yeast" refers to *Saccharomyces cerevisiae*, as well as other yeast which are suitable for commercial scale production, such as *Schizosaccharomyces* spp., *Pichia* spp, *Klyuveromyces* spp., *Hansenula* spp. and *Yarrowia lipolytica*.

"Standard conditions" for hybridization mean in the context of the present invention the conditions which are generally used by a man skilled in the art to detect specific hybridization signals and which are described, e.g. by Sambrook et al., "Molecular Cloning", Second Edition, Cold Spring Harbor Laboratory Press 1989, New York, which is hereby incorporated by reference. An example of a "stringent hybridization condition" is overnight incubation (e.g., 15 hours) at 42° C. in a solution comprising: 50% formamide, 5×SSC (150 mM NaCl, 15 mM trisodium citrate), 50 mM sodium phosphate (pH 7.6), 5×Denhardt's solution, 10% dextran sulfate, and 20 μg/ml of denatured, sheared salmon sperm DNA, followed by washing the hybridization support in 0.1×SSC at about 65° C.

The term "% identity", as known in the art, means the degree of relatedness between polypeptide or polynucleotide sequences, as the case may be, as determined by the match between strings of such sequences. "Identity" can be readily determined by known methods, e.g., with the program BESTFIT (GCG Wisconsin Package, version 10.2, Accelrys Inc., 9685 Scranton Road, San Diego, Calif. 92121-3752, USA) using the following parameters: gap creation penalty 8, gap extension penalty 2 (default parameters).

A "functional" enzyme means that under typical yeast cultivation conditions, the enzyme will carry out the desired activity within the yeast. For example, a "functional cholesterol C25-hydroxylase" means that in a yeast cell in vivo, the cholesterol C25-hydroxylase will convert 7-dehydrocholesterol to 25-hydroxy-7-dehydrocholesterol.

A "functional" nucleic acid sequence means that the nucleic acid sequence includes necessary sequences (other than those coding for a polypeptide) in order for the yeast to express the polypeptide at a concentration to where it is functional. Such sequences can include promoter(s), termination sequences, enchancers and the like.

Cholesterol 25-hydroxylase

Thus one aspect of this invention is a method of producing 25-hydroxy-7-dehydrocholesterol or 25-hydroxyergosterol in a yeast cell comprising: contacting 7-dehydrocholesterol or ergosterol with a cholesterol C25-hydroxylase, and obtaining 25-hydroxy-7-dehydrocholesterol or 25-hydroxyergosterol. Preferably the cholesterol C25-hydroxylase is an enzyme from a vertebrate origin, more preferably from rat, pig, dog, horse, human, chimpanzee, *Macaca mulata*, mouse, *Gallus gallus*, *Xenopus laevis*, *Danio rerio* or *Ornithorynchus anatinus*. Further, derivatives of these native enzymes, i.e. those where the amino acid sequence no longer is the same as the native enzyme, may be used as long as they retain their ability to function. For example, this invention encompasses the use of enzymes which share at least 90% identity with a native vertebrate C25-hydroxylase, and preferably those with at least 95% identity, and more preferably at least 99% identity, with the proviso that the derivative enzyme retains its functionality.

Similarly, the nucleic acids which can be used in this invention are those which encode the above peptide sequences, and those which hybridize under stringent conditions to those which encode the above peptide sequences. Preferably they are isolated. Further, in some embodiments, the nucleic acid encoding the C25-hydroxylase enzyme has been codon-optimized to be better suited to the yeast environment. In preferred embodiments, the nucleic acid is from pig, rat, dog, chimpanzee, or horse and has been codon-optimized for yeast. Particularly preferred nucleic acids are those which have been codon-optimized such that they are expressed in a yeast host as least as well as the reference nucleic acid sequence "Sscr Pompon SEQ ID NO: 5", and more preferably the nucleic acid sequence is expressed better than Sscr Pompon".

The nucleic acids are preferably DNAs.

Particularly preferred nucleic acids are those designated as:

C25H1 (Based on pig hydroxylase; SEQ. ID NO. 5),
C25H3 (Based on dog hydroxylase: SEQ. ID. NO: 8)
Ecab_HY or Ecab 25OH_opt2.0 (Based on horse hydroxylase: SEQ ID NOS: 25 and 26)
ConHYD opt 20 (SEQ ID NO:30)
Rnor HY (Based on rat hydroxylase SEQ ID NO: 23)
Sscr HY (SEQ ID NO: 28)
Sscr opt 20 (SEQ ID NO: 27)
Sscr Pompon (SEQ ID NO: 5)

Another aspect of this invention is a yeast cell comprising a functional cholesterol C25-hydroxylase. A further aspect of this invention is a yeast which is able to convert 7-dehydrocholesterol or ergosterol into 25-hydroxy 7-dehydrocholesterol or 25-hydroxyergosterol, respectively.

A further aspect of this invention is a method of producing 25-hydroxy 7-dehydrocholesterol in a yeast comprising allowing expression of a vertebrate cholesterol C25-hydroxylase in the presence of 7-dehydrocholesterol under culture conditions which permit the hydroxylation reaction to occur, resulting in the production of 25-hydroxy 7-dehydrocholesterol. An additional aspect of this invention is a method of producing 25-hydroxyergosterol in a yeast comprising allowing expression of a vertebrate cholesterol C25-hydroxylase in the presence of ergosterol under culture conditions which permit the hydroxylation reaction to occur, resulting in the production of 25-hydroxyergosterol.

It is preferred that multiple copies of the gene be present in the expression vector. In preferred embodiments, 2-5 copies are used.

Vectors for the cloning of any of the aforementioned genes into the yeast host may be of any type known to be useful for cloning, particularly plasmids and centromeric plasmids carrying the C25-hydroxylase genes and associated expression and/or integration sequences including promoters and enhancers commonly used in the art, and these vectors make up another aspect of this invention.

In a yeast which is able to produce 7-dehydrocholesterol, such as that described in US 2006/0242508, it is preferred that the genes ERG5 and ERG6 are inactivated and a sterol Δ24-reductase originating from a vertebrate is expressed, such as those described further below. Furthermore, under some circumstances it is of advantage to overexpress a truncated version of HMG1 in such a yeast. Such strains with inactivated ERG5 and ERG6 and truncated HMG1 genes have been described in the art.

The 25-hydroxyprovitamin D3 or 25-hydroxyprovitamin D2 can then be converted to 25-hydroxyvitamin D3, the first metabolite and circulating form of vitamin D3, or D2, respectively, using known UV light irradiation procedures.

25-hydroxyvitamin D3 plays an important role in bone formation, and is commercially used as a vitamin supplement in poultry and other animal feeds. It is commercially available from DSM Nutritional Products under the trademark ROVIMIX HY-D®. 25-hydroxyvitamin D2 shows comparable effects as 25-hydroxyvitamin D3 in the body and can be used in a fashion similar to the usage of 25-hydroxyvitamin D3.

Sterol Δ24-Reductases

Another aspect of this invention is novel nucleic acids which encode a sterol Δ24-reductase and which can be expressed by a yeast and can convert a substrate selected from the group consisting of: lanosterol, dimethyl zymosterol, methyl zymosterol, zymosterol, cholesta-7,24-dienol or cholesta-5,7,24-trienol to a product selected from the group consisting of: 3 β-hydroxy-8-lanosta-8-ene, 4,4-dimethyl-cholesta-8-enol, 4 α-methyl-cholesta-8-enol, cholesta-8-enol, lathosterol and 7-dehydrocholesterol, with the proviso that the nucleic acid sequence is not a human or mouse nucleic acid sequence.

Preferably the yeast cell is one in which ERG6 and ERG5 are inactivated. Preferably these nucleic acids are modified DNAs from vertebrate origin which have been codon-optimized for the host cell, with the proviso that it is not mouse nor human. Preferably the sterol Δ24-reductase is from pig, dog, chimpanzee, *Macaca mulata*, mouse, rat, horse, *Gallus gallus*, *Xenopus laevis*, *Danio rerio* or *Ornithorynchus anatinus*.

In particularly preferred embodiments, these are rat (*Rattus norvegicus*) or zebrafish (*Danio rerio*) DNAs, and in more preferred embodiments they have been codon-optimized for expression in *Saccharomyces cerevisiae*. Particularly preferred nucleic acids are designated S24R1 (modified rat gene, nucleotides 10 to 1563 of SEQ ID NO 1) and S24R2 (modified zebrafish gene, nucleotides 10 to 1563 of SEQ ID NO: 3).

Another aspect of this invention is a vertebrate nucleic acid sequence, preferably DNA, which has been codon-optimized for expression in a yeast host, and which encodes a functional sterol Δ24-reductase enzyme such that within a yeast host cell, the enzyme can convert:
lanosterol to 3 β-hydroxy-8-lanosta-8-ene, or dimethyl zymosterol to 4,4-Dimethyl-cholesta-8-enol;
methyl zymosterol to 4 α-methyl-cholesta-8-enol;
zymosterol to cholesta-8-enol;
cholesta-7,24-dienol to lathosterol; or
cholesta-5,7,24-trienol to 7-dehydrocholesterol);
and the nucleic acid encoding the enzyme can hybridize to S24R1 or S24R2 under stringent conditions, with the proviso that the vertebrate nucleic acid sequence is not a nucleic acid sequence isolated from human or mouse.

Another aspect of this invention are the enzymes encoded by the aforementioned nucleic acid sequences. Preferred enzymes of this invention are those given as SEQ ID NO. 2 and 4 and those which exhibit at least a 90%, and preferably a 95% identity to SEQ ID NO 2 or 4 and which also can convert
lanosterol to 3 β-hydroxy-8-lanosta-8-ene,
dimethyl zymosterol to 4,4-dimethyl-cholesta-8-enol,
methyl zymosterol to 4 α-methyl-cholesta-8-enol,
zymosterol to cholesta-8-enol,
cholesta-7,24-dienol to lathosterol, or
cholesta-5,7,24-trienol to 7-dehydrocholesterol within a yeast cell environment.

Another aspect of this invention is a yeast host containing a functional nucleic sequence as described above, and particularly a yeast host such as *S. cerevisiae* comprising S24R1, S24R2, or a nucleic acid sequence which hybridizes to S24R1 or S24R2 under stringent conditions, with the proviso that the nucleic acid is not a human nor a mouse sequence. In preferred embodiments, the yeast hosts have had ERG5 and ERG6 inactivated; and in a particularly preferred embodiment, the yeast host also over-expresses a truncated version of the HMG1 gene.

Yet another aspect of this invention is a method of producing 3 β-hydroxy-8-lanosta-8-ene, 4,4-dimethyl-cholesta-8-enol, 4 α-methyl-cholesta-8-enol, cholesta-8-enol, lathosterol or 7-dehydrocholesterol within a yeast cell comprising contacting lanosterol, dimethyl zymosterol, methyl zymosterol, zymosterol, cholesta-7,24-dienol or cholesta-5,7,24-trienol with a yeast comprising a nucleic acid sequence which has been codon-optimized for expression in a yeast host, and which encodes a functional sterol Δ24-reductase enzyme, with the proviso that the nucleic acid sequence is not a human nor mouse nucleic acid sequence, and
the yeast converts:
lanosterol to 3 β-hydroxy-8-lanosta-8-ene,
dimethyl zymosterol to 4,4-dimethyl-cholesta-8-enol,
methyl zymosterol to 4 α-methyl-cholesta-8-enol,
zymosterol to cholesta-8-enol,
cholesta-7,24-dienol to lathosterol, or
cholesta-5,7,24-trienol to 7-dehydrocholesterol. In this method, the nucleic acid is preferably S24R1, S24R2 or a nucleic acid which can hybridize to S24R1 or S24R2 under stringent conditions, with the proviso that the vertebrate nucleic acid sequence is not a human or mouse nucleic acid sequence.

Another aspect of this invention includes vectors, including plasmids, comprising a functional nucleic acid sequence which has been codon-optimized for expression in a yeast host, and which encodes a functional sterol Δ24-reductase enzyme, with the proviso that the nucleic acid sequence is not a human nor mouse nucleic acid sequence. Preferably, the vector comprises the nucleic acids S24R1, S24R2 or a nucleic acid which can hybridize to S24R1 or S24R2 under stringent conditions, with the proviso that the vertebrate nucleic acid sequence is not a human or mouse nucleic acid sequence. The vectors may contain the usual sequences commonly found in plasmids or other vectors which regulate transcription, translation, and/or integration into the yeast chromosome.

Gene Constructs

All of the gene constructs of this invention which encode C25-hydroxylase or a sterol Δ24 reductase, are typically part of an expression cassette typically having the foreign gene under the control of known promoters which can be regulated using standard methods, such as the ADH1 promoter, TEF1 promoter, yeast GPD (TDH3) promoter, yeast HXT7 promoter, yeast GAL1/10 promoter or yeast PGK1 promoter controlling the gene of interest. Additionally the expression cassette may comprise upstream and downstream sequences such as a terminator sequence and/or other regulatory elements which are operatively linked to the coding sequence for at least one of the above described genes. The vectors carrying the gene constructs of this invention are introduced into the yeast using conventional methods.

The following examples are illustrative only and are not intended to limit the scope of the invention in any way. The contents of all references, patent applications, patents and published patent applications, cited throughout this application are hereby incorporated by reference.

EXAMPLES

References

Complete citations for references appear at the end of the Examples. All references are hereby incorporated by reference herein.

Media

TABLE 1

Composition of the minimal medium

| Composition | Concentration (weight/volume) |
|---|---|
| Yeast Nitrogen Base without amino acids and ammonium sulphate (Becton Dickinson and Co., Sparks, MD 21152, USA) | 0.17% |
| Casaminoacids (Becton Dickinson and Co., Sparks, MD 21152, USA) | 1% |
| Glucose (Sigma-Aldrich, St. Louis, MO 63103, USA) | 2% |

The medium was sterilized by autoclaving 20 minutes at 120° C. prior to its utilization. Sterile tryptophan, uracil or adenine (b) were added to a final concentration of 20 mg/l if required.

TABLE 2

Composition of the Kapelli synthetic medium.

| Composition | Concentration |
|---|---|
| $H_3PO_4$ (85% v/v) | 0.33 ml/l |
| $KH_2PO_4$ | 2.85 g/l |
| $MgSO_4 \times 7H_2O$ | 0.6 g/l |
| $MnSO_4 \times H_2O$ | 16 mg/l |
| $CuSO_4 \times 5H_2O$ | 0.4 mg/l |
| $ZnSO_4 \times 7H_2O$ | 15 mg/l |
| $CoCl_2 \times 6H2O$ | 2.8 mg/l |
| $Na_2MoO_4 \times 2H_2O$ | 2.5 mg/l |
| $H_3BO_3$ | 7.5 mg/l |
| Citric acid $\times H_2O$ | 0.5 mg/l |
| KI | 1 mg/l |
| $NiSO_4 \times 7H_2O$ | 2.5 mg/l |
| Tri-sodium citrate $\times 2H_2O$ | 25 mg/l |
| Thiamine HCl | 2 mg/l |
| Pyridoxine HCl | 5 mg/l |
| Nicotinic acid | 8 mg/l |
| Biotin | 0.05 mg/l |
| Calcium pantothenate | 10 mg/l |
| myo-inositol | 80 mg/l |
| $CaCl_2 \times 2H_2O$ | 50 mg/l |
| $FeCl_3 \times 6H_2O$ | 50 mg/l |
| Casaminoacids | 1% (w/v) |
| Glucose or Galactose | 2% (w/v) |

The medium was sterilized by filtration through a 0.2 μm filtration unit prior to use. Sterile tryptophan, uracil or adenine were added to a final concentration of 0.2 mg/ml, if required.

Example 1

Selection of $\Delta^{24\ (25)}$-Sterol Reductases from Different Organisms and Design of Synthetic Genes Sterol $\Delta 24$-reductase catalyzes one of the last steps of cholesterol biosynthesis. It is a rather unspecific enzyme accepting at least zymosterol and desmosterol as substrate. In 2004, the corresponding gene was identified in human (Waterman H R et al., 2001). Only for the gene products from human and mouse the sterol $\Delta 24$-reductase activity was formally proven (Crameri A et al., 2006; WO03/064650). A comparable function was also described for the homologous gene from rat (Wu C. et al. 2004: *Nature* 432 (7017):640-5.), however, without confirmation of the enzymatic activity of the gene product.

In WO03/064650 it is shown that expression of the $\Delta 24$-reductase gene from mouse in a *S. cerevisiae* mutant (erg5 erg6) resulted in the formation of two new sterols (lathosterol and 7-dehydrocholesterol), which do not occur in the host strain. Searching of public databases like GENBANK or EMBL for enzymes that are homologous to the human $\Delta^{24\ (25)}$-sterol reductase was done with the publicly available program BLASTp used under standard conditions. Among the sequences found, the sequence of *Rattus norvegicus*, showing 97% amino acid identity to the amino acid sequence of *Homo sapiens* (Table 1) and the sequence of *Danio rerio*, showing 79% amino acid identity to the human sequence (Table 1), were selected for further investigations.

TABLE 3

Putative proteins homologous to the human $\Delta^{24\ (25)}$-sterol reductase. Numbers are given in percent amino acid identity.

| | Homo sapiens | Rattus norvegicus | Danio rerio |
|---|---|---|---|
| Homo sapiens | 100% | 97% | 79% |
| Pan troglodytes | 99% | 97% | 79% |
| Macaca mulata | 99% | 97% | 79% |
| Mus musculus | 96% | 99% | 79% |
| Rattus norvegicus | 97% | 100% | 79% |
| Bos taurus | 96% | 96% | 79% |
| Canis familiaris | 96% | 96% | 79% |
| Equus caballus | 95% | 95% | 79% |
| Gallus gallus | 79% | 79% | 78% |
| Danio rerio | 79% | 79% | 100% |
| Xenopus laevis | 77% | 77% | 79% |

For each cDNA a synthetic gene for expression in *S. cerevisiae* was designed. In general, it is possible to use the original cDNA sequence for this purpose. In some instances it is of advantage to try to adapt the codon usage profile of the original cDNA to the codon usage of the new host using the codon usage tables of the different species according to Kazusa DNA Research Institute (http://www.kazusa/or.jp/codon). This can be done by hand or by the help of a computer program. In our case a computer program was used, the calculation algorithm of which involves a sequence generator allowing generation of DNA sequences with user defined codon bias modulation. Some constraints can be also introduced into the algorithm to avoid or alternatively to favor, at will, the presence of specific restriction sites. Part of the sequence generation is driven by a random number generator usually resulting in different DNA sequences per attempt. It was not possible for the user of the program to recover the used seed and thus to reproduce the results. Therefore, recoded sequences can not be predicted and can be considered to carry a unique and original signature.

The selection among alternatively generated DNA sequence versions was finally user dependent (visual inspection). The selected version of the DNA sequences was used for gene synthesis by a service provider (e.g. GeneCust Europe, 30b rue Dominique Lang, 3505 Dudelange, Luxembourg). Three additional adenine residues were added upstream of the ATG initiation codon and a second STOP codon is added downstream of the open reading frame in order to optimize translational initiation and termination.

For convenient cloning of the synthetic genes into yeast expression vectors, Bam HI and Eco RI restrictions sites were added upstream and downstream of the sequences, respectively. As explained above, the rat sterol Δ24-reductase gene (GenBank entry number AY92220 (cDNA sequence) and AAX29968 (amino acid sequence) was recoded by the method described above. The new synthetic gene was named S24R1. Its sequence is given below.

```
SEQ. ID. NO: 1:
   1 GGATCCAAAA TGGAACCAGC TGTTTCTTTA GCTGTTTGTG CTTTATTATT TTTATTATGG
  61 GTAAGAGTCA AAGGTCTTGA ATTTGTCTTA ATTCATCAAA GGTGGGTGTT TGTCTGTTTA
 121 TTTTTATTAC CATTATCTTT AATCTTTGAT ATCTATTATT ATGTTAGAGC TTGGGTTGTT
 181 TTTAAATTAT CTTCTGCTCC AAGACTACAT GAACAAAGAG TTCAAGATAT CCAAAAACAA
 241 GTTAGAGAAT GGAAAGAACA AGGTTCTAAA ACTTTTATGT GTACCGGTCG GCCTGGGTGG
 301 CTCACTGTGT CATTAAGGGT TGGTAAATAT AAAAAAACTC ATAAAAATAT CATGATCAAT
 361 TTAATGGATA TCTTAGAAGT TGATACTAAA AAACAAATCG TCAGGGTTGA ACCTCTTGTC
 421 TCTATGGGGC AAGTCACTGC ATTATTAAAT TCTATTGGTT GGACGCTTCC TGTCCTCCCA
 481 GAGTTAGACG ATCTTACTGT TGGTGGTTTA ATCATGGGTA CTGGTATCGA ATCTTCATCT
 541 CATAAATATG GTCTTTTTCA ACATATTTGT ACCGCTTATG AACTAATCCT GGCTGATGGC
 601 TCATTTGTGC GTTGTACCCC TTCGGAAAAC TCCGATCTAT TTTATGCAGT CCCATGGAGT
 661 TGTGGTACTT TAGGTTTTTT AGTTGCTGCT GAAATCAGAA TCATCCCAGC AAAAAAGTAT
 721 GTCAAGCTAC GATTTGAACC TGTTAGAGGT CTGGAAGCAA TCTGTGAAAA GTTTACACAT
 781 GAATCTCAAA GATTAGAAAA TCATTTTGTT GAAGGGCTTC TCTATAGTCT GGATGAGGCG
 841 GTGATTATGA CGGGGGTGAT GACGGACGAC GTTGAGCCAT CTAAATTAAA TTCTATCGGT
 901 TCTTATTATA AACCATGGTT TTTTAAACAT GTTGAAAATT ATTTAAAAAC TAATAGGGAA
 961 GGATTAGAAT ACATTCCATT AAGACATTAT TATCATAGAC ATACTAGGTC TATCTTTTGG
1021 GAATTACAAG ATATCATCCC ATTTGGTAAT AATCCAATCT TTAGATATTT ATTTGGTTGG
1081 ATGGTTCCAC AAAAATCTC TTTATTAAAA TTAACTCAAG GTGAAACTTT ACGAAAGCTA
1141 TATGAGCAAC ACCACGTCGT TCAAGATATG TTAGTTCCAA TGAAATGTTT ATCTCAAGCA
1201 TTACATACCT TCCAAAATGA TATCCATGTT TATCCAATCT GGTTATGTCC ATTTATCTTA
1261 CCATCTCAAC CTGGTCTGGT CCACCCTAAA GGTGACGAAG CTGAACTTTA TGTTGATATC
1321 GGTGCCTATG GTGAGCCAAG AGTTAAACAT TTTGAAGCTA GATCATGTAT GAGACAATTA
1381 GAAAAATTTG TTAGATCAGT TCATGGTTTT CAAATGCTAT ATGCAGATTG TTACATGAAC
1441 AGAGAAGAAT TTTGGGAAAT GTTCGATGGT TCTTTATATC ATAAATTAAG AAAACAATTA
1501 GGTTGTCAAG ATGCTTTTCC AGAAGTTTAT GATAAAATCT GTAAAGCTGC TAGACACTAA
1561 TGAGAATTC
```

The corresponding amino acid sequence is:

```
SEQ. ID. NO: 2
   1 MEPAVSLAVC ALLFLLWVRV KGLEFVLIHQ RWVFVCLFLL PLSLIFDIYY YVRAWVVFKL
  61 SSAPRLHEQR VQDIQKQVRE WKEQGSKTFM CTGRPGWLTV SLRVGKYKKT HKNIMINLMD
 121 ILEVDTKKQI VRVEPLVSMG QVTALLNSIG WTLPVLPELD DLTVGGLIMG TGIESSSHKY
 181 GLFQHICTAY ELILADGSFV RCTPSENSDL FYAVPWSCGT LGFLVAAEIR IIPAKKYVKL
 241 RFEPVRGLEA ICEKFTHESQ RLENHFVEGL LYSLDEAVIM TGVMTDDVEP SKLNSIGSYY
 301 KPWFFKHVEN YLKTNREGLE YIPLRHYYHR HTRSIFWELQ DIIPFGNNPI FRYLFGWMVP
 361 PKISLLKLTQ GETLRKLYEQ HHVVQDMLVP MKCLSQALHT FQNDIHVYPI WLCPFILPSQ
```

421 PGLVHPKGDE AELYVDIGAY GEPRVKHFEA RSCMRQLEKF VRSVHGFQML YADCYMNREE

481 FWEMFDGSLY HKLRKQLGCQ DAFPEVYDKI CKAARH

The *D. rerio* sterol Δ24-reductase gene (DNA sequence accessible at GenBank number NM_001008645 and amino acid sequence at GenBank number NP_001008645) was recoded with the method described above. The new synthetic gene was named S24R2. Its sequence is given below:

SEQ ID NO: 3
```
   1 GGATCCAAAA TGGACCCTTT GCTTTACCTT GGAGGCCTAG CGGTCCTCTT CCTTATTTGG

61 ATTAAGGTAA AAGGTTTAGA ATATGTTATT ATCCATCAAA GATGGATCTT TGTTTGTTTA

121 TTTTTATTAC CATTATCTGT CGTCTTCGAT GTTTATTATC ATTTAAGAGC TTGGATCATC

181 TTTAAAATGT GTTCTGCTCC AAAACAACAT GATCAAAGAG TTAGGGATAT TCAAAGGCAA

241 GTCCGTGAAT GGCGGAAGGA TGGGGGTAAG AAATACATGT GCACCGGTAG GCCAGGTTGG

301 CTGACTGTTT CTTTAAGAGT CGGTAAATAT AAAAAAACTC ATAAAAATAT CATGATCAAT

361 ATGATGGATA TCTTAGAAGT TGATACCAAA AGAAAAGTTG TGAGAGTAGA ACCATTAGCT

421 AATATGGGTC AAGTTACTGC TTTATTAAAT TCTATCGGTT GGACATTACC TGTCTTACCA

481 GAACTTGATG ACTTAACTGT TGGTGGTTTA GTCATGGGCA CTGGTATTGA ATCTTCTTCT

541 CATATCTATG GTTTATTTCA ACATATCTGT GTTGCATTTG AATTAGTTTT AGCTGATGGT

601 TCTTTAGTTA GGTGTACAGA AAAGGAAAAC TCTGATTTAT TTTATGCTGT CCCATGGAGC

661 TGTGGTACCT TAGGTTTTCT AGTCGCGGCT GAAATTCGTA TTATTCCTGC TCAAAAATGG

721 GTCAAATTAC ATTATGAACC TGTCAGGGGA TTAGACGCTA TTTGCAAAAA ATTTGCTGAA

781 GAGTCTGCTA ATAAAGAAAA TCAATTTGTT GAAGGATTAC AATATTCTAG AGATGAAGCT

841 GTTATTATGA CGGGTGTAAT GACGGATCAT GCAGAACCCG ATAAAACTAA TTGTATTGGG

901 TATTATTATA AACCTTGGTT CTTTAGACAT GTTGAATCTT TTTTAAAACA AAATAGAGTT

961 GCTGTTGAAT ATATCCCATT AAGACATTAT TATCATAGAC ATACTAGATC AATCTTTTGG

1021 GAACTGCAAG ACATCATTCC ATTTGGCAAT AATCCACTTT TTAGGTACGT TTTTGGATGG

1081 ATGGTGCCAC CAAAAATCTC TTTATTAAAA TTAACTCAAG GTGAAACTAT CAGAAAATTA

1141 TATGAACAAC ATCATGTTGT TCAAGATATG TTAGTTCCAA TGAAAGATAT CAAAGCTGCT

1201 ATCCAAAGAT TCATGAAGA TATTCATGTC TATCCATTAT GGCTTTGTCC ATTTTTATTA

1261 CCAAATCAAC CTGGAATGGT GCATCCGAAA GGGGATGAGG ACGAGTTATA TGTGGATATT

1321 GGGGCCTACG GCGAACCCAA AGTAAAACAT TTCGAAGCAA CTTCTTCTAC TAGACAATTA

1381 GAAAAATTTG TCCGTGATGT CCATGGTTTT CAAATGCTCT ACGCAGATGT CTATATGGAG

1441 AGAAAAGAAT TTGGGAAAT GTTCGACGGT ACTTTATATC ATAAATTAAG AGAAGAACTG

1501 GGCTGTAAGG ATGCCTTTCC CGAAGTGTTT GACAAAATCT GTAAAGTGC ACGTCATTAA

1561 TGAGAATTC
```

The corresponding amino acid sequence is:

SEQ. ID. No: 4
```
   1 MDPLLYLGGL AVLFLIWIKV KGLEYVIIHQ RWIFVCLFLL PLSVVFDVYY HLRAWIIFKM

61 CSAPKQHDQR VRDIQRQVRE WRKDGGKKYM CTGRPGWLTV SLRVGKYKKT HKNIMINMMD

121 ILEVDTKRKV VREPLANMG QVTALLNSIG WTLPVLPELD DLTVGGLVMG TGIESSSHIY

181 GLFQHICVAF ELVLADGSLV RCTEKENSDL FYAVPWSCGT LGFLVAAEIR IIPAQKWVKL
```

```
241 HYEPVRGLDA ICKKFAEESA NKENQFVEGL QYSRDEAVIM TGVMTDHAEP DKTNCIGYYY

301 KPWFFRHVES FLKQNRVAVE YIPLRHYYHR HTRSIFWELQ DIIPFGNNPL FRYVFGWMVP

361 PKISLLKLTQ GETIRKLYEQ HHVVQDMLVP MKDIKAAIQR FHEDIHVYPL WLCPFLLPNQ

421 PGMVHPKGDE DELYVDIGAY GEPKVKHFEA TSSTRQLEKF VRDVHGFQML YADVYMERKE

481 FWEMFDGTLY HKLREELGCK DAFPEVFDKI CKSARH
```

Example 2

Selection of Amino Acid Sequences that are Homologous to the Cholesterol C25-hydroxylase Amino Acid Sequence from *Homo sapiens* and Calculation of Alternative DNA Sequences Optimized for Expression in *S. Cerevisiae*

Cholesterol C25-hydroxylase activity has been shown for gene products *H. sapiens* and *M. musculus* (Lund et al., 1998; U.S. Pat. No. 6,562,609). Searching of public databases like GENBANK or EMBL for enzymes that are homologous to the human cholesterol C25-hydroxylase was done with the publicly available program BLASTp used under standard conditions. Among the found sequences, the sequence of *S. scrofa*, showing 82% amino acid identity to the amino acid sequence of *H. sapiens* (Table 2) and 79% to the sequence of *M. musculus*, and the sequence of *C. familiaris*, showing 70% amino acid identity to the human and to the mouse sequence (Tab. 4), were selected for further investigations.

TABLE 4

Amino acid identity among different putative cholesterol C25-hydroxylases

|  | Homo sapiens | Mus musculus | Sus scrofa | Canis familiaris |
| --- | --- | --- | --- | --- |
| Homo sapiens | 100% | 78% | 82% | 70% |
| Pan troglodytes | 99% | 78% | 82% | 70% |
| Macaca mulata | 94% | 77% | 82% | 70% |
| Mus musculus | 78% | 100% | 79% | 70% |
| Rattus norvegicus | 80% | 86% | 79% | 72% |
| Bos taurus | 84% | 79% | 86% | 70% |
| Equus caballus | 83% | 79% | 83% | 73% |
| Gallus gallus | 61% | 58% | 59% | 57% |
| Ornithorhynchus anatinus | 63% | 62% | 61% | 58% |

The pig cholesterol C25-hydroxylase gene (DNA sequence accessible at GenBank number AY974088 and amino acid sequence at GenBank number Q4G1G8) was recoded by replacing twenty five codons corresponding to codons rarely used by the yeast *Saccharomyces cerevisiae* by codons frequently used in yeast (Zhang et al., 1991). The new synthetic gene was designated C25H1. Its sequence is given below:

```
SEQ. ID. NO: 5
  1 GGATCCAAAA TGAGCGGCCA CAACAACTCC GAGCTTTTCG TCCTTTGCAG CTCCAGCCAG

61 CTGTTCCTGC AGCCCCTTTG GGACCACCTG AAGACCTGGG AGACCCTTAT CCTGTCGCCC

121 TTCTTCCCAG TCTTCTTCTC CATCACCACC TACTTGGGCT TCTGCCTGCC CTTCGTGGTA

181 CTGGATGTCT TATGCCCATG GGTGCCCGCA CTGAGGCGTT ACAAGATCCA CCCAGACTTC

241 TCGCCATCGG TGTGGCAGCT GCTGCCCTGC CTGGGGCTGA CACTTTACCA GCATGTGGTG

301 TTCGTGTTCC CAATGACTCT GTTGCACTGG GCAGCAAGCC CAGTTCTTCT GCCCCCAGAA

361 GCCCCCGAGC TGCTTCAGCT GGTGCGTCAC ATCGTGCTGT GCCTGCTGCT TTTCGACACC

421 GAATTTTTCA TCTGGCATGT GCTGCATCAC AAAGTGCCTT GGCTGTACAG GACCTTCCAC

481 AAGATGCACC ACCAGAACTC GTCCTCGTTC GCACTGGCCA CACAGTACAT GAGTGTCGGG

541 GAGCTACTTT CTTTGGGTGT CTTTGACATG GTGAACATCA TGCTGCTTAG GTGCCACCCA

601 CTTACCGTCC TGATCTTCCA CGTGATCAAC ATCTGGCTGT CGGTGGAGGA CCACTCCGGC

661 TATGACTTCC CCTGGTCCGC TCACAGACTA GTACCTTTCG GGTGGTATGG GGGCGTGACA

721 CACCACGACC TACATCACTC CCAGTTTAAC TGCAACTTCG CCCCTTACTT CACACACTGG

781 GACAAAATAC TGGGAACACT GAGGTCTGCT CATGCCAAGT AATGAGAATT C
```

The corresponding amino acid sequence is:

```
SEQ. ID. No: 6
    1 MSGHNNSELF VLCSSSQLFL QPLWDHLKTW ETLILSPFFP VFFSITTYLG FCLPFVVLDV

61 LCPWVPALRR YKIHPDFSPS VWQLLPCLGL TLYQHVVFVF PMTLLHWAAS PVLLPPEAPE

121 LLQLVRHIVL CLLLFDTEFF IWHVLHHKVP WLYRTFHKMH HQNSSSFALA TQYMSVGELL

181 SLGVFDMVNI MLLRCHPLTV LIFHVINIWL SVEDHSGYDF PWSAHRLVPF GWYGGVTHHD

241 LHHSQFNCNF APYFTHWDKI LGTLRSAHAK
```

An alternative amino acid sequence of a putative pig sterol C25-hydroxylase from the database GENBANK showing four differences to the used sequence is also available, but was not further used in the experiments:

```
SEQ ID NO: 7
    1 MSGHNNSELL VLCSSGQLFL QPLWDHLKTW ETLIQSPFFP VFFSITTYLG FCLPFVVLDV

61 LCPWVPALRR YKIHPDFSPS VWQLLPCLGL TLYQHVVFVF PMTLLHWAAS PVLLPPEAPE

21 LLQLVRHIVL CLLLFDTEFF IWHVLHHKVP WLYRTFHKMH HQNSSSFALA TQYMSVGELL

181 SLGVFDMVNI MLLRCHPLTV LIFHVINIWL SVEDHSGYDF PWSTHRLVPF GWYGGVTHHD

241 LHHSQFNCNF APYFTHWDKI LGTLRSAHAK
```

The gene from *Canis familiaris* (nucleotide sequence accessible at GenBank number XM_546596.2 and amino acid sequence at GenBank number XP_543596.1) was recoded with the fitting method described in Example 1. The new synthetic gene was named C25H3, and its DNA sequence is given below:

```
SEQ ID. NO. 8:
    1 GGATCCAAAA TGTCTTCACA TAATTCTTCT GGTCCTTTAG CCTTAGGACC ACCTGGTCAA

61 CTATTATTAC AACCTTTATG GGACCAAGTT AGGGCAAGGG CAGCATTAGC GCAATCGCCT

121 CCCTTTGCAG TCCTTTTTTC TATCACTGCT TATTTAGGTT GTTGTTTACC ATTTGTTTTA

181 TTAGATTTAT TATGTCCAAG AGTTAGAGCA TTAAGGAGAT ATAAAGTCCA TCCCGATTGT

241 GGACCATCTG CAAGGCAATT ATTAGGTTGT TTAGGTAGGA CTGTCTGTCA ACATGTAGCT

301 TTATTATTAC CAGCTTCTTT ATTACATTGT GCCAGGGGTC CCGCTCCATG GCCGAGAGAA

361 GCACCAGAAT TATTACAATT AGCTAGACAT GTTTTAGGTT GTTATTATT ATTTGATGCT

421 GAAGTTTTTG CTTGGCACGT TTTACATCAT AGAGTTCCAT GGCTTTATAG AACTTTTCAT

481 AAATTACATC ATCAACATGC TGCTTCATTT GCTTTAGCTA CTCAATATAT GGGTGCTTGG

541 GAGTTATTAT CTTTAGGTTT TTTTCATGTT TTAAATGTTG TTTTATTACA ATGTCATCCA

601 TTATCTGTTT TAGCTTTTCA TTTATTAAAT ATCTGGCTAT CTGTTGAAGA TCATTCAGGT

661 TATGATTTCC CATGGTCGAC CCATCGATTA GTCCCCTTTG GTTGGTACGG TGGAGTTGCT

721 CATCATGATT TACATCATTC ACAATTTAAT TGTAATTTTG CACCATATTT TACTCATTGG

781 GACAGAATTT TGGGTACCTT AAGGTCTGCA CCAGCCAAAT AATGAGAATT C
```

The corresponding amino acid sequence is:

```
SEQ. ID NO: 9:
    1 MSSHNSSGPL ALGPPGQLLL QPLWDQVRAR AALAQSPPFA VLFSITAYLG CCLPFVLLDL

61 LCPRVRALRR YKVHPDCGPS ARQLLGCLGR TVCQHVALLL PASLLHCARG PAPWPREAPE

121 LLQLARHVLG CLLLFDAEVF AWHVLHHRVP WLYRTFHKLH HQHAASFALA TQYMGAWELL
```

```
181 SLGFFHVLNV VLLQCHPLSV LAFHLLNIWL SVEDHSGYDF PWSTHRLVPF GWYGGVAHHD

241 LHHSQFNCNF APYFTHWDRI LGTLRSAPAK
```

Example 3

Construction of the Expression Plasmid V51TDH-S24R1

Expression vectors were constructed using the classical molecular biology technology as described by Sambrook et al. (1989) and the DNA restriction and modification enzymes were used as recommender by the supplier (New England Biolabs, Ipswich, Mass. 01938-2723, USA).

The basic multi-copy constitutive expression vector V51TDH was derived from the V51 vector by replacing the galactose inducible GAL10-CYC1 promoter with the promoter from the constitutively expressed TDH3 gene (YGR192C gene from systematic gene annotation in the Saccharomyces Genome Database, coding for the glyceraldehyde-3-phosphate dehydrogenase isozyme 3). V51 carries the ColE1 replication origin and bla gene (resistance to ampicillin) for maintenance in Escherichia coli, the 2μ origin and the URA3 gene for maintenance in yeast, the GAL10-CYC1 hybrid promoter and PGK1 terminator regions separated by a multiple cloning site (MCS) (pYeDP1/8-2, Cullin and Pompon, 1988). The TDH3 Promoter region was amplified by PCR on genomic DNA from the W303-1B yeast strain (Thomas and Rothstein, 1989) and prepared according to Hoffman and Winston (1987) using the following primers:

```
PTDHAge
                              (SEQ. ID. NO: 10)
5'-CACCGGTGCCATTTCAAAGAATACGTA-3'

PTDHBam
                              (SEQ. ID. NO: 11)
5'-TGGATCCTTATGTGTGTTTATTCGAAAC-3'
```

The PCR amplification product was digested by Age I and Bam HI and used to replace the 617 bp long AgeI-Bam HI fragment from V51 carrying the GAL10-CYC1 promoter. The resulting V51TDH vector is a multiple copy E. coli/S. cerevisiae shuttle vector useful for the constitutive expression of a gene of interest in yeast by insertion into the MCS localized between the TDH3 promoter (TDH3p) and the PGK1 terminator (PGK1t) regions.

Figure 1:
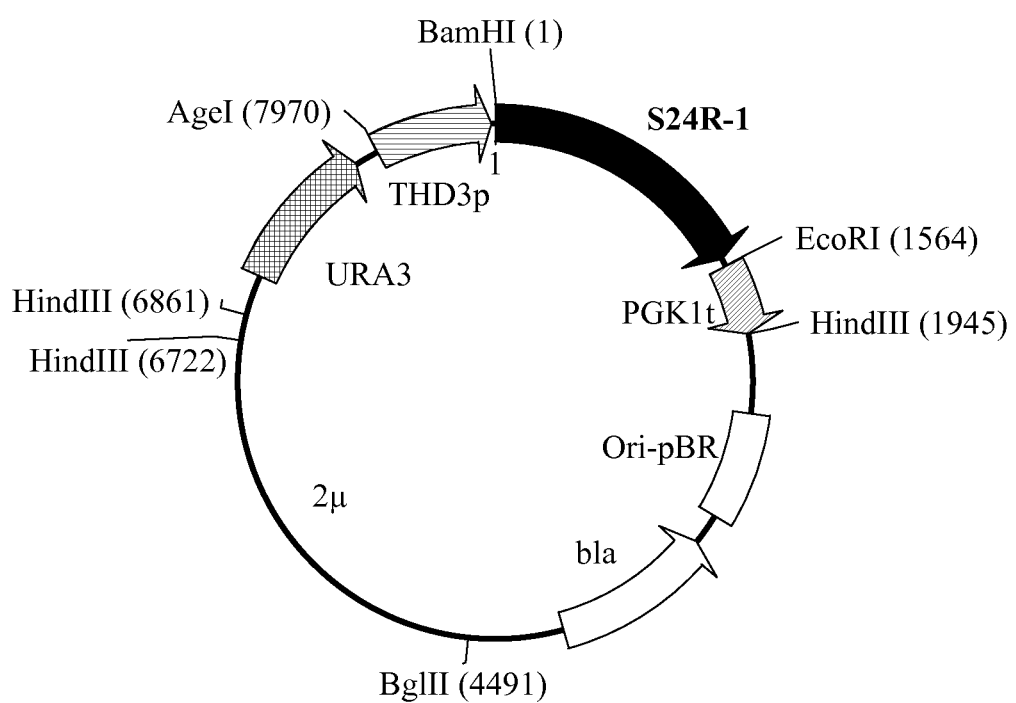
FIG. 1: Restriction map of the plasmid V51TDH-S24R1. S24R-1 is the synthetic gene S24R1 coding for the putative sterol Δ24-reductase from *Rattus norvegicus*.

The V51TDH-S24R1 vector for constitutive expression of the S24R1 synthetic gene (see Example 1) was constructed by insertion of the 1564 bp Bam HI-Eco RI restriction product from the S24R1 synthetic gene into the V51TDH vector restricted by Bam HI and Eco RI. The restriction map of the V51TDH-S24R1 constitutive expression vector is given in FIG. 1.

Example 4

Construction of the Expression Plasmid V51TDH-S24R2

Figure 2:
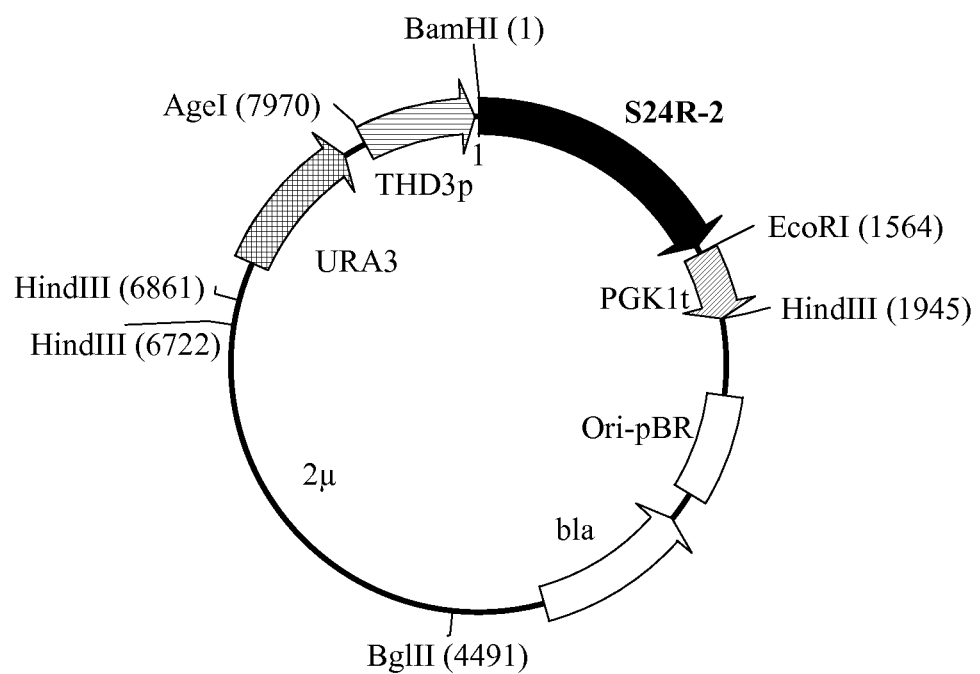
FIG. 2: Restriction map of the plasmid V51TDH-S24R2. S24R-2 for the synthetic gene S24R2 coding for the putative sterol Δ24-reductase from *Danio rerio*.

The V51TDH-S24R2 vector for constitutive expression of S24R2 (see Example 1) was basically constructed as already described in Example 3. The 1564 bp large Bam HI-Eco RI restriction product of the synthetic gene S24R2 was ligated into the V51TDH vector restricted by Bam HI and Eco RI. The restriction map of V51TDH-S24R2 is given in FIG. 2.

Example 5

Construction of the Centromeric Expression Plasmid pFLAde-S24R1

The centromeric pFLAde-S24R1 vector for constitutive expression of the gene S24R1 (see Example 1) was constructed by insertion of the TDH3p-S24R1-PGK1t expression cassette from V51TDH-S24R1 (described in Example 3) into the empty pFLAde E. coli/S. cerevisiae shuttle vector carrying an yeast centromer and autonomous replication sequence (ARS CEN) and the ADE2 selection marker. The pFLAde vector was constructed by replacing the 1.1 kb Bgl II fragment of pFL38 (Bonneaud et al., 1991) coding for the URA3 gene by a 2.7 kb Bam HI fragment encoding the ADE2 gene obtained by PCR amplification on yeast genomic DNA using the following primers:

```
ADE2-1
                              (SEQ ID NO: 12)
5'-CGGATCCACTAGTAACGCCGTATCGTGATTAACG-3',

ADE2-2
                              (SEQ. ID NO: 13)
5'-AGGATCCTCCTGACGTAGCTATCCTCGGTTCTG-3'.
```

The TDH3p-S24R1-PGK1t expression cassette was amplified by PCR using the PrimeSTAR HS DNA Polymerase (Takara, Otsu, Shiga, Japan) under standard conditions and the following primers:

```
TDH
                              (SEQ. ID NO: 14)
5'-AGGCGCGCCACCGGTGCCATTTCAAAGAA-3'

PGK
                              (SEQ. ID. NO: 15)
5'-AGGCGCGCCCAAGCTTTAACGAACGCAGA-3'.
```

Figure 3:
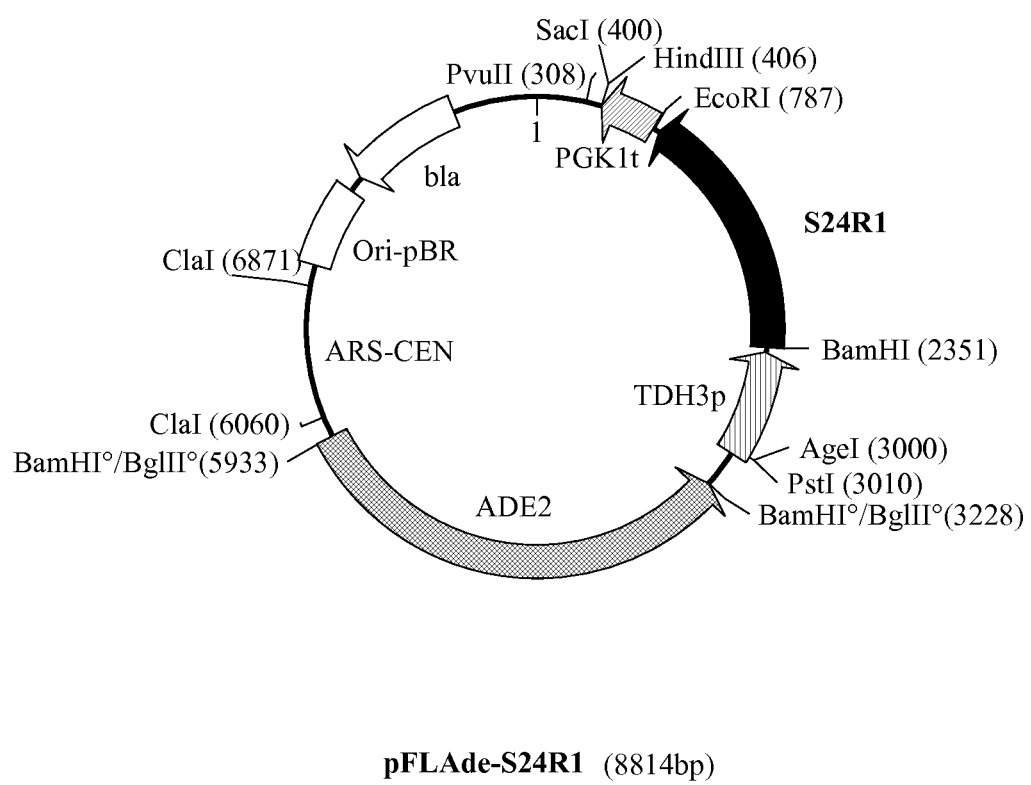
FIG. 3: Restriction map of the plasmid pFLAde-S24R1. S24R1 for the synthetic gene S24R1 coding for the putative sterol Δ24-reductase from *R. norvegicus*; ARS-CEN is the centromeric autonomously replication origin for *S. cerevisiae*; ADE2 for the *S. cerevisiae* ADE2 gene.

The amplification product was cloned into pCR2.1-TOPO (Invitrogen, Carlsbad, Calif. 92008, USA). The TDH3p-S24R1-PGK1t cassette was isolated from the later vector by Sac I-Pst I restriction and ligated into the pFLAde vector cut by the same restriction enzymes. The restriction map of the resulting pFLAde-S24R1 centromeric expression vector is given in FIG. 3.

Example 6

Construction of the Expression Vector V51-C25H1

The V51-C25H1 plasmid for galactose inducible expression of C25H1 (see Example 2) was constructed by inserting the 826 bp Bam HI-Eco RI fragment from of C25H1 into V51 digested with Bam HI and Eco RI. The resulting V51-C25H1 expression plasmid encodes the synthetic gene C25H1 under the control of the galactose inducible GAL10-

Figure 4:
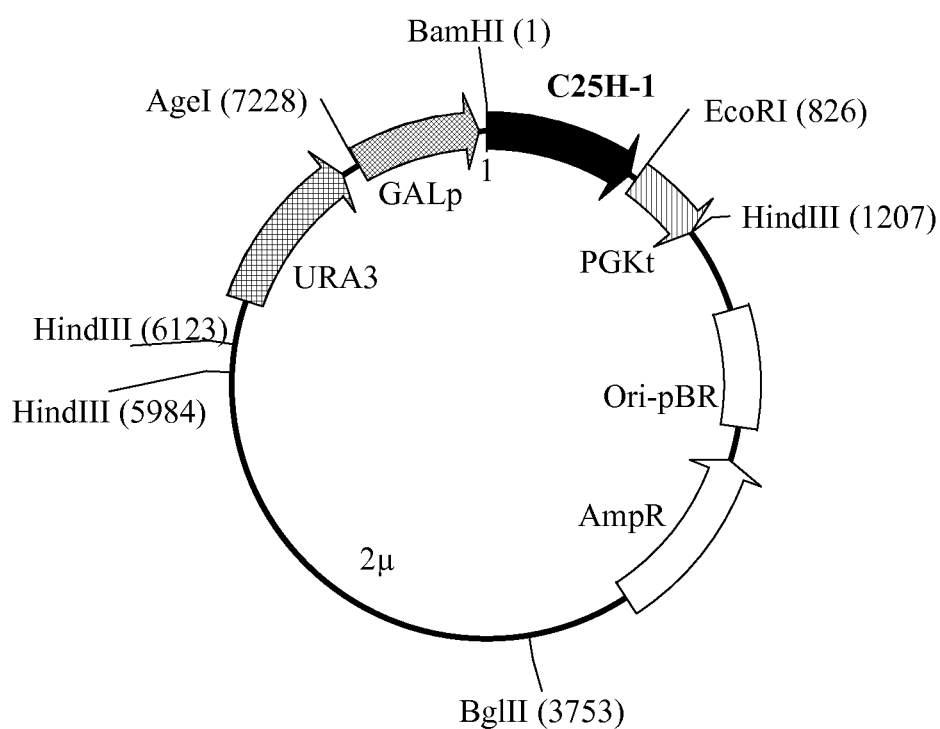
FIG. 4: Restriction map of the plasmid V51-C25H1. GALp stands for the GAL10-CYC1 (Guarente et al., 1982) galactose inducible promoter region; C25H-1 for the synthetic gene C25H1 coding for the putative cholesterol C25-hydroxylase from *Sus scrofa*.

CYC1 hybrid promoter (Guarente et al., 1982) and the PGK1 terminator. The restriction map of V51-C25H1 is given in FIG. 4.

Example 7

Construction of the Expression Vector V51-C25H3

Figure 5:
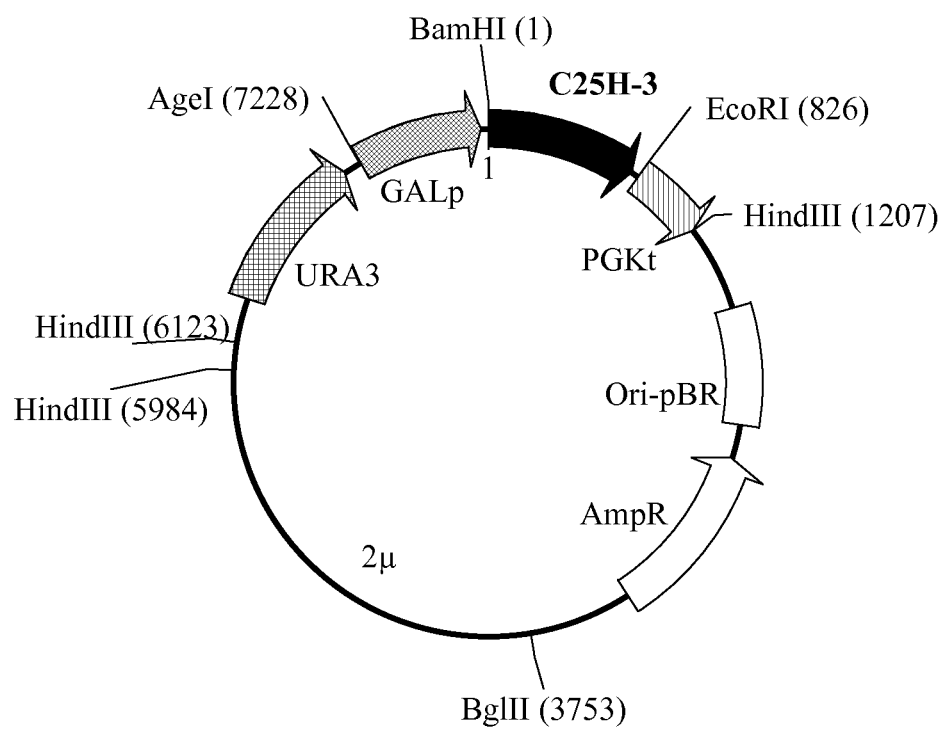
FIG. 5: Restriction map of the plasmid V51-C25H3. GALp stands for the GAL10-CYC1 (Guarente et al., 1982) galactose inducible promoter region; C25H-3 for the synthetic gene C25H3 coding for the putative cholesterol C25-hydroxylase from *Canis familiaris*.

The V51-C25H3 vector for galactose inducible expression of the synthetic gene C25H3 (see Example 2) was constructed as already described in Example 6 by inserting the 826 bp Bam HI-Eco RI fragment of the synthetic gene C25H3 into V51 digested with Bam HI and Eco RI. The resulting expression plasmid V51-C25H3 codes for C25H3 under the control of the galactose inducible GAL10-CYC1 hybrid promoter and the PGK1 terminator. The restriction map of V51-C25H3 is given in FIG. 5.

Example 8

Transformation of Yeast Strains and Sterol Extraction

Strain W303-1B (MATalpha; ura3-52; trp1-1; leu2-3,112; his3-11; ade2-1; can1-100; Thomas and Rothstein, 1989) and its erg6 mutant ERT (MATalpha; erg6::TRP1; ura3-52; trp1-1; leu2-3,112; his3-11; ade2-1; can1-100) were transformed with the different expression plasmids described above. The inactivation of ERG6 of strain ERT was obtained by insertion of the functional TRP1 gene into ERG6. The TRP1 gene from pFL45 (Bonneaud et al., 1991) was amplified by PCR using TRP1 primers bordered by ERG6 sequences. The sequences of the primers are the following:

```
ERGTRP-1:
                                     (SEQ. ID. NO: 16)
5'-CATAAGATGAGTGAAACAGAATTGAGAAAAAGACAGGCCCAATCAA

ATTCGGGTCGAAAAAAGAAAAG-3',

ERGTRP-2:
                                     (SEQ. ID. NO: 17)
5'-CTAGCGACGAAAAGCATCATTGGAGTGAATAACTTGGACTTACCAT

TCTTAGCATTTTGAC-3'.
```

The resulting PCR product was used to transform strain W303-1B using the lithium-PEG technique as described by Gietz et al. (1995). Transformants were selected on a defined medium without tryptophan, and their sterol composition was verified by HPLC (Lecain et al., 1996) confirming the absence of ergosterol and the presence of unusual sterols consistent with the known effect of an ERG6 inactivation. One erg6::TRP1 transformant was kept for further studies and designated ERT.

In addition to ERT, also the *S. cerevisiae* wild type strain BY4742 (genotype MATalpha; his3Δ1; leu2Δ0; lys240; ura340; Brachmann et al., 1998) was used as host for the plasmids constructed.

Transformation of BY4742, W303-1B and ERT was done by the lithium-PEG method as described by Gietz et al. (1995). The transformants were selected on a defined minimal medium (Table 1) without uracil or adenine depending on the selection marker present on the vector. At least two independent transformants of each transformation were analyzed. For sterol analysis the transformants were grown in synthetic medium (described in Table 2) to the stationary phase.

Yeast cells were recovered from the cultivation medium by centrifugation and washed with an equal volume of de-ionized water. The cells were re-suspended in 100 μl of water in a 2 ml Eppendorf tube and were broken by strong vortexing (5 min) in presence of 0.1 g glass beads (0.5 mm). 2 ml 1,2-dichloroethane were added to the resuspended cells and the mixture was intensively vortexed for 5 minutes. After 5 minutes centrifugation at 10,000 rpm the solvent phase was transferred into a glass tube. The extraction was done twice. The pooled organic phase was evaporated under nitrogen. As the last step, the dried extract was re-suspended in 100 μl acetonitrile for HPLC analysis.

Example 9

Sterol Analysis by High Performance Liquid Chromatography (HPLC) with UV and Mass Spectrometry Detection An aliquot, usually 30 μl, of the sterol extract prepared as described in Example 8 was analyzed by reverse phase HPLC monitored by UV and mass spectrometry detection. A "Waters Alliance HT 2790" HPLC was coupled to a photodiode array UV detector from type "Waters PDA 996" and to the mass detector "Waters MicroMass ZQ" (Waters, Milford, Mass. 01757, USA). The separation was done on a XTerra RP18 3.5 μm 4.6×100 mm column (Waters, Milford, Mass. 01757, USA) at 60° C. with a linear 0.03% (v/v) formic acid containing water/acetonitrile gradient. The sample was injected after stabilization of the column with a buffer containing 80% of buffer A (water with 0.0 3% formic acid) and 20% of buffer B (acetonitrile with 0.03% of formic acid). For the first 5 minutes, the buffer composition was gradually changed from 80% of buffer A and 20% of buffer B to 25% of buffer A and 75% of buffer B. In the next 15 minutes, the buffer composition was gradually changed from 25% of buffer A and 75% of buffer B to 12.5% of buffer A and 87.5%. In the last minute of the separation protocol 100% of buffer B was reached. This value was maintained for 2 minutes to allow the regeneration of the column.

The chromatography was monitored between 205 to 300 nm with a photodiode array detector. The mass detector allowed the detection by positive electrospray of m/z ranging from 350 to 450 with a sensitivity of 1 unit of m/z.

The sterols were identified on the basis of their chromatographic behavior, their UV absorption spectra and their mass fragmentation profiles in comparison to standards (Table 5). The 25-hydroxy 7-dehydrocholesterol standard (provided by DSM) was acetylated into 25-hydroxy-7-dehydrocholesterol acetate (25OH-7DHC-Ac.) with acetic anhydride in presence of pyridine according to Seçen and Kalpar (1999). 0.5 mg of dry 25-hydroxy 7-dehydrocholesterol was re-suspended into 1 ml of acetic anhydride/pyridine solution (50/50 v/v) and heated at 55° C. for 3 hours. The reaction mixture was diluted with 4 ml of water. 0.5 ml of the diluted reaction mixture was extracted with 1,2-dichloroethane as described in Example 8 prior to HPLC analysis.

Analyzed under the conditions described above, the 25OH-7DHC-Ac standard showed a shift in retention time (RT 8.5 min) compared to the non acetylated 25-hydroxy-7-dehydrocholesterol standard (RT 6.9 min) due to the higher hydrophobicity of the acetylated compound. The mass fragmentation profile of the 25OH-7DHC-Ac standard was similar to the profile of the non acetylated 25-hydroxy 7-dehydrocholesterol standard. An m/z signal corresponding to the acetylated form was never detected probably because of the de-acetylation that occurs during the detection in the mass detector.

5,7,24-trienol and cholesta 5,7,22,24-tetraenol confirmed the sterol Δ24-reductase activity of gene S24R1 (see FIG. 13).

TABLE 5

Chromatographic, spectral and mass fragmentation properties of the different sterols

| Compounds | Usual name | Abbreviation | Retention Time | Max UV absorption | m/z |
| --- | --- | --- | --- | --- | --- |
| Ergosta 5,7,22-trienol | Ergosterol | E5,7,22 | 11.9 min | 282 nm | 379 |
| Ergosta 5,7,22,24-tetraenol | / | E5,7,22,24 | 10.0 min | 233 nm | 377 |
| Cholesta 5,7,22,24-tetraenol | / | C5,7,22,24 | 9.2 min | 233 nm | 363 |
| Cholesta5,7,24-trienol | / | C5,7,24 | 10.3 min | 282 nm | 365 |
| Cholesta5,7,22-trienol | / | C5,7,22 | 10.8 min | 282 nm | 365 |
| Cholesta5,7-dienol | 7-Dehydrocholesterol (7-DHC) | C5,7 | 11.8 min | 282 nm | 367 |
| 25Hydroxy-cholesta5,7-dienol acetate | 25OH-7DHC-Ac | 25OH-C5,7-Ac | 8.5 min | 282 nm | 365-383 |
| 25Hydroxy-ergosterol acetate | 25OH-Ergosterol-Ac | 25OH-E5,7,22-Ac | 8.7 min | 282 nm | 377-395 |

Example 10

Expression of the S24R1 Gene from Plasmid V51TDH-S24R1 in the ERG6-Deficient *S. Cerevisiae* Strain ERT Plasmid V51TDH-S24R1 (see Example 3) and the empty vector V51TDH as control were transformed into the strain ERT by the lithium-PEG technique (Gietz et al., 1995). The transformants were selected on a defined minimal medium without uracil. Four independent transformants from each transformation were analyzed for existence of the plasmid. One of the confirmed transformant was randomly chosen, named respectively ERT/V51TDH and ERT/V51TDH-S24R1, and used for further analysis.

The strains were grown to the stationary phase in 2% (w/v) glucose Kapelli medium (Table 2), all sterols were extracted as described in Example 8 and analyzed by HPLC with UV and mass spectrometry detections as described in Example 9. The major sterols were identified by their retention time, mass and spectral properties using the respective standards (Table 5).

HPLC elution profiles (UV detection at 282 nm) are shown in FIG. 6. Cholesta-5,7,22,24-tetraenol (RT 9.2 min, m/z=363, UV max 233 nm) was the major sterol found in the ERT/V51TDH erg6 control strain corresponding to 70% of the UV signal at 282 nm. 7% of the total sterols identified at 282 nm were identified as cholesta 5,7,24-trienol (RT 10.3 min, m/z=365, UV max 282 nm; FIG. 6-A).

The sterol profile of strain ERT/V51TDH-S24R1 (FIG. 6-B) expressing the S24R1 gene revealed the presence of two sterols not detected in the control strain ERT/V51TDH, namely, to cholesta 5,7,22-trienol (RT 10.8 min, m/z=365, UV max 282 nm), the major sterol of this strain (60% of UV signal at 282 nm), and cholesta 5,7-dienol, also named 7-dehydrocholesterol (RT 11.8 min, m/z=367, UV max 282 nm). The presence of cholesta 5,7,-dienol and cholesta 5,7,22-trienol generated by reduction of the $\Delta^{24-25}$ bond of cholesta Example 11

Expression of the Gene S24R2 from Plasmid V51TDH-S24R2 in *S. Cerevisiae* Strain ERT Plasmid V51TDH-S24R2 (Example 3) constitutively expressing S24R2 was transformed into strain ERT using the lithium-PEG protocol (Gietz et al., 1995). Transformants were selected on minimal medium without uracil. Four independent transformants were analyzed and showed the same properties. One of them was designated ERT/V51TDH-S24R2 and used for further analysis.

The strain was cultured until it reached the stationary phase in 2% glucose Kapelli medium (Table 2) and the sterols were extracted and analyzed as described in Examples 8, 9, and 10. Again, cholesta 5,7,22,24-tetraenol (RT 9.2 min, m/z=363, UV max 233 nm) and cholesta 5,7,24-trienol (RT 10.3 min, m/z=365, UV max 282 nm) were found as the major sterols in the control strain ERT/V51TDH (FIG. 6-A), while the major sterol detected in the S24R2 expressing strain ERT/V51TDH-S24R2 was cholesta 5,7,22-trienol (RT 10.8 min, m/z=365, UV max 282 nm) with 70% of UV signal at 282 nm (FIG. 6-C). Cholesta 5,7-dienol (7-dehydrocholesterol; RT 11.8, m/z=367, UV max 282 nm) was found in lower concentrations (13% of UV signal). These results confirm the sterol Δ24-reductase activity of the S24R2 gene.

Example 12

Expression of Gene S24R1 from the Centromeric Plasmid pFLAde-S24R1 in *S. Cerevisiae* Strain ERT The centromeric plasmid pFLAde-S24R1 (Example 5) for constitutive expression of the gene S24R1 was transformed into the ERT strain using the lithium-PEG procedure (Gietz et al., 1995). The transformants were selected on a defined medium without adenine. Four independent transformants were analyzed for occurrence of the plasmid pFLAde- S24R1 and for their sterol pattern. One of them was randomly chosen, designated ERT/pFLAde-S24R1, and used for further illustration of the results.

ERT/pFLAde-S24R1 was grown in 2% glucose Kapelli medium (Table 2) until it reached the stationary phase. Sterols were extracted and analyzed as described in Examples 8 and 9. The major new sterol in ERT/pFLAde-S24R1, not present in the control, was cholesta 5,7,22-trienol (RT 10.8 min, m/z=365, UV max 282 nm) with 60% of the UV signal at 282 nm (FIG. 6-D). A smaller amount (7% of UV signal) of 7-dehydrocholesterol (RT 11.8, m/z=367, UV max 282 nm) was also detected. Beside those new sterols, cholesta 5,7,22,24-tetraenol (RT 9.2 min, m/z=363, UV max 233 nm) and cholesta 5,7,24 (RT 10.3 min, m/z=365, UV max 282 nm) that were also present in the ERT control strain (FIG. 6-A) were also found in ERT/pFLAde-S24R1. These results confirm the sterol Δ24-reductase activity of the S24R1 gene expressed from the centromeric plasmid pFLAde-S24R1.

Example 13

Production of 25-hydroxy-7-dehydrocholesterol acetate by Co-Expression of the Genes S24R1 and C25H1 in the *S. Cerevisiae* Strain ERT Plasmid V51-C25H1 (Example 6) for galactose inducible expression of the gene C25H1, and plasmid V51 as control, was transformed into strain ERT/pFLAde-S24R1 (described in Example 12) with the lithium-PEG method (Gietz et al., 1995). V51-C25H1 and pFLAde-S24R1 are compatible plasmids. Their different origins, 2μ and an ARS-CEN, allow their simultaneous occurrence in yeast. The transformants were selected on minimal medium without uracil and adenine. Four independent transformants from each transformation were analyzed and showed the same properties. One transformant from each transformation was randomly chosen, designated ERT/pFLAde-S24R1N51-C25H1 and ERT/pFLAde-S24R1/V51, respectively, and used for further analysis.

The strains were grown in 2% galactose Kapelli medium (Table 2) until they reached the stationary phase. Sterols were extracted and analyzed by HPLC with UV and mass spectrometry detection as described in Examples 8 and 9 under the conditions described in Example 10. As found for the control strain ERT/pFLAde-S24R1/V51 (FIG. 7-C), the major sterol in ERT/pFLAde-S24R1N51-C25H1 (FIG. 7-D) was cholesta 5,7,22-trienol (RT 10.8 min, m/z=365, UV max 282 nm), generated by reduction of the final sterol cholesta 5,7,22,24-tetraenol by the sterol Δ24-reductase. A new compound, not present in the control strain, was observed in strain ERT/pFLAde-S24R1/V51-C25H1 (FIG. 7-D) which eluted at the same time as the prepared 25-hydroxy 7-dehydrocholesterol acetate (25OH-7DHC-Ac), injected as standard (RT 8.5 min, FIG. 7-B). This compound showed also an identical UV absorption profile (FIG. 8-C) as the prepared 25-hydroxy 7-dehydrocholesterol acetate (FIG. 8-B), with the double peak around 282 nm, specific to the Δ5-Δ7 conjugated double bounds as also observed for the 7-dehydrocholesterol standard (FIG. 8-A). The new compound showed also a mass fragmentation profile (FIG. 9-C) identical to 25-hydroxy 7-dehydrocholesterol acetate (FIG. 9-B) as determined by on-line mass spectrometry analysis (done as described in Example 9).

In the case of 3β-hydroxysterols, the electrospray analysis produces a major signal at molecular weight minus seventeen (protonation (+1) and dehydratation at position C3 (−18). The major signal for 7-dehydrocholesterol (FIG. 9-A) is at m/z mass of 367 (384 (7-dehydrocholesterol MW)+1 (protonation)-18 (3β-hydroxysterol dehydratation)). The signal observed for the 25-hydroxy 7-dehydrocholesterol acetate at m/z mass of 383 corresponds to the additional hydroxylation at position C-25 (367+16=383). The major signal at m/z mass of 365 corresponds to the dehydratation at position C25 (383−18=365) which occurs for a fraction of the molecules during the detection inside the mass detector. These different results (same retention time, same UV profile, and same mass fragmentation as 25-hydroxy 7-dehydrocholesterol acetate used as standard) demonstrated that the new compound produced in the ERT/pFLAde-S24R1N51-C25H1 strain was 25-hydroxy 7-dehydrocholesterol acetate.

Example 14

Production of 25-hydroxy-7-dehydrocholesterol acetate by Co-Expression of S24R1 and C25H3 in *S. Cerevisiae* Strain ERT V51-C25H3 (Example 7), constructed for galactose inducible expression of gene C25H3, was transformed into strain ERT/pFLAde-S24R1 (see Example 13) by the lithium-PEG method (Gietz et al., 1995). The transformants were selected on minimal medium without uracil and adenine. Four independent transformants were analyzed for confirmation of the occurrence of both plasmids. One of them was randomly chosen, named ERT/pFLAde-S24R1N51-C25H3, and used for further studies.

ERT/pFLAde-S24R1N51-C25H3 was grown in 2% galactose Kapelli medium (Table 2) up to the stationary phase. From the harvested cells the sterols were extracted and analysed by HPLC with UV and mass spectrometry detections as described in Examples 8 and 9 under the conditions as described in Example 10. As found in the control strain ERT/pFLAde-S24R1/V51 (FIG. 7-C), the major sterol in ERT/pFLAde-S24R1/V51-C25H3 (FIG. 7-E) was cholesta 5,7,22-trienol (RT 10.8 min, m/z=365, UV max 282 nm), the reduction product of the final sterol cholesta 5,7,22,24-tetraenol by the sterol Δ24-reductase as already described in Example 13.

A compound, not present in the parental strain, was found in ERT/pFLAde-S24R1N51-C25H3 (FIG. 7-E) eluting at the same time as 25-hydroxy 7-dehydrocholesterol acetate (RT 8.5 min, FIG. 7-B). As in the case of ERT/pFLAde-S24R1N51-C25H1 (described in Example 13), this compound showed the identical UV absorption profile (FIG. 8) and the identical mass fragmentation profile (FIG. 9) as 25-hydroxy 7-dehydrocholesterol acetate. These results (retention time, UV profile, and mass fragmentation are comparable to 25-hydroxy 7-dehydrocholesterol acetate) demonstrate that the new compound produced in ERT/pFLAde-S24R1N51-C25H3 is as in Example 13, 25-hydroxy 7-dehydrocholesterol acetate.

Example 15

Production of 25-hydroxy-ergosterol acetate by Expression of C25H1 in the *S. Cerevisiae* Strains W303-1B and BY4742

Plasmid V51-C25H1 (Example 6) constructed for galactose inducible expression of gene C25H1, and the empty vector V51 as control, were transformed into strain W303-1B (described in Example 8) by the lithium-PEG method (Gietz et al., 1995). The transformants were selected on minimal medium without uracil. Four independent transformants for each transformation were analyzed for occurrence of the plasmid. One positive transformant of each transformation was randomly chosen, designated W303/V51-C25H1 and W303/V51 respectively, and used for further studies.

The strains were grown in 2% galactose Kapelli medium (Table 2) until they reached the stationary phase. Sterols were extracted from the harvested cells and analyzed by HPLC with UV and mass spectrometry detections as described in Example 8 and 9 under the conditions as described in Example 10. The HPLC elution profiles (UV detection at 282 nm) are shown in FIG. 10. The major signal observed for both strains W303/V51-C25H1 (FIG. 10-C) and W303/V51 (FIG. 10-B) corresponded to ergosterol (ergosta 5,7,22-trienol), the mayor sterol of a *S. cerevisiae* wild-type strains, as demonstrated by comparison with the retention time (FIG. 10-A), the UV spectrum (FIG. 11-A), and the mass fragmentation profile (FIG. 12-A) of ergosterol (RT 11.9 min, m/z=379, UV max 282 nm).

A minor signal at 10 min for strain W303/V51-C25H1 (FIG. 10-C) was only observed as a trace signal for the W303/V51 control strain (FIG. 10-B). The UV profile of this peak determined by on-line PDA detection (FIG. 11-B) showed a maximum absorption at 233 nm specific to the conjugated double bonds Δ22 and Δ24, in addition to the conjugated double bonds Δ5 and Δ7 that are characterized by the double peak around 282 nm. Probably, this signal corresponded to ergosta 5,7,22,24-tetraenol, one of the last intermediates of the ergosterol biosynthetic pathway without reduction of Δ24 by Erg4p (see FIG. 13). The m/z mass of 377 detected by on-line mass spectrometry (FIG. 12-B) was consistent with an ergosta-tetraenol structure.

A third signal at 8.7 min observed in a sterol extract of strain W303/V51-C25H1 (FIG. 10-C) by HPLC was completely absent in W303/V51 (FIG. 10-B). The UV profile determined of this peak (FIG. 11-C) showed the typical double peak with a maximum at 282 nm specific to the conjugated double bounds Δ5 and Δ7. The mass fragmentation (FIG. 12-C) showed a major signal at m/z=377 and a minor signal at m/z=395, consistent with a hydroxylated form of ergosterol (379+16=395) and its dehydratation form (395−18=377). The fragmentation profile (FIG. 12-C) was identical to the one of 25-hydroxy 7-dehydrocholesterol acetate (FIG. 9-B) except that all masses were increased by 12 mass units, corresponding to the mass difference between 7-dehydrocholesterol (m/z=367) and ergosterol (m/z=379). The 3.2 min retention time difference between this new compound (RT 8.7 min) and ergosterol (RT 11.9 min) was identical to the retention time difference between 25-hydroxy 7-dehydrocholesterol acetate (RT 8.5 min) and 7-dehydrocholesterol, (RT 11.8).

All these properties (UV profile, mass fragmentation, retention time) are consistent with the conclusion that this new compound produced by C25H1 expression in W303/V51-C25H1 was 25-hydroxy-ergosterol acetate.

Transformation of V51-C25H1 and the empty vector V51 as control into the *S. cerevisiae* strain BY4742 led to results (FIG. 10) comparable the ones obtained for strains W303/V51-C25H1 and W303N51. The additional signal at 8.7 min was observed again by HPLC (UV detection) for the V51-C25H1 transformant. The compound showed the same UV profile (FIG. 11) and mass fragmentation profile (FIG. 12) as the compound detected in W303/C25H1 strongly indicating that this compound is also 25-hydroxy-ergosterol acetate.

Example 16

Production of 25-hydroxy-ergosterol acetate by Expression of Gene C25H3 in *S. Cerevisiae* Strain W303-1B Plasmid V51-C25H3 (Example 7) constructed for galactose inducible expression of the synthetic gene C25H3 was transformed into strain W303-1B (described in Example 8) using the lithium-PEG method (Gietz et al., 1995). The transformants were selected on minimal medium without uracil. Four independent transformants were analysed for occurrence of V51-C25H3. One positive transformant was designated W303/V51-C25H3 and used for further investigations of the produced sterols.

The strains were grown in 2% galactose Kapelli medium (Table 2) until they reached the stationary phase. Sterols were extracted from the harvested cells and analyzed by HPLC with UV and mass spectrometry detections as described in Examples 8 and 9 under the conditions as described in Example 10.

Analysis of the sterol extracts by HPLC (UV detection at 282 nm) as given in FIG. 10-D showed that the sterol pattern of W303/V51-C25H3 was very similar to the sterol pattern of strain W303/V51-C25H1 (Example 15), with a new compound (RT 8.7 min) produced in addition to ergosterol (RT 11.9 min) and ergosta 5,7,22,24-tetraenol (RT 10.0 min). On-line UV PDA detection (FIG. 11) and mass spectrometry (FIG. 12) showed that this new compound had the same properties as the compound produced by W303/V51-C25H1 e.g. the specific conjugated double bond UV profile of Δ5-Δ7, a mass fragmentation with a major signal at m/z=377 and a minor signal at m/z=395, and an HPLC retention time delay consistent with an 25-hydroxylated sterol. All these characteristics (UV profile, mass fragmentation, retention time) strongly indicate that this new compound is 25-hydroxy-ergosterol acetate resulting from expression of C25H3.

Example 17

Introduction of C25H1 and C25H3 into a Yeast Strain Producing Mainly cholesta-5,7,24-trienol Plasmid V51-C25H1 (Example 6) and plasmid V51-CH25H3 (Example 7) for galactose inducible expression of genes C25H1 and C25H3, and plasmid V51 as control, were transformed into strain ERT erg5 erg6 (described in Example 12; ERG5 was inactivated by integration of the gene URA3) with the lithium-PEG method (Gietz et al., 1995). The transformants were selected on minimal medium without uracil and adenine. Four independent transformants from each transformation were analyzed and showed the same properties. One transformant from each transformation was randomly chosen, designated ERT erg5 erg6/V51-C25H1, ERT erg5 erg6/V51-C25H3 and ERT erg5 erg6/V51, respectively, and used for further analysis.

The strains were grown in 2% galactose Kapelli medium (Table 2) until they reached the stationary phase. Sterols were extracted and analyzed by HPLC with UV and mass spectrometry detection as described in Examples 8 and 9 under the conditions described in example 10. No difference in the sterol pattern was detected among the three strains proving that the two hydroxylases are not active on cholesta-5,7,24-trienol.

Example 18

Selection of Additional Cholesterol 25-hydroxylase Genes

In addition to the selected putative cholesterol 25-hydroxylase genes from *S. scrofa* and *C. familiaris* (*Canis lupus*), the homologous genes from *R. norvegicus* (SEQ. ID. NO:21, gene bank accession number NP_001020586, XP_220063), *P. troglodytes* (SEQ. ID. NO:18, gene bank accession number XP_507901), and *E. caballus* (SEQ. ID. NO:24, gene bank accession number XP_001503057) were also investigated in more detail.

Two different codon-optimized genes for expression in *S. cerevisiae* for each selected 25-hydroxylase were calculated (SEQ. ID. NOS:19, 20, 22, 23, 25, 26). All genes ending with the suffix "_opt" were codon-optimized by the company DNA 2.0 (Menlo Park, Calif., USA) using their proprietary algorithm. All genes with the suffix "_HY" were generated by always placing the most common codon for each amino acid at each position the amino acid occurs in the sequence. Typical codon usage tables for yeast are publicly available and are also part of the program suite Lasergene.

Two new optimized genes for the 25-hydroxylase from *S. scrofa* (see Example 2) were also calculated by using the same methods described above (SEQ. ID. NO:27, 28).

Using the amino acid sequence alignment that was calculated with the known algorithm ClustalW as input, a consensus amino acid sequence was determined by simply selecting the most abundant amino acid for each position. If a "most abundant amino acid" could not be determined, the amino acid for the respective position was chosen arbitrarily. This ConHyD amino acid sequence (SEQ. ID. NO:29) was also back-translated into two different DNA sequences as described above (SEQ. ID. NO:30, 31).

```
Amino acid sequence of the putative cholesterol 25-hydroxylase from P.
troglodytes:
                                                          SEQ. ID. NO: 18
MSCHNCSDPQVLCSSGQLFLQPLWDHLRSWEALLQSPFFPVIFSITTYVGFCLPFVVLDILCSWVPALRRYKIHP

DFSPSARQLLPCLGQTLYQHVMFVFPVTLLHWARSPALLPHEAPELLLLLHHILFCLLLFDMEFFVWHLLHHKVP

WLYRTFHKVHHQNSSSFALATQYMSVWELFSLGFFDMMNVTLLGCHPLTTLTFHVVNIWLSVEDHSGYNFPWSTH

RLVPFGWYGGVVHHDLHHSHFNCNFAPYFTHWDKILGTLRTASVPAR

DNA sequence of P. troglodytes CH25OH_opt 2.0
                                                          SEQ. ID. NO: 19
ATGTCATGTCATAACTGTTCTGATCCTCAAGTTTTGTGTTCAAGTGGTCAACTGTTCCTGCAACCTCTTTGGGAT

CACTTGAGAAGTTGGGAGGCACTATTGCAGTCTCCATTCTTCCCTGTGATCTTCTCTATTACTACCTATGTTGGA

TTCTGTTTGCCATTTGTGGTGCTGGACATTCTATGCTCATGGGTTCCTGCCTTGAGAAGGTATAAGATACATCCT

GACTTTTCCCCTTCTGCTAGACAACTTTTACCATGCTTAGGGCAAACATTGTACCAACACGTGATGTTCGTTTTC

CCAGTGACATTGTTGCATTGGGCTAGATCCCCAGCTTTACTTCCACACGAAGCCCCAGAACTGTTACTTCTACTA

CACCACATTCTGTTCTGCTTGCTGCTATTTGATATGGAGTTTTTCGTATGGCACTTGCTTCATCACAAAGTCCCA

TGGTTATACAGAACCTTTCATAAAGTACATCACCAAAACTCCTCTTCCTTTGCACTGGCCACTCAGTACATGTCT

GTTTGGGAATTGTTTAGTTTAGGGTTTTTCGATATGATGAATGTCACGTTGCTAGGCTGTCACCCATTAACGACA

TTAACATTTCATGTTGTCAATATCTGGTTGTCAGTTGAGGATCATAGTGGCTACAACTTCCCATGGTCTACGCAC

AGATTAGTACCATTCGGTTGGTATGGTGGTGTTGTACATCATGACTTGCATCACTCTCATTTCAATTGTAACTTT

GCTCCTTACTTCACACATTGGGATAAGATCCTAGGAACTCTGAGAACAGCCTCAGTACCTGCAAGGTAATGA

DNA sequence of P. troglodytes CH25OH_HY
                                                          SEQ. ID. NO: 20
ATGTCTTGTCACAACTGTTCTGATCCACAAGTTTTGTGTTCTTCTGGTCAATTGTTCTTGCAACCATTGTGGGAT CACTTGAGATCaTGGGAAGCcTTGTTGCAATCTCCATTCTTCCCAGTTATTTTCTCTATTACTACTTACGTTGGT

TTCTGTTTGCCATTCGTTGTTTTGGATATTTTGTGTTCTTGGGTTCCAGCTTTGAGAAGATACAAGATTCACCCA

GATTTCTCTCCATCTGCTAGACAATTGTTGCCATGTTTGGGTCAAACTTTGTACCAACACGTTATGTTCGTTTTC

CCAGTTACTTTGTTGCACTGGGCTAGATCcCCAGCTTTGTTGCCACACGAAGCTCCAGAATTGTTGTTGTTGTTG

CACCACATTTTGTTCTGTTTGTTGTTGTTCGATATGGAgTTCTTCGTTTGGCACTTGTTGCACCACAAGGTTCCA

TGGTTGTACAGAACTTTCCACAAGGTTCACCACCAAAACTCTTCTTCTTTCGCTTTGGCTACTCAATACATGTCT

GTTTGGGAATTGTTCTCTTTGGGTTTCTTCGATATGATGAACGTTACTTTGTTGGGTTGTCACCCATTGACTACT

TTGACTTTCCACGTTGTTAACATTTGGTTGTCTGTTGAAGATCACTCTGGTTACAACTTCCCATGGTCTACTCAC
```

```
AGATTGGTTCCATTCGGTTGGTACGGTGGTGTTGTTCACCACGATTTGCACCACTCTCACTTCAACTGTAACTTC

GCTCCATACTTCACTCACTGGGATAAGATTTTGGGTACTTTGAGAACTGCTTCTGTTCCAGCTAGATAATGA
```

Amino acid sequence of the putative cholesterol 25-hydroxylase from R. norvegicus

SEQ. ID. NO: 21

```
MACHNVSELQDLGCSNQLLLQPLWDSIRTGEASARSPFFPVIFSIFTYLGFCLPFVVLDVLCPWVPILRRYKIHP

DFSPSVRQLLPCLGLTLYQHLVFVFPVTLMHWARSPALLPREAPELSQLLSHVLICLLLFDTEIFAWHLLHHKVP

WLYRTFHKVHHQNSSSFALATQYMSVWELLSLTFFDVLNVAMLQCHPLTILVFHVVNIWLSVEDHSGYDFPWSTH

RLVPFGWYGGVAHHDLHHSQFNCNFAPYFTHWDKMLGTLRCAPHSKRLCAGSESCLDSGEQCTVHLNQKKKQT
```

DNA sequence of R. norvegicus CH25OH_opt 2.0

SEQ. ID. NO: 22

```
ATGGCTTGTCATAATGTTTCAGAATTGCAGGATTTGGGTTGTAGTAACCAATTACTACTACAACCACTTTGGGAC

TCTATCAGAACTGGCGAAGCATCTGCTCGTTCTCCATTCTTCCCTGTCATTTTCTCCATTTTCACTTACTTAGGC

TTTTGTCTGCCATTTGTAGTCTTGGATGTACTTTGTCCATGGGTTCCTATACTTAGAAGATACAAGATCCATCCT

GACTTCTCACCATCCGTCAGGCAGTTGCTACCTTGCTTGGGTCTAACATTGTATCAGCACCTAGTGTTCGTTTTT

CCAGTCACATTGATGCACTGGGCTAGATCACCAGCCCTGCTACCTAGAGAAGCACCAGAGTTATCTCAATTACTG

TCCCATGTACTGATATGCTTGTTGTTGTTTGACACTGAAATCTTTGCTTGGCATCTTTTACACCACAAAGTTCCT

TGGTTATACAGAACCTTCCATAAGGTGCATCACCAAAACTCATCTTCATTTGCTTTAGCCACTCAATACATGAGT

GTGTGGGAGCTGTTATCATTAACCTTTTTCGATGTCCTTAATGTTGCCATGCTTCAATGTCACCCTTTGACAATT

CTGGTTTTTCATGTTGTCAACATCTGGTTGTCTGTAGAAGATCACTCTGGATATGATTTCCCATGGTCTACTCAT

AGGTTAGTTCCTTTCGGTTGGTACGGGGGTGTAGCACATCATGATCTGCATCATAGTCAATTCAACTGCAATTTC

GCACCATACTTCACACATTGGGATAAGATGCTAGGGACTCTAAGATGTGCCCCACACTCCAAGAGACTTTGTGCT

GGATCAGAATCTTGCCTAGATAGTGGTGAACAATGTACAGTGCACTTGAACCAGAAAAAGAAACAAACATGATAA

TGA
```

DNA sequence of R. norvegicus CH25OH_HY

SEQ. ID. NO: 23

```
ATGGCTTGTCACAACGTTTCTGAATTGCAAGATTTGGGTTGTTCTAACCAATTGTTGTTGCAACCATTGTGGGAT

TCTATTAGAACTGGTGAAGCaTCTGCTAGATCaCCATTCTTCCCAGTTATTTTCTCTATTTTCACTTACTTGGGT

TTCTGTTTGCCATTCGTTGTTTTGGATGTTTTGTGTCCATGGGTTCCAATTTTGAGAAGATACAAGATTCACCCA

GATTTCTCTCCATCTGTTAGACAATTGTTGCCATGTTTGGGTTTGACTTTGTACCAACACTTGGTTTTCGTTTTC

CCAGTTACTTTGATGCACTGGGCTAGATCaCCAGCTTTGTTGCCAAGAGAAGCTCCAGAATTGTCTCAATTGTTG

TCTCACGTTTTGATTTGTTTGTTGTTGTTCGATACTGAAATTTTCGCTTGGCACTTGTTGCACCACAAGGTTCCA

TGGTTGTACAGAACTTTCCACAAGGTTCACCACCAAAACTCTTCTTCTTTCGCTTTGGCTACTCAATACATGTCT

GTTTGGGAATTGTTGTCTTTGACTTTCTTCGATGTTTTGAACGTTGCTATGTTGCAATGTCACCCATTGACTATT

TTGGTTTTCCACGTTGTTAACATTTGGTTGTCTGTTGAAGATCACTCTGGTTACGATTTCCCATGGTCTACTCAC

AGATTGGTTCCATTCGGTTGGTACGGTGGTGTTGCTCACCACGATTTGCACCACTCTCAATTCAACTGTAACTTC

GCTCCATACTTCACTCACTGGGATAAGATGTTGGGTACTTTGAGATGTGCTCCACACTCTAAGAGATTGTGTGCT

GGTTCTGAATCTTGTTTGGATTCTGGTGAACAATGTACTGTTCACTTGAACCAAAAGAAGAAGCAAACTTAATGA
```

Amino acid sequence of the putative cholesterol 25-hydroxylase from E. caballus:

SEQ. ID. NO: 24

```
MSGHNSSELHVLCSSGQLFLQPLWDSLRTREALTHSPFFPVIFSIATYVGFCLPFVVLDLLC

PWVPALRRYKIHPDFLPSARQVLPCLGQTLYQHLVFVFPATLLLWARGPVFLPLEAPELLQL

AFHVVFCLLLFDTEFFLWHVLHHKVPWLYRTFHKMHHQNSSSFALATQYMSIWELFSLVFFD

IMNVTLLECHPLTILVFHVVNIWLSVEDHSGYDFPWSTHRLVPFGWYGGVAHHDLHHSQFNC

NFAPYFTHWDKILGTLRSAHAK
```

DNA sequence of E. caballus CH25OH_opt 2.0
SEQ. ID. NO: 25
ATGTCCGGCCATAACTCATCAGAACTTCATGTTTTGTGTTCCTCTGGCCAATTGTTCCTACAACCTTTGTGGGAT
TCACTGAGAACTAGAGAGGCTCTTACACACTCCCCATTCTTCCCAGTAATCTTCTCAATCGCAACTTACGTTGGA
TTTTGTTTGCCATTTGTTGTCCTTGACTTGTTATGCCCTTGGGTGCCAGCCCTTAGAAGATACAAGATACATCCT
GATTTTCTGCCAAGTGCCAGACAGGTCTTGCCATGCTTAGGTCAAACCCTTTACCAACATCTAGTGTTCGTATTC
CCTGCAACACTATTGCTATGGGCTAGAGGGCCAGTATTTCTGCCTTTAGAAGCCCCTGAACTATTACAATTAGCA
TTCCATGTCGTCTTTTGTCTGTTGTTATTCGATACCGAGTTTTTCCTGTGGCATGTTTTACATCATAAAGTACCA
TGGTTATACCGTACATTTCACAAAATGCACCATCAAAACAGTTCCTCTTTCGCCCTTGCTACTCAGTATATGTCT
ATCTGGGAACTGTTTAGTCTAGTCTTTTTCGACATTATGAACGTTACATTGTTGGAATGTCACCCATTGACAATA
CTTGTTTTTCATGTTGTGAATATCTGGCTTTCTGTTGAAGATCACTCTGGTTACGATTTCCCTTGGTCAACACAT
AGGTTAGTTCCATTCGGATGGTATGGTGGAGTGGCTCACCATGATTTGCATCACTCACAATTCAATTGCAATTTC
GCACCATACTTCACTCACTGGGATAAGATTTTGGGTACACTAAGGTCTGCACACGCTAAGTAATGA DNA sequence of E. caballus CH25OH_HY
SEQ. ID. NO: 26
ATGTCTGGTCACAACTCTTCTGAATTGCACGTTTTGTGTTCTTCTGGTCAATTGTTCTTGCAACCATTGTGGGAT
TCTTTGAGAACTAGAGAGGCTTTGACTCACTCTCCATTCTTCCCAGTTATTTTCTCTATTGCTACTTACGTTGGT
TTCTGTTTGCCATTCGTTGTTTTGGATTTGTTGTGTCCATGGGTTCCAGCTTTGAGAAGATACAAGATTCACCCA
GATTCTTGCCATCTGCTAGACAAGTTTTGCCATGTTTGGGTCAAACTTTGTACCAACACTTGGTTTTCGTTTTC
CCAGCTACTTTGTTGTTGTGGGCTAGAGGTCCAGTTTTCTTGCCATTGGAAGCTCCAGAATTGTTGCAATTGGCT
TTCCACGTTGTTTTCTGTTTGTTGTTGTTCGATACTGAATTTTTCTTGTGGCACGTTTTGCACCACAAGGTTCCA
TGGTTGTACAGAACTTTCCACAAGATGCACCACCAAAACTCTTCTTCTTTCGCTTTGGCTACTCAATACATGTCT
ATTTGGGAATTGTTCTCTTTGGTTTTCTTCGATATTATGAACGTTACTTTGTTGGAATGTCACCCATTGACTATT
TTGGTTTTCCACGTTGTTAACATTTGGTTGTCTGTTGAAGATCACTCTGGTTACGATTTCCCATGGTCTACTCAC
AGATTGGTTCCATTCGGTTGGTACGGTGGTGTTGCTCACCACGATTTGCACCACTCTCAATTCAACTGTAACTTC
GCTCCATACTTCACTCACTGGGATAAGATTTTGGGTACTTTGAGATCAGCTCACGCTAAGTAATGA DNA sequence of S. scrofa CH25OH_opt 2.0

SEQ. ID. NO: 27

ATGTCTGGTCATAACAATTCTGAGCTATTAGTTCTATGTTCTAGTGGACAGTTGTTCCTTCAGCCATTATGGGAT

CATTTGAAAACCTGGGAAACTTTGATTCAATCACCATTCTTCCCAGTCTTTTTCTCAATAACAACTTATCTGGGT

TTCTGTTTACCTTTCGTAGTGCTAGATGTTCTATGTCCTTGGGTGCCAGCACTTAGAAGATACAAGATCCACCCT

GACTTCTCACCATCCGTTTGGCAACTACTTCCATGTTTAGGATTAACCCTTTACCAACATGTTGTTTTTGTTTTT

CCAATGACACTATTACACTGGGCTGCTTCACCTGTCTTACTACCTCCTGAAGCTCCTGAGTTACTGCAATTAGTG

AGACATATAGTTTTGTGCTTGCTTCTGTTCGATACTGAGTTTTTCATTTGGCATGTCTTGCATCACAAAGTACCA

TGGTTGTATAGGACATTTCATAAGATGCACCATCAGAACAGTTCCTCTTTCGCCCTGGCCACTCAATACATGTCA

GTCGGCGAACTGTTGTCTTTGGGTGTATTTGATATGGTTAACATCATGCTACTACGTTGTCATCCACTTACAGTG

TTGATCTTTCATGTCATTAACATCTGGCTTTCAGTAGAAGATCATAGTGGATACGACTTTCCATGGTCTACTCAC

AGACTGGTTCCATTCGGTTGGTACGGAGGTGTAACACACCACGATTTGCATCACTCTCAATTCAATTGCAATTTC

GCTCCATACTTCACACATTGGGATAAGATATTGGGCACATTAAGATCCGCACACGCAAAGTAATGA

DNA sequence of *S. scrofa* CH25OH_HY

SEQ. ID. NO: 28

ATGTCTGGTCACAACAACTCTGAATTGTTCGTTTTGTGTTCTTCTTCTCAATTGTTCTTGCAACCATTGTGGGAT

CACTTGAAGACTTGGGAAACTTTGATTTTGTCTCCATTCTTCCCAGTTTTCTTCTCTATTACTACTTACTTGGGT

TTCTGTTTGCCATTCGTTGTTTTGGATGTTTTGTGTCCATGGGTTCCAGCTTTGAGAAGATACAAGATTCACCCA

-continued

GATTTCTCTCCATCTGTTTGGCAATTGTTGCCATGTTTGGGTTTGACTTTGTACCAACACGTTGTTTTCGTTTTC

CCAATGACTTTGTTGCACTGGGCTGCTTCTCCAGTTTTGTTGCCACCAGAAGCTCCAGAATTGTTGCAATTGGTT

AGACACATTGTTTTGTGTTTGTTGTTGTTCGATACTGAgTTCTTCATTTGGCACGTTTTGCACCACAAGGTTCCA

TGGTTGTACAGAACTTTCCACAAGATGCACCACCAAAACTCTTCTTCTTTCGCTTTGGCTACTCAATACATGTCT

GTTGGTGAATTGTTGTCTTTGGGTGTTTTCGATATGGTTAACATTATGTTGTTGAGATGTCACCCATTGACTGTT

TTGATTTTCCACGTTATTAACATTTGGTTGTCTGTTGAAGATCACTCTGGTTACGATTTCCCATGGTCTGCTCAC

AGATTGGTTCCATTCGGTTGGTACGGTGGTGTTACTCACCACGATTTGCACCACTCTCAATTCAACTGTAACTTC

GCTCCATACTTCACTCACTGGGATAAGATTTTGGGTACTTTGAGATCaGCTCACGCTAAGTAATGA

Amino acid sequence of ConHyD

SEQ. ID. NO: 29

MSCHNSSELQVLCSSGQLFLQPLWDHLRTWEALIQSPFFPVIFSITTYVGFCLPFVVLDVLCPWVPALRRYKIHP

DFSPSARQLLPCLGQTLYQHVVFVFPVTLLHWARSPALLPREAPELLQLLSHVLFCLLLFDTEFFVWHLLHHKVP

WLYRTFHKVHHQNSSSFALATQYMSVWELlSLGFFDMLNVTLLQCHPLTVLTFHVVNIWLSVEDHSGYDFPWSTH

RLVPFGWYGGVAHHDLHHSQFNCNFAPYFTHWDKILGTLRSAhAK

DNA sequence of ConHyD_opt 2.0

SEQ. ID. NO: 30

ATGTCTTGCCACAATTCCTCTGAGCTTCAAGTATTGTGTTCATCAGGTCAGTTGTTTTTGCAACCATTATGGGAT

CACTTAAGGACGTGGGAAGCCCTGATTCAAAGTCCTTTCTTCCCTGTGATATTCTCCATAACTACTTACGTGGGC

TTTTGTTTACCATTTGTTGTTTTGGATGTTCTATGCCCATGGGTTCCAGCTCTGAGAAGATACAAGATTCATCCA

GATTTCTCCCCTTCAGCCAGACAATTGTTACCATGTTTGGGGCAAACACTATATCAGCATGTGGTCTTTGTTTTC

CCTGTGACTCTATTACATTGGGCCAGAAGTCCTGCTTTGCTGCCTAGAGAAGCCCCTGAACTGTTGCAGTTATTG

TCTCACGTCTTATTCTGTTTGCTGCTTTTCGATACAGAGTTTTTCGTTTGGCATCTACTTCATCATAAAGTTCCA

TGGCTGTATAGAACGTTCCACAAAGTCCACCACCAGAACTCTAGTTCATTCGCATTGGCCACCCAATACATGTCC

GTATGGGAACTGCTATCTTTAGGCTTTTTCGATATGCTTAATGTCACTCTTTTGCAATGTCATCCTTTGACAGTG

CTAACATTCCATGTAGTGAACATCTGGTTATCTGTAGAAGATCACAGTGGATATGATTTTCCTTGGTCTACTCAC

AGGTTGGTTCCATTTGGATGGTATGGTGGTGTAGCTCATCACGACCTGCATCATTCACAATTCAATTGCAACTTT

GCTCCATACTTTACACATTGGGACAAAATCTTGGGAACATTAAGGTCTGCTCATGCAAAGTGA

DNA sequence of ConHyD_HY

SEQ. ID. NO: 31

ATGTCTTGTCACAACTCTTCTGAATTGCAAGTTTTGTGTTCTTCTGGTCAATTGTTCTTGCAACCATTGTGGGAT

CACTTGAGAACTTGGGAAGCaTTGATTCAATCTCCATTCTTCCCAGTTATTTTCTCTATTACTACTTACGTTGGT

TTCTGTTTGCCATTCGTTGTTTTGGATGTTTTGTGTCCATGGGTTCCAGCTTTGAGAAGATACAAGATTCACCCA

GATTTCTCTCCATCTGCTAGACAATTGTTGCCATGTTTGGGTCAAACTTTGTACCAACACGTTGTTTTCGTTTTC

CCAGTTACTTTGTTGCACTGGGCTAGATCaCCAGCTTTGTTGCCAAGAGAAGCTCCAGAATTGTTGCAATTGTTG

TCTCACGTTTTGTTCTGTTTGTTGTTGTTCGATACTGAATTtTTCGTTTGGCACTTGTTGCACCACAAGGTTCCA

TGGTTGTACAGAACTTTCCACAAGGTTCACCACCAAAACTCTTCTTCTTTCGCTTTGGCTACTCAATACATGTCT

GTTTGGGAATTGTTGTCTTTGGGTTTCTTCGATATGTTGAACGTTACTTTGTTGCAATGTCACCCATTGACTGTT

TTGACTTTCCACGTTGTTAACATTTGGTTGTCTGTTGAAGATCACTCTGGTTACGATTTCCCATGGTCTACTCAC

AGATTGGTTCCATTCGGTTGGTACGGTGGTGTTGCTCACCACGATTTGCACCACTCTCAATTCAACTGTAACTTC

GCTCCATACTTCACTCACTGGGATAAGATTTTGGGTACTTTGAGATCaGCTCACGCTAAGTAATGA

Example 19

Expression of the New 25-hydroxylase Genes from an Expression Construct Integrated into ERG6

The new genes shown in Example 18 were integrated into the ERG6 locus of *S. cerevisiae* SC0554 (erg5, erg6, TRP1-pARC300D, URA3-pARC304S, ARE1::TDH3p-S24R2-PGKt-URA3; for a description of two plasmids see U.S. Pat. No. 5,460,949).

The sequence of the integration construct is shown below. The hydroxylases of interest were cloned between the Bam HI and Eco RI site of the integration construct. The ERG6 integration construct possessed the TDH3 promoter and the PGK terminator of *S. cerevisiae* for expression and the URA3 of *S. cerevisiae* for selection as found in the plasmid V51TDH. Culturing, transformation and selection were done as described above.

The final strains were called:

*S. cerevisiae* Ecab HY (integration construct possessing the gene of SEQ. ID. NO:26), Ecab opt 2.0 (integration construct possessing the gene of SEQ. ID. NO:25), Ptro opt 2.0 (integration construct possessing the gene of SEQ. ID. NO:19), Ptro HY (integration construct possessing the gene of SEQ. ID. NO:20), ConHyD HY (integration construct possessing the gene of SEQ. ID. NO:31), ConHyD opt 2.0 (integration construct possessing the gene of SEQ. ID. NO:30), Rnor HY (integration construct possessing the gene of SEQ. ID. NO:23), Rnor opt 2.0 (integration construct possessing the gene of SEQ. ID. NO:22), Sscr HY (integration construct possessing the gene of SEQ. ID. NO:28), Sscr opt 2.0 (integration construct possessing the gene of SEQ. ID. NO:27), and Scr Pompon, which possessed the 25-hydroxylase from pig optimized as described in Example 2.

```
DNA sequence of the ERG6 integration construct
                                                    SEQ. ID. NO: 32
gtcgacGTTTTACTTTCGATTTAAGTTTTACATAATTTAAAAAAACAAGAATAAAATAATAATATAGTAGGCAGC

ATAAGATGAGTGAAACAGAATTGAGAAAAAGACAGGCCCAATTCACTAGGGAGTTACATGGTGATGATATTGGTA

AAAAGACAGGTTTGAGTGCATTGATGTCGAAGAACAACTCTGCCCAAAAGGAAGCCGTTCAGAAGTACTTGAGAA

ATTGGGATGGTAGAACCGATAAAGATGCCGAAGAACGTCGTCTTGAGGATTATAATGAAGCCACACATTCCTACT

ATAACGTCGTTACAGATTTCTATGAATATGGTTGaGGTTCCTCTTTCCATTTCAGCAGATTTTATAAAGGTGAGA

GTTTCGCTGCCTCGATAGCAAGACATGAACATTATTTAGCTTACAAGGCTGGTATTCAAAGAGGCGATTTAGTTC

TCGACGTTGGTTGTGGTGTTGGGGGCCCAGCAAGAGAGATTGCAAGATTTACCGGTGCCATTTCAAAGAATACGT

AAATAATTAATAGTAGTGATTTTCCTAACTTTATTTAGTCAAAAAATTAGCCTTTTAATTCTGCTGTAACCCGTA

CATGCCCAAAATAGGGGCGGGTTACACAGAATATATAACATCGTAGGTGTCTGGGTGAACAGTTTATTCCTGGC

ATCCACTAAATATAATGGAGCCCGCTTTTTAAGCTGGCATCCAGAAAAAAAAAGAATCCCAGCACCAAAATATTG

TTTTCTTCACCAACCATCAGTTCATAGGTCCATTCTCTTAGCGCAACTACAGAGAACAGGGGCACAAACAGGCAA

AAAACGGGCACAACCTCAATGGAGTGATGCAACCTGCCTGGAGTAAATGATGACACAAGGCAATTGACCCACGCA

TGTATCTATCTCATTTTCTTACACCTTCTATTACCTTCTGCTCTCTCTGATTTGGAAAAAGCTGAAAAAAAAGGT

TGAAACCAGTTCCCTGAAATTATTCCCCTACTTGACTAATAAGTATATAAAGACGGTAGGTATTGATTGTAATTC

TGTAAATCTATTTCTTAAACTTCTTAAATTCTACTTTTATAGTTAGTCTTTTTTTTAGTTTTAAAACACCAAGAA

CTTAGTTTCGAATAAACACACATAAggatccattattatttgaattcGCGGGGGATCTCCCATGTCTCTACTGGT

GGTGGTGCTTCTTTGGAATTATTGGAAGGTAAGGAATTGCCAGGTGTTGCTTTCTTATCCGAAAAGAAATAAATT

GAATTGAATTGAAATCGTAGATCAATTTTTTTCTTTTCTCTTTCCCCATCCTTTACGCTAAAATAATAGTTTATT

TTATTTTTTGAATATTTTTTATTTATATACGTATATATAGACTATTATTTATCTTTTAATGATTATTAAGATTTT

TATTAAAAAAAAATTCGCTCCTCTTTTAATGCCTTTATGCAGTTTTTTTTCCCATTCGATATTTCTATGTTCGG

GTTCAGCGTATTTTAAGTTTAATAACTCGAAAATTCTGCGTTCGAAAGCTTTTCAATTCATCTTTTTTTTTTTG

TTCTTTTTTTTGATTCCGGTTTCTTTGAAATTTTTTTGATTCGGTAATCTCCGAGCAGAAGGAAGAACGAAGGAA

GGAGCACAGACTTAGATTGGTATATATACGCATATGTGGTGTTGAAGAAACATGAAATTGCCCAGTATTCTTAAC

CCAACTGCACAGAACAAAAACCTGCAGGAAACGAAGATAAATCATGTCGAAAGCTACATATAAGGAACGTGCTGC

TACTCATCCTAGTCCTGTTGCTGCCAAGCTATTTAATATCATGCACGAAAAGCAAACAAACTTGTGTGCTTCATT

GGATGTTCGTACCACCAAGGAATTACTGGAGTTAGTTGAAGCATTAGGTCCCAAAATTTGTTTACTAAAAACACA
```

-continued

```
TGTGGAcATCTTGACTGATTTTTCCATGGAGGGCACAGTTAAGCCGCTAAAGGCATTATCCGCCAAGTACAATTT

TTTACTCTTCGAAGACAGAAAATTTGCTGACATTGGTAATACAGTCAAATTGCAGTACTCTGCGGGTGTATACAG

AATAGCAGAATGGGCAGACATTACGAATGCACACGGTGTGGTGGGCCCAGGTATTGTTAGCGGTTTGAAGCAGGC

GGCGGAAGAAGTAACAAAGGAACCTAGAGGCCTTTTGATGTTAGCAGAATTGTCATGCAAGGGCTCCCTAGCTAC

TGGAGAATATACTAAGGGTACTGTTGACATTGCGAAGAGCGACAAAGATTTTGTTATCGGCTTTATTGCTCAAAG

AGACATGGGTGGAAGAGATGAAGGTTACGATTGGTTGATTATGACACCCGGTGTGGGTTTAGATGACAAGGGAGA

CGCATTGGGTCAACAGTATAGAACCGTGGATGATGTGGTCTCTACAGGATCTGACATTATTATTGTTGGAAGAGG

ACTATTTGCAAAGGGAAGGGATGCTAAGGTAGAGGGTGAACGTTACAGAAAAGCAGGCTGGGAAGCATATTTGAG

AAGATGCGGCCAGCAAAACTAAAAAACTGTATTATAAGTAAATGCATGTATACTAAACTCACAAATTAGAGCTTC

AATTTAATTATATCAGTTATTACCCGGGAATCTCGGTCGTAATGATTTCTATAATGACGAAAAAAAAAAATTGG

AAAGAAAAGCTTATTCACTAGATCAATAAGATTCAAATAAAGCGCACGATATATACCTATTTTCCTATATATGC

AGATAAAAAGATAGCACGTTCATTGCTAGCAGGCCTTACAAACAGACTGTCCGATGCCTTTACTACCCCACAATT

TATCCCACTTGTGATTTTCAAGTTCGGCTTTTTTTTTTTCATCATGTCGTGGCAAACGACCAGTATTTTCTATC

AGAATAAGAAAAAACTATAATTCACTGCATACAAACGTATTGACTGCTCCCCTACAGCGGAAGATAGTAAGAATA

CAACATCGTAACTGTTTCCATATTTATGTGCCGATATGGTAAAAGTGAAATCTAAGAATAGTGTTATAAAGCTAT

TGTCTACAGCGGCAAGTGGATACTCTCGTTACATCTCGATTAAGAAAGGTGCACCTTTGGTTACTCAGGTCAGAT

ACGATCCTGTGGTGAAACGGCATGTGCTTTTCAAAGAAGCAAAGAAAAGGAAAGTGGCAGAAAgtcgac
```

Example 20

Shake Flask Assays of the New HyDHC Strains

The strains that were generated as described in Example 19 were cultivated in shake flasks to evaluate the effect of overexpressing the newly designed putative 25-hydroxylase genes. 4 ml of an overnight culture in YPD medium were used for inoculation of 20 ml Kapelli medium (example 1). After 24 and 48 h culturing 10 g/l and after 32 and 56 h 20 g/l glucose were fed. After 72 h culture time the cells were spun down, saponified and the sterol content was determined as described in Example 9. As shown in FIG. 15, all new hydroxylase genes were expressed in S. cerevisiae and the gene products all were able to hydroxylate 7-DHC to HyDHC, although with varying degrees of efficiency.

LITERATURE each of which is hereby incorporated by reference:

Brachmann C. B., Davies A., Cost G. J., Caputo E., Li J., Hieter P., Boeke J. D. (1998). Yeast 14(2): 115-132.
Crameri A., Biondi E., Kuehnle K., Liitjohann D., Thelen K. M., Perga S., Dotti C. G., Nitsch R. M., Ledesma M. D., Mohajeri M. H. (2006). EMBO J. 25(2):432-43.
Cullin C., Pompon D. (1988). Gene 65:203-217.
Bonneaud N., Ozier-Kalogeropoulos O., Li G. Y., Labouesse M., Minvielle-Sebastia L., Lacroute F. (1991). Yeast 7:609-615.
Gaber R. F., Copple D. M., Kennedy B. K., Vidal M, Bard M. (1989). Mol Cell Biol 9(8):3447-3456.
Guarente L., Yocum R. R., Gifford P. (1982). Proc Natl Acad Sci USA 79:7410-7414.
Hoffman C. S. and Winston F. (1987). Gene 57:267-272
Gietz R. D., Schiestl R. H., Willems A. R., Woods R. A. (1995). Yeast 11:355-360.
Lecain E., Chemvesse X., Spagnoli R., Pompon D. (1996). J Biol Chem 271(18):10866-10873.
Lund E. G., Kerr T. A., Sakai J., Li W. P., Russell D. W. (1998). J Biol Chem 273(51):34316-34327.
Sambrook J., Fritsch E. F., Maniatis T. (1998). Molecular cloning: a laboratory manual. 2nd ed. Cold Spring Harbor, N.Y.: Cold Spring Harbor Laboratory.
Seçen H., Kalpar H. (1999). Turk J Chem 23: 27-30.
Thomas B. J. and Rothstein R. (1989). Cell 56(4):619-630.
Waterham H. R., Koster J., Romeijn G. J., Hennekam R. C. M., Vreken P., Andersson H. C., FitzPatrick D. R., Kelley R. I., Wanders R. J. A. (2001). Am J Hum Genet. 69:685-694.
Wu C., Miloslayskaya I., Demontis S., Maestro R., Galaktionov K. (2004). Nature 432 (7017):640-5.
Zhang S. P., Zubay G., Goldman E. (1991). Gene 1005:61-72.

What is claimed is:

1. Yeast comprising a nucleic acid encoding cholesterol C25-hydroxylase which has been codon-optimized for expression in yeast and encodes a cholesterol C25 hydroxylase with an amino acid sequence that is at least 90% identical with an amino acid sequence selected from the group consisting of SEQ ID NO: 6, SEQ ID NO: 9, SEQ ID NO: 18, SEQ ID NO: 21, SEQ ID NO: 24, and SEQ ID NO: 29;
wherein the yeast possesses no active Erg5p and Erg6p enzymes, and the yeast also expresses a sterol Δ24-reductase.

2. The yeast of claim 1, wherein the yeast expresses a truncated version of HMG1.

3. A method of producing 25-hydroxy-7-dehydrocholesterol in a genetically modified yeast comprising:
a) transforming the yeast with a nucleic acid encoding cholesterol C25-hydroxylase; wherein said nucleic acid encoding cholesterol C25 hydroxylase has been codon-optimized for expression in yeast and encodes a cholesterol C25 hydroxylase with an amino acid sequence that is at least 90% identical with an amino acid sequence selected from the croup consisting of SEQ ID NO: 6, SEQ ID NO: 9, SEQ ID NO: 18, SEQ ID NO: 21, SEQ ID NO: 24, and SEQ ID NO: 29; and
b) contacting 7-dehydrocholesterol with said cholesterol C25-hydroxylase expressed in yeast;
wherein the yeast possesses no active Erg5p and Erg6p enzymes, and the yeast also expresses a sterol Δ24-reductase.

4. The method according to claim 3, wherein the yeast expresses a truncated version of HMG1.

5. The method according to claim 3 further comprising prior to step a):
contacting cholesta-5,7,24-trienol with a yeast comprising a nucleic acid sequence that encodes a functional sterol Δ24-reductase enzyme, whereby the yeast converts lanosterol, dimethyl zymosterol, methyl zymosterol, zymosterol, cholesta-7, 24-dienol, or cholesta-5,7,24-trienol to 3β-hydroxy-8-lanosta-8-ene, 4,4-dimethyl-cholesta-8-enol, 4α-methyl-cholesta-8-enol, cholesta-8-enol, lathosterol or 7-dehydrocholesterol, respectively.

6. The method according to claim 3, wherein the expression in the codon-optimized C25-hydroxylase in the genetically modified yeast is at least as in the range of the expression of the C25-hydroxylase according to SEQ ID NO:5.

7. The method according to claim 3, wherein the codon-optimized C25-hydroxylase is encoded by a nucleotide sequence selected from the group consisting of SEQ ID NOs: 5, 8, 19, 20, 22, 23, 25, 26, 27, 28, 30, and 31.

* * * * *